United States Patent
Hata et al.

(10) Patent No.: US 8,252,294 B2
(45) Date of Patent: Aug. 28, 2012

(54) METHODS OF SCREENING FOR COMPOUNDS THAT INHIBIT THE BIOSYNTHESIS OF GPI IN MALARIA PARASITES

(75) Inventors: Katsura Hata, Ibaraki (JP); Kaoru Ogawa, Ibaraki (JP); Itaru Tsukada, Ibaraki (JP); Kazutaka Nakamoto, Ibaraki (JP); Koji Sagane, Ibaraki (JP); Keigo Tanaka, Ibaraki (JP); Kappei Tsukahara, Ibaraki (JP); Toshihiro Horii, Osaka (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/040,970

(22) Filed: Mar. 4, 2011

(65) Prior Publication Data

US 2011/0201816 A1 Aug. 18, 2011

Related U.S. Application Data

(62) Division of application No. 10/535,928, filed as application No. PCT/JP03/14920 on Nov. 21, 2003, now Pat. No. 7,928,215.

(60) Provisional application No. 60/428,589, filed on Nov. 22, 2002.

(51) Int. Cl.
*A61A 39/015* (2006.01)
*C07K 12/00* (2006.01)
*C07H 21/04* (2006.01)

(52) U.S. Cl. ......... 424/268.1; 514/2; 530/300; 530/350; 536/23.1; 536/23.2; 536/23.7; 536/24.5

(58) Field of Classification Search ...... 514/2; 530/300, 530/350; 536/69.1, 320, 23.1, 23.2, 23.7, 536/24.5; 424/268.1
See application file for complete search history.

(56) References Cited

U.S. PATENT DOCUMENTS

| | | |
|---|---|---|
| 2002/0019520 A1 | 2/2002 | Mao et al. |
| 2004/0038239 A1 | 2/2004 | Tsukahara et al. |
| 2006/0234283 A1 | 10/2006 | Tsukahara et al. |
| 2006/0234349 A1 | 10/2006 | Tsukahara et al. |
| 2006/0240429 A1 | 10/2006 | Tsukahara et al. |
| 2008/0166765 A1 | 7/2008 | Tsukahara et al. |
| 2008/0261272 A1 | 10/2008 | Tsukahara et al. |
| 2009/0098636 A1 | 4/2009 | Tsukahara et al. |
| 2009/0117586 A1 | 5/2009 | Tsukahara et al. |
| 2009/0325228 A1 | 12/2009 | Tsukahara et al. |

FOREIGN PATENT DOCUMENTS

| | | |
|---|---|---|
| WO | WO 98/14583 A2 | 4/1998 |
| WO | WO 00/39342 A2 | 7/2000 |
| WO | WO 01/13923 A1 | 3/2001 |
| WO | WO 02/04626 A1 | 1/2002 |
| WO | WO 02/052014 A2 | 7/2002 |
| WO | WO 2004/048604 A1 | 6/2004 |

OTHER PUBLICATIONS

Bowman, S., et al., EMBL Accession No. AL096783, 22 pgs. (Submitted: Jul. 2, 1999, Created: Jul. 2, 1999).

Brophy, Victoria Hertle, et al.; "Identification of *Cryptosporidium parvum* Dihydrofolate Reductase Inhibitors by Complementation in *Saccharomyces cerevisiae*;" *Antimicrobial Agents and Chemotherapy*; Apr. 2000; pp. 1019-1028; 44:4.

Carlton, Jane M., et al.; "Genome sequence and comparative analysis of the model rodent malaria parasite *Plasmodium yoelii yoelii*;" *Nature*; Oct. 3, 2002; pp. 512-519; 419:6906.

Cerevachi, I., et al., GenBank Accession No. AL844505 (GI: 23498324): (http://www.ncbi.nlm.nih.gov/entrez/viewer.fcgi?23498324:OLD12:31840), 530 pgs. (Oct. 2, 2002).

Cerevachi, I., et al., GenBank Accession No. CAD50425: (http://www.ncbi.nlm.nih.gov/entrez/viewer.fcgi?db=protein&id=23498474), 2 pgs. (Jan. 29, 2003).

Delorenzi, Mauro, et al.; "Genes for Glycosylphosphatidylinositol Toxin Biosynthesis in *Plasmodium falciparum*;" *Infection and Immunity*; Aug. 2002; pp. 4510-4522; 70:8.

Gardner, Malcolm J., et al.; "Genome sequence of the human malaria parasite *Plasmodium falciparum*;" *Nature*; Oct. 3, 2002; pp. 498-511; 419:6906.

Gerold, Peter, et al.; "Biosynthesis of glycosylphophatidylinositols of *Plasmodium falciparum* in a cell-free incubation system: inositol acylation is needed for mannosylation of glycosylphophatidylinositols;" *Biochemical Journal*; Dec. 15, 1999; pp. 731-738; 344, part 3.

Hall, N., et al.; "Sequence of *Plasmodium falciparum* chromosomes 1, 3-9 and 13;" *Nature*; Oct. 3, 2002; pp. 527-531; 419:6906.

Hall, N., et al.; Sequence Listing; EMBL Accession No. CR382399; Apr. 17, 2005.

Leidich, Steven D., et al.; "Temperature-sensitive Yeast GPI Anchoring Mutants gpi2 and gpi3 Are Defective in the Synthesis of *N*-Acetylglucosaminyl Phosphatidylinositol;" *The Journal of Biological Chemistry*; Jun. 2, 1995; pp. 13029-13035; 270:22.

(Continued)

*Primary Examiner* — Rodney P. Swartz
(74) *Attorney, Agent, or Firm* — Kilpatrick Townsend & Stockton LLP

(57) ABSTRACT

The present inventors succeeded in isolating GWT1 (Pf-GWT1), which is one of the enzymes involved in GPI biosynthesis in the malaria parasite *P. falciparum*. In addition, the inventors revealed that degenerate mutant DNAs, with a lower AT content than the DNA encoding the PfGWT1 protein, can complement the phenotype of GWT1-deficient yeast. Based on the findings, the present invention provides the GWT1 protein of malaria parasites and the use of the protein in methods of screening for antimalarial drugs. The present invention also provides degenerate mutant DNAs encoding proteins involved in GPI biosynthesis, and which have a lower AT content than the original DNAs. The present invention also provides methods of screening for antimalarial drugs which use the degenerate mutant DNAs.

2 Claims, 3 Drawing Sheets

OTHER PUBLICATIONS

Leidich, Steven D., et al.; Sequence Listing; EMBL Accession No. U23788; Oct. 19, 1995.

Naik, Ramachandra S., et al.; "Developmental Stage-specific Biosynthesis of Glycosylphosphatidylinositol Anchors in Intraerythrocytic *Plasmodium falciparum* and Its Inhibition in a Novel Manner by Mannosamine;" *The Journal of Biological Chemistry*; Aug. 11, 2000; pp. 24506-24511; 275:32.

Pan, Weiqing, et al.; "Vaccine candidate MSP-1 from *Plasmodium falciparum*: a redesigned 4917 by polynucleotide enables synthesis and isolation of full-length protein for *Escherichia coli* and mammalian cells;" *Nucleic Acids Research*; Feb. 15, 1999; pp. 1094-1103; 27:4.

Sequence Listings; Discloses the sequences of PfPIG-A, -B, -M, -0, PfGAA1 and PfDPM1, all 100% identical to Seq ID Nos. 11,13,15,17,21, respectively. [http://bioinf.wehi.edu.au/folders/mauro/GPI/proteins.seq.].

Shams-Eldin, Hosam, et al.; "The GPI1 homologue from *Plasmodium falciparum* complements a *Saccharomyces cerevisiae* GPI1 anchoring mutant;" *Molecular and Biochemical Parasitology*; Mar. 2002; pp. 73-81; 120:1.

Shams-Eldin, Hosam, et al.; Sequence Listing; EMBL Accession No. AJ249657; Feb. 11, 2002.

Shams-Eldin, Hosam; Sequence Listing; EMBL Accession No. AJ401202; Jul. 1, 2000.

Smith, T., et al., "Substrate Specificity of the *Plasmodium falciparum* Glycosylphosphatidylinositol Biosynthetic Pathway and Inhibition by Species-Specific Suicide Substrates," *Biochemistry*, vol. 41, pp. 12395-12406 (2002).

Uemura, H., EMBL Accession No. D29645, 2 pgs. (Submitted: Mar. 24, 1994, Created: Nov. 25, 1995).

Umemura, Mariko, et al.; "*GWT1* Gene Is Required for Inositol Acylation of Glycosylphosphatidylinositol Anchors in Yeast;" *The Journal of Biological Chemistry*; Jun. 27, 2002; pp.23639-23647; 278:26.

Withers-Martinez, Chrislaine, et al.; "PCR-based gene synthesis as an efficient approach for expression of the A+T-rich malaria genome;" *Protein Engineering*; Dec. 12, 1999; pp. 1113-1120; 12:12.

Wooden, Jason M., et al.; "Analysis in yeast of antimalaria drugs that target the dihydrofolate reductase of *Plasmodium falciparum;*" *Molecular and Biochemical Parasitology*; Mar. 1997; pp. 25-40; 85:1.

Zhang, Hanbang, et al.; "Analysis of the Antimalarial Drug Resistance Protein Pfert Expressed in Yeast;" *The Journal of Biological Chemistry*; Dec. 20, 2002; pp. 49767-49775; 277:51.

International Search Report issued for PCT/JP03/14920, 2004.

Office Action issued for Australian Application No. 2003282393 dated Jun. 14, 2006.

Office Action issued for Australian Application No. 2003282393 dated Mar. 2, 2007.

Office Action issued for Australian Application No. 2003282393 dated May 23, 2007.

Office Action issued for Australian Application No. 2007216681 dated Dec. 4, 2007.

Office Action issued for Australian Application No. 2007216681 dated Jun. 23, 2008.

Office Action issued for Canadian Application No. 2,505,067 dated Jun. 4, 2008.

Office Action issued for Canadian Application No. 2,505,067 dated Apr. 14, 2009.

Office Action issued for Canadian Application No. 2,505,067 dated Sep. 3, 2010.

Office Action issued for Chinese Application No. 200380109105.0 dated Nov. 24, 2006.

Office Action issued for Chinese Application No. 200380109105.0 dated Jul. 6, 2007.

Office Action issued for Chinese Application No. 200380109105.0 dated Mar. 7, 2008.

Office Action issued for Chinese Application No. 200710104287.2 dated Jun. 12, 2009.

Office Action issued for Chinese Application No. 200710104287.2 dated Jun. 26, 2009.

Office Action issued for Chinese Application No. 200710104286.8 dated Mar. 18, 2010.

Office Action issued for European Application No. 03774152.7 dated Dec. 11, 2006.

Office Action issued for European Application No. 03774152.7 dated Mar. 17, 2008.

Office Action issued for European Application No. 03774152.7 dated Apr. 30, 2009.

Office Action issued for European Application No. 03774152.7 dated Nov. 30, 2009.

Search Report issued for European Application No. 03774152.7 dated Sep. 18, 2006.

Office Action issued for Japanese Application No. JP2004-555010 dated Jul. 23, 2008.

Final Rejection issued for Japanese Application No. JP2004-555010 dated Jan. 28, 2009.

Office Action issued for Japanese Application No. JP2008-242395 dated Jan. 29, 2009.

Office Action issued for Japanese Application No. JP2009-071722 dated May 13, 2009.

Final Decision issued for Japanese Application No. JP2008-242395 dated May 27, 2009.

Office Action issued for Korean Application No. 10-2005-7009212 dated Jul. 31, 2006.

Office Action issued for Korean Application No. 10-2005-7009212 dated May 4, 2007.

Office Action issued for Korean Application No. 10-2005-7009212 dated Aug. 9, 2007.

Office Action issued for Korean Application No. 10-2007-7012681 dated Feb. 18, 2009.

Office Action issued for Korean Application No. 10-2006-7027915 dated Feb. 23, 2009.

Final Rejection issued for Korean Application No. 10-2007-7012681 dated Oct. 29, 2009.

Office Action issued for Korean Application No. 10-2010-7004569 dated Jun. 22, 2010.

Trial Decision issued for Korean Application No. 10-2007-7012681 dated May 13, 2011.

Search Report and Written Opinion issued for Singapore Application No. 200501701-7 dated Aug. 31, 2006.

Office Action issued for corresponding Canadian Application No. 2,704,070; dated Mar. 23, 2012.

Office Action issued for corresponding Canadian Application No. 2,721,200, dated Apr. 11, 2012.

YEp352GAPII-pfGWT1

YEp352GAPII-opfGWT1

SEQUENCE LISTING

<160> NUMBER OF SEQ ID NOS: 55

<210> SEQ ID NO 1
<211> LENGTH: 2625
<212> TYPE: DNA
<213> ORGANISM: Plasmodium falciparum

<220> FEATURE:
<221> NAME/KEY: CDS
<222> LOCATION: (1)...(2625)

<400> SEQUENCE: 1

| | | | | | | | | | | | | | | | | |
|---|---|---|---|---|---|---|---|---|---|---|---|---|---|---|---|---|
| atg | agc | aac | atg | aat | ata | ctt | gcg | tat | ctt | ttg | ata | tgt | ccc | ttt | aac | 48 |
| Met | Ser | Asn | Met | Asn | Ile | Leu | Ala | Tyr | Leu | Leu | Ile | Cys | Pro | Phe | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tta | ata | tat | ata | ttt | gac | ctt | cct | tca | tat | ata | cct | gag | tta | aat | aaa | 96 |
| Leu | Ile | Tyr | Ile | Phe | Asp | Leu | Pro | Ser | Tyr | Ile | Pro | Glu | Leu | Asn | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | ctg | gag | aat | gac | gag | gtg | ttt | ata | tat | gga | aaa | gaa | ata | aga | aag | 144 |
| Lys | Leu | Glu | Asn | Asp | Glu | Val | Phe | Ile | Tyr | Gly | Lys | Glu | Ile | Arg | Lys | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | gaa | tct | gca | tat | tct | tta | cat | tat | gaa | aaa | tat | tta | tat | gaa | tta | 192 |
| Asn | Glu | Ser | Ala | Tyr | Ser | Leu | His | Tyr | Glu | Lys | Tyr | Leu | Tyr | Glu | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| tca | aga | aga | tat | tat | gag | ata | ata | tta | aaa | tat | aat | aag | gag | ctc | ggg | 240 |
| Ser | Arg | Arg | Tyr | Tyr | Glu | Ile | Ile | Leu | Lys | Tyr | Asn | Lys | Glu | Leu | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtt | aat | caa | gaa | aaa | gaa | tat | aat | tta | ata | ata | agt | aga | gag | ata | gat | 288 |
| Val | Asn | Gln | Glu | Lys | Glu | Tyr | Asn | Leu | Ile | Ile | Ser | Arg | Glu | Ile | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| aaa | aaa | aaa | aaa | aaa | caa | aaa | aat | agt | aca | caa | gga | gaa | tat | aat | aat | 336 |
| Lys | Lys | Lys | Lys | Lys | Gln | Lys | Asn | Ser | Thr | Gln | Gly | Glu | Tyr | Asn | Asn | |
| | | | 100 | | | | | 105 | | | | | 110 | | | |

| | | | | | | | | | | | | | | | | |
|---|---|---|---|---|---|---|---|---|---|---|---|---|---|---|---|---|
| gat | gat | gat | aat | aat | tgg | aaa | tta | ttc | caa | ata | tat | gag | aag | gaa | gaa | 384 |
| Asp | Asp | Asp | Asn | Asn | Trp | Lys | Leu | Phe | Gln | Ile | Tyr | Glu | Lys | Glu | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| ccc | aga | tca | tac | gaa | tta | ata | cgt | gtt | gag | att | tac | aaa | aaa | gat | att | 432 |
| Pro | Arg | Ser | Tyr | Glu | Leu | Ile | Arg | Val | Glu | Ile | Tyr | Lys | Lys | Asp | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| ctt | tta | att | tat | aaa | aat | gaa | aaa | acc | aaa | tca | tca | ata | aaa | ttt | ata | 480 |
| Leu | Leu | Ile | Tyr | Lys | Asn | Glu | Lys | Thr | Lys | Ser | Ser | Ile | Lys | Phe | Ile | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ata | aag | aaa | aga | aaa | gat | ata | aaa | aat | tat | ttc | tca | tta | tgt | tat | caa | 528 |
| Ile | Lys | Lys | Arg | Lys | Asp | Ile | Lys | Asn | Tyr | Phe | Ser | Leu | Cys | Tyr | Gln | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | tgt | ata | aat | aaa | tta | gat | aaa | aat | gat | tat | aat | att | tta | aaa | agt | 576 |
| Asn | Cys | Ile | Asn | Lys | Leu | Asp | Lys | Asn | Asp | Tyr | Asn | Ile | Leu | Lys | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| aca | ata | aat | aat | agt | aaa | gaa | aat | ata | att | aat | agt | gct | tat | ata | tat | 624 |
| Thr | Ile | Asn | Asn | Ser | Lys | Glu | Asn | Ile | Ile | Asn | Ser | Ala | Tyr | Ile | Tyr | |
| | | 195 | | | | | 200 | | | | | 205 | | | | |

| | | | | | | | | | | | | | | | | |
|---|---|---|---|---|---|---|---|---|---|---|---|---|---|---|---|---|
| atg | tat | ata | ata | ttt | ttc | ttt | tta | tgt | ata | tat | gta | gaa | aaa | aat | tta | 672 |
| Met | Tyr | Ile | Ile | Phe | Phe | Phe | Leu | Cys | Ile | Tyr | Val | Glu | Lys | Asn | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| ttt | tta | tac | ttt | cct | ata | tta | tta | caa | aag | tat | gaa | ata | cta | aca | aca | 720 |
| Phe | Leu | Tyr | Phe | Pro | Ile | Leu | Leu | Gln | Lys | Tyr | Glu | Ile | Leu | Thr | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tta | ttt | att | tta | ttt | att | cct | cta | att | ctt | ttt | gtt | ttt | tat | ttt | | 768 |
| Leu | Phe | Ile | Leu | Phe | Ile | Pro | Leu | Ile | Leu | Phe | Val | Phe | Tyr | Phe | | |
| | | | | 245 | | | | | 250 | | | | | 255 | | |

| | | | | | | | | | | | | | | | | |
|---|---|---|---|---|---|---|---|---|---|---|---|---|---|---|---|---|
| tat | ttt | act | ata | atc | aag | ttg | ata | tgt | tct | tgt | cta | gtt | tta | tat | gta | 816 |
| Tyr | Phe | Thr | Ile | Ile | Lys | Leu | Ile | Cys | Ser | Cys | Leu | Val | Leu | Tyr | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| aca | ttt | caa | tta | att | tat | tat | act | caa | ggt | atg | cct | ata | tat | atg | gaa | 864 |
| Thr | Phe | Gln | Leu | Ile | Tyr | Tyr | Thr | Gln | Gly | Met | Pro | Ile | Tyr | Met | Glu | |
| | | 275 | | | | | 280 | | | | | 285 | | | | |

| | | | | | | | | | | | | | | | | |
|---|---|---|---|---|---|---|---|---|---|---|---|---|---|---|---|---|
| cat | agc | ata | ttg | aaa | cat | aaa | gaa | aaa | gaa | gaa | att | tgt | gat | gaa | aaa | 912 |
| His | Ser | Ile | Leu | Lys | His | Lys | Glu | Lys | Glu | Glu | Ile | Cys | Asp | Glu | Lys | |

-continued

|     |     |     | 290 |     |     |     | 295 |     |     |     | 300 |     |     |     |     |      |
|-----|-----|-----|-----|-----|-----|-----|-----|-----|-----|-----|-----|-----|-----|-----|-----|------|
| gaa | gaa | att | tgt | gat | gaa | aaa | gaa | gaa | att | tgt | gat | gaa | aaa | gaa | gaa | 960  |
| Glu | Glu | Ile | Cys | Asp | Glu | Lys | Glu | Glu | Ile | Cys | Asp | Glu | Lys | Glu | Glu |      |
| 305 |     |     |     | 310 |     |     |     | 315 |     |     |     |     |     |     | 320 |      | att tgt gat gaa aaa gaa gaa att tgt gat gaa aaa gaa gaa att tgt    1008
Ile Cys Asp Glu Lys Glu Glu Ile Cys Asp Glu Lys Glu Glu Ile Cys
                325                 330                 335 gat gaa aaa gaa gaa att ctt gat aaa aaa aaa aaa att cat gaa aaa    1056
Asp Glu Lys Glu Glu Ile Leu Asp Lys Lys Lys Lys Ile His Glu Lys
                340                 345                 350 aaa aaa aaa att cat gat aaa aaa gaa gaa att gat gaa aaa aaa aaa    1104
Lys Lys Lys Ile His Asp Lys Lys Glu Glu Ile Asp Glu Lys Lys Lys
                355                 360                 365 aaa att cat gat aaa aaa gac gaa agt cat gat aaa aat gaa gac ata    1152
Lys Ile His Asp Lys Lys Asp Glu Ser His Asp Lys Asn Glu Asp Ile
        370                 375                 380 aca tat cct gtt caa tat aat ata gaa aat gat tta tgg tac agc tca    1200
Thr Tyr Pro Val Gln Tyr Asn Ile Glu Asn Asp Leu Trp Tyr Ser Ser
385                 390                 395                 400 aaa aat gta gat att aaa atg tat tca tct tca aat aaa gga gaa gaa    1248
Lys Asn Val Asp Ile Lys Met Tyr Ser Ser Ser Asn Lys Gly Glu Glu
                405                 410                 415 tat att ata cag aat aca tta aaa cat ttt aga tta atg aat atg tgt    1296
Tyr Ile Ile Gln Asn Thr Leu Lys His Phe Arg Leu Met Asn Met Cys
                420                 425                 430 atg aca tat ata tgt atc ttt gct gtt gat ttt tat ttc ttt cca aat    1344
Met Thr Tyr Ile Cys Ile Phe Ala Val Asp Phe Tyr Phe Phe Pro Asn
                435                 440                 445 cat ttt tgt aaa tcc tat tat tat gga aat aca cta atg gat ata ggg    1392
His Phe Cys Lys Ser Tyr Tyr Tyr Gly Asn Thr Leu Met Asp Ile Gly
450                 455                 460 ata ggt gct tct ata agc tcc agt gca tat tct caa gaa ata aaa aag    1440
Ile Gly Ala Ser Ile Ser Ser Ser Ala Tyr Ser Gln Glu Ile Lys Lys
465                 470                 475                 480 ttt aca tat ata aaa gag aag aaa aga ata att gaa tta aaa cat ata    1488
Phe Thr Tyr Ile Lys Glu Lys Lys Arg Ile Ile Glu Leu Lys His Ile
                485                 490                 495 gtt tta ttt att tta gga ata tct aga ttt att gga ata tat ctt ttt    1536
Val Leu Phe Ile Leu Gly Ile Ser Arg Phe Ile Gly Ile Tyr Leu Phe
                500                 505                 510 aat tat aat tat aat ata agt gaa tat gga ata cat tgg aat ttc ttt    1584
Asn Tyr Asn Tyr Asn Ile Ser Glu Tyr Gly Ile His Trp Asn Phe Phe
                515                 520                 525 tta aca tta tgt act aca ttt ctt ata tct aat ata tgt ttt att tta    1632
Leu Thr Leu Cys Thr Thr Phe Leu Ile Ser Asn Ile Cys Phe Ile Leu
530                 535                 540 tta aaa agg ata cgt tat att ttt ctt ttt agt ata atc tct ata att    1680
Leu Lys Arg Ile Arg Tyr Ile Phe Leu Phe Ser Ile Ile Ser Ile Ile
545                 550                 555                 560 ctt ttt gaa ata gcc ata tac tat ttt gac tta cat aat tat ata tta    1728
Leu Phe Glu Ile Ala Ile Tyr Tyr Phe Asp Leu His Asn Tyr Ile Leu
                565                 570                 575 tta aaa aat gat aga tta aat ttc ttt tca tca aac aaa gaa ggc tta    1776
Leu Lys Asn Asp Arg Leu Asn Phe Phe Ser Ser Asn Lys Glu Gly Leu
                580                 585                 590 ttt aat att ata ggt tct gtt aat ttg tat tta ttt tct ttc tca tta    1824
Phe Asn Ile Ile Gly Ser Val Asn Leu Tyr Leu Phe Ser Phe Ser Leu
                595                 600                 605 ttt aaa tat tta aca aaa caa agg aca tac ata aca acc tcg aac att    1872
Phe Lys Tyr Leu Thr Lys Gln Arg Thr Tyr Ile Thr Thr Ser Asn Ile

```
                       610                  615                 620
cca aaa aat aaa aag gat atg aat aat tct atg tat tca aag aac ggt    1920
Pro Lys Asn Lys Lys Asp Met Asn Asn Ser Met Tyr Ser Lys Asn Gly
625                 630                 635                 640 aac cac aca aat agc aat ata aat aat agg aat cat aaa att gta att    1968
Asn His Thr Asn Ser Asn Ile Asn Asn Arg Asn His Lys Ile Val Ile
                645                 650                 655 cgg aat aat cat ata aat aaa tat gaa caa gat aac aca aat aag tat    2016
Arg Asn Asn His Ile Asn Lys Tyr Glu Gln Asp Asn Thr Asn Lys Tyr
            660                 665                 670 att aat aaa caa ata aat aat aat aag aat aaa ctt gat gaa gaa gaa    2064
Ile Asn Lys Gln Ile Asn Asn Asn Lys Asn Lys Leu Asp Glu Glu Glu
        675                 680                 685 aaa tta aaa aaa tta aaa aaa tta aaa aac aaa aaa aaa aat tta aaa    2112
Lys Leu Lys Lys Leu Lys Lys Leu Lys Asn Lys Lys Lys Asn Leu Lys
    690                 695                 700 aaa aaa att aaa tat tat ttg tta tac ctt caa tat ata ata aat ata    2160
Lys Lys Ile Lys Tyr Tyr Leu Leu Tyr Leu Gln Tyr Ile Ile Asn Ile
705                 710                 715                 720 tat aaa gaa gaa tat tat act att tat tat aat ata aaa tta att ata    2208
Tyr Lys Glu Glu Tyr Tyr Thr Ile Tyr Tyr Asn Ile Lys Leu Ile Ile
                725                 730                 735 tca tct ttt att ttt tat tta tta cat ata att ctt aat tta tat aaa    2256
Ser Ser Phe Ile Phe Tyr Leu Leu His Ile Ile Leu Asn Leu Tyr Lys
            740                 745                 750 aat tat agt gtg cgt ata tta tgt aat gca aat tat att ttt tta ata    2304
Asn Tyr Ser Val Arg Ile Leu Cys Asn Ala Asn Tyr Ile Phe Leu Ile
        755                 760                 765 aca tca ttg ggt ttg ttt tct tgt gcc ttg agt ttt tcc tta gaa gat    2352
Thr Ser Leu Gly Leu Phe Ser Cys Ala Leu Ser Phe Ser Leu Glu Asp
    770                 775                 780 ata tta tta aga tat aaa aaa tat aaa ata aat att gat ata aca gta    2400
Ile Leu Leu Arg Tyr Lys Lys Tyr Lys Ile Asn Ile Asp Ile Thr Val
785                 790                 795                 800 ttg gat aag ata aat aaa aat aca ttg ata gtt ttt ctt ttc tcg aat    2448
Leu Asp Lys Ile Asn Lys Asn Thr Leu Ile Val Phe Leu Phe Ser Asn
                805                 810                 815 ata ctt gtg ggc atg ttc aat att cta ttt caa act tta tta tta cct    2496
Ile Leu Val Gly Met Phe Asn Ile Leu Phe Gln Thr Leu Leu Leu Pro
            820                 825                 830 ctt ata ttt gta ata cct ata ttg gta ttt tat tct ttc tta ata ctg    2544
Leu Ile Phe Val Ile Pro Ile Leu Val Phe Tyr Ser Phe Leu Ile Leu
        835                 840                 845 ctt ttt aca aaa tgc tta cca cct tcc ata cgc cat cca aaa aaa aaa    2592
Leu Phe Thr Lys Cys Leu Pro Pro Ser Ile Arg His Pro Lys Lys Lys
    850                 855                 860 aca cat cat gag gaa aag caa aaa aaa gaa tga                        2625
Thr His His Glu Glu Lys Gln Lys Lys Glu *
865                 870

<210> SEQ ID NO 2
<211> LENGTH: 874
<212> TYPE: PRT
<213> ORGANISM: Plasmodium falciparum

<400> SEQUENCE: 2

Met Ser Asn Met Asn Ile Leu Ala Tyr Leu Leu Ile Cys Pro Phe Asn
1               5                   10                  15

Leu Ile Tyr Ile Phe Asp Leu Pro Ser Tyr Ile Pro Glu Leu Asn Lys
            20                  25                  30
```

-continued

```
Lys Leu Glu Asn Asp Glu Val Phe Ile Tyr Gly Lys Glu Ile Arg Lys
        35                  40                  45

Asn Glu Ser Ala Tyr Ser Leu His Tyr Glu Lys Tyr Leu Tyr Glu Leu
 50                  55                  60

Ser Arg Arg Tyr Tyr Glu Ile Ile Leu Lys Tyr Asn Lys Glu Leu Gly
 65                  70                  75                  80

Val Asn Gln Glu Lys Glu Tyr Asn Leu Ile Ile Ser Arg Glu Ile Asp
                 85                  90                  95

Lys Lys Lys Lys Lys Gln Lys Asn Ser Thr Gln Gly Glu Tyr Asn Asn
                100                 105                 110

Asp Asp Asp Asn Asn Trp Lys Leu Phe Gln Ile Tyr Glu Lys Glu Glu
                115                 120                 125

Pro Arg Ser Tyr Glu Leu Ile Arg Val Glu Ile Tyr Lys Lys Asp Ile
        130                 135                 140

Leu Leu Ile Tyr Lys Asn Glu Lys Thr Lys Ser Ser Ile Lys Phe Ile
145                 150                 155                 160

Ile Lys Lys Arg Lys Asp Ile Lys Asn Tyr Phe Ser Leu Cys Tyr Gln
                165                 170                 175

Asn Cys Ile Asn Lys Leu Asp Lys Asn Asp Tyr Asn Ile Leu Lys Ser
            180                 185                 190

Thr Ile Asn Asn Ser Lys Glu Asn Ile Ile Asn Ser Ala Tyr Ile Tyr
            195                 200                 205

Met Tyr Ile Ile Phe Phe Leu Cys Ile Tyr Val Glu Lys Asn Leu
    210                 215                 220

Phe Leu Tyr Phe Pro Ile Leu Leu Gln Lys Tyr Glu Ile Leu Thr Thr
225                 230                 235                 240

Leu Phe Ile Leu Phe Ile Pro Leu Ile Leu Phe Val Phe Phe Tyr Phe
                245                 250                 255

Tyr Phe Thr Ile Ile Lys Leu Ile Cys Ser Cys Leu Val Leu Tyr Val
            260                 265                 270

Thr Phe Gln Leu Ile Tyr Tyr Thr Gln Gly Met Pro Ile Tyr Met Glu
        275                 280                 285

His Ser Ile Leu Lys His Lys Glu Lys Glu Ile Cys Asp Glu Lys
    290                 295                 300

Glu Glu Ile Cys Asp Glu Lys Glu Glu Ile Cys Asp Glu Lys Glu Glu
305                 310                 315                 320

Ile Cys Asp Glu Lys Glu Glu Ile Cys Asp Glu Lys Glu Glu Ile Cys
                325                 330                 335

Asp Glu Lys Glu Glu Ile Leu Asp Lys Lys Lys Ile His Glu Lys
            340                 345                 350

Lys Lys Lys Ile His Asp Lys Lys Glu Glu Ile Asp Glu Lys Lys Lys
        355                 360                 365

Lys Ile His Asp Lys Lys Asp Glu Ser His Lys Asn Glu Asp Ile
    370                 375                 380

Thr Tyr Pro Val Gln Tyr Asn Ile Glu Asn Asp Leu Trp Tyr Ser Ser
385                 390                 395                 400

Lys Asn Val Asp Ile Lys Met Tyr Ser Ser Asn Lys Gly Glu Glu
                405                 410                 415

Tyr Ile Ile Gln Asn Thr Leu Lys His Phe Arg Leu Met Asn Met Cys
            420                 425                 430

Met Thr Tyr Ile Cys Ile Phe Ala Val Asp Phe Tyr Phe Pro Asn
        435                 440                 445

His Phe Cys Lys Ser Tyr Tyr Tyr Gly Asn Thr Leu Met Asp Ile Gly
    450                 455                 460
```

-continued

```
Ile Gly Ala Ser Ile Ser Ser Ala Tyr Ser Gln Glu Ile Lys Lys
465                 470                 475                 480

Phe Thr Tyr Ile Lys Glu Lys Lys Arg Ile Ile Glu Leu Lys His Ile
                    485                 490                 495

Val Leu Phe Ile Leu Gly Ile Ser Arg Phe Ile Gly Ile Tyr Leu Phe
                500                 505                 510

Asn Tyr Asn Tyr Asn Ile Ser Glu Tyr Gly Ile His Trp Asn Phe Phe
                515                 520                 525

Leu Thr Leu Cys Thr Thr Phe Leu Ile Ser Asn Ile Cys Phe Ile Leu
            530                 535                 540

Leu Lys Arg Ile Arg Tyr Ile Phe Leu Phe Ser Ile Ile Ser Ile Ile
545                 550                 555                 560

Leu Phe Glu Ile Ala Ile Tyr Tyr Phe Asp Leu His Asn Tyr Ile Leu
                565                 570                 575

Leu Lys Asn Asp Arg Leu Asn Phe Phe Ser Ser Asn Lys Glu Gly Leu
                580                 585                 590

Phe Asn Ile Ile Gly Ser Val Asn Leu Tyr Leu Phe Ser Phe Ser Leu
                595                 600                 605

Phe Lys Tyr Leu Thr Lys Gln Arg Thr Tyr Ile Thr Thr Ser Asn Ile
                610                 615                 620

Pro Lys Asn Lys Lys Asp Met Asn Asn Ser Met Tyr Ser Lys Asn Gly
625                 630                 635                 640

Asn His Thr Asn Ser Asn Ile Asn Asn Arg Asn His Lys Ile Val Ile
                645                 650                 655

Arg Asn Asn His Ile Asn Lys Tyr Glu Gln Asp Asn Thr Asn Lys Tyr
                660                 665                 670

Ile Asn Lys Gln Ile Asn Asn Lys Asn Lys Leu Asp Glu Glu
                675                 680                 685

Lys Leu Lys Lys Leu Lys Lys Leu Lys Asn Lys Lys Asn Leu Lys
690                 695                 700

Lys Lys Ile Lys Tyr Tyr Leu Leu Tyr Leu Gln Tyr Ile Ile Asn Ile
705                 710                 715                 720

Tyr Lys Glu Glu Tyr Tyr Thr Ile Tyr Tyr Asn Ile Lys Leu Ile Ile
                725                 730                 735

Ser Ser Phe Ile Phe Tyr Leu Leu His Ile Ile Leu Asn Leu Tyr Lys
                740                 745                 750

Asn Tyr Ser Val Arg Ile Leu Cys Asn Ala Asn Tyr Ile Phe Leu Ile
            755                 760                 765

Thr Ser Leu Gly Leu Phe Ser Cys Ala Leu Ser Phe Ser Leu Glu Asp
            770                 775                 780

Ile Leu Leu Arg Tyr Lys Lys Tyr Lys Ile Asn Ile Asp Ile Thr Val
785                 790                 795                 800

Leu Asp Lys Ile Asn Lys Asn Thr Leu Ile Val Phe Leu Phe Ser Asn
                805                 810                 815

Ile Leu Val Gly Met Phe Asn Ile Leu Phe Gln Thr Leu Leu Leu Pro
                820                 825                 830

Leu Ile Phe Val Ile Pro Ile Leu Val Phe Tyr Ser Phe Leu Ile Leu
            835                 840                 845

Leu Phe Thr Lys Cys Leu Pro Pro Ser Ile Arg His Pro Lys Lys Lys
            850                 855                 860

Thr His His Glu Glu Lys Gln Lys Lys Glu
865                 870
```

```
<210> SEQ ID NO 3
<211> LENGTH: 1956
<212> TYPE: DNA
<213> ORGANISM: Plasmodium vivax
<220> FEATURE:
<221> NAME/KEY: CDS
<222> LOCATION: (1)...(1956)

<400> SEQUENCE: 3
```

| | | | | | | | | | | | | | | | | |
|---|---|---|---|---|---|---|---|---|---|---|---|---|---|---|---|---|
| atg | gcg | cat | ttg | aac | ctc | ctc | gtc | tac | ctc | atc | atg | tgc | ccc | ttc | aat | 48 |
| Met | Ala | His | Leu | Asn | Leu | Leu | Val | Tyr | Leu | Ile | Met | Cys | Pro | Phe | Asn | |
| 1 | | | | 5 | | | | | 10 | | | | | 15 | | |
| gtg | agg | cac | atg | ctg | gat | gcg | ccc | agc | ttc | cca | ttc | cgg | tta | gga | agc | 96 |
| Val | Arg | His | Met | Leu | Asp | Ala | Pro | Ser | Phe | Pro | Phe | Arg | Leu | Gly | Ser | |
| | | | 20 | | | | | 25 | | | | | 30 | | | |
| aaa | gca | gca | agt | ggt | gaa | acc | ttc | acg | tat | gga | gcg | act | gca | aga | gag | 144 |
| Lys | Ala | Ala | Ser | Gly | Glu | Thr | Phe | Thr | Tyr | Gly | Ala | Thr | Ala | Arg | Glu | |
| | | 35 | | | | | 40 | | | | | 45 | | | | |
| aac | ctg | ggg | agt | tac | tct | ccc | gca | cat | gac | gag | cta | tac | atg | tta | gag | 192 |
| Asn | Leu | Gly | Ser | Tyr | Ser | Pro | Ala | His | Asp | Glu | Leu | Tyr | Met | Leu | Glu | |
| | 50 | | | | | 55 | | | | | 60 | | | | | |
| tta | gcc | aaa | atg | tac | tat | aaa | att | gtg | tta | aca | tat | aag | aag | gat | gtt | 240 |
| Leu | Ala | Lys | Met | Tyr | Tyr | Lys | Ile | Val | Leu | Thr | Tyr | Lys | Lys | Asp | Val | |
| 65 | | | | 70 | | | | | 75 | | | | | 80 | | |
| agg | aaa | gga | cag | gag | gag | agt | tac | aac | ttg | gtg | gta | ggc | tcc | ttt | ggg | 288 |
| Arg | Lys | Gly | Gln | Glu | Glu | Ser | Tyr | Asn | Leu | Val | Val | Gly | Ser | Phe | Gly | |
| | | | | 85 | | | | | 90 | | | | | 95 | | |
| aag | gaa | gcc | aaa | ggg | gag | gtc | tcc | ctc | caa | aga | gtt | ctc | atc | aca | aat | 336 |
| Lys | Glu | Ala | Lys | Gly | Glu | Val | Ser | Leu | Gln | Arg | Val | Leu | Ile | Thr | Asn | |
| | | | 100 | | | | | 105 | | | | | 110 | | | |
| gat | gcc | gtg | tac | ctg | tcg | tac | cag | gat | gtg | caa | aac | gaa | cgt | ggg | atc | 384 |
| Asp | Ala | Val | Tyr | Leu | Ser | Tyr | Gln | Asp | Val | Gln | Asn | Glu | Arg | Gly | Ile | |
| | | 115 | | | | | 120 | | | | | 125 | | | | |
| caa | gtt | aag | ata | aaa | agg | ggg | gaa | ata | tct | tcc | tat | tta | gac | ctc | cta | 432 |
| Gln | Val | Lys | Ile | Lys | Arg | Gly | Glu | Ile | Ser | Ser | Tyr | Leu | Asp | Leu | Leu | |
| | 130 | | | | | 135 | | | | | 140 | | | | | |
| tcg | tgg | gat | tct | tgt | ttg | tat | aag | ctt | aac | tca | gac | gat | tat | aat | tta | 480 |
| Ser | Trp | Asp | Ser | Cys | Leu | Tyr | Lys | Leu | Asn | Ser | Asp | Asp | Tyr | Asn | Leu | |
| 145 | | | | 150 | | | | | 155 | | | | | 160 | | |
| atg | aag | agc | gca | tcg | gat | cat | agc | aag | cca | atg | gtg | gtc | agc | aca | tac | 528 |
| Met | Lys | Ser | Ala | Ser | Asp | His | Ser | Lys | Pro | Met | Val | Val | Ser | Thr | Tyr | |
| | | | | 165 | | | | | 170 | | | | | 175 | | |
| cac | ata | tac | atg | ctg | ctg | ctg | gtg | ttt | tct | ctt | tgc | act | tac | gtg | gag | 576 |
| His | Ile | Tyr | Met | Leu | Leu | Leu | Val | Phe | Ser | Leu | Cys | Thr | Tyr | Val | Glu | |
| | | | 180 | | | | | 185 | | | | | 190 | | | |
| aag | agc | ctc | ctg | ctt | gaa | ttc | cct | gcg | ttg | aaa | aag | tgc | caa | gta | ttt | 624 |
| Lys | Ser | Leu | Leu | Leu | Glu | Phe | Pro | Ala | Leu | Lys | Lys | Cys | Gln | Val | Phe | |
| | | 195 | | | | | 200 | | | | | 205 | | | | |
| cta | acc | cta | tgt | ttg | gtg | tac | tgc | ccg | ata | atc | agt | tac | ctt | ttt | ttt | 672 |
| Leu | Thr | Leu | Cys | Leu | Val | Tyr | Cys | Pro | Ile | Ile | Ser | Tyr | Leu | Phe | Phe | |
| | 210 | | | | | 215 | | | | | 220 | | | | | |
| ttt | tac | tcc | cat | gtg | agc | cta | ctt | ggg | gtg | tta | ctc | gtc | tat | gtg | ttt | 720 |
| Phe | Tyr | Ser | His | Val | Ser | Leu | Leu | Gly | Val | Leu | Leu | Val | Tyr | Val | Phe | |
| 225 | | | | 230 | | | | | 235 | | | | | 240 | | |
| ttt | tgc | ggg | ctc | ttc | agg | ggc | gtc | tct | tgc | aga | agg | ggg | ggg | cag | cac | 768 |
| Phe | Cys | Gly | Leu | Phe | Arg | Gly | Val | Ser | Cys | Arg | Arg | Gly | Gly | Gln | His | |
| | | | | 245 | | | | | 250 | | | | | 255 | | |
| atg | ggg | gag | caa | acg | ggc | caa | cac | acg | ggc | gat | tgg | cac | acc | atc | cgc | 816 |
| Met | Gly | Glu | Gln | Thr | Gly | Gln | His | Thr | Gly | Asp | Trp | His | Thr | Ile | Arg | |
| | | | 260 | | | | | 265 | | | | | 270 | | | |
| ggc | aac | cca | caa | ggt | gat | gat | acg | caa | gag | gag | aga | cgc | aag | tgt | ttg | 864 |
| Gly | Asn | Pro | Gln | Gly | Asp | Asp | Thr | Gln | Glu | Glu | Arg | Arg | Lys | Cys | Leu | |

-continued

```
                275                 280                 285
gtc cat atg agg cta gcc aac ctg tgc atc acc tac ata tgc ata ttc      912
Val His Met Arg Leu Ala Asn Leu Cys Ile Thr Tyr Ile Cys Ile Phe
    290                 295                 300 gct gtg gac ttt tat ttt ttc cca agg caa ttt tcc aag tct ttt ttt      960
Ala Val Asp Phe Tyr Phe Phe Pro Arg Gln Phe Ser Lys Ser Phe Phe
305                 310                 315                 320 ttt ggt aac act ttg atg gat tta ggg gtg ggg ggg tgc atc aca tcg     1008
Phe Gly Asn Thr Leu Met Asp Leu Gly Val Gly Gly Cys Ile Thr Ser
                325                 330                 335 agc gcg tat tct cta aac agt aaa aag ctc cat tct gcg aac cgc aag     1056
Ser Ala Tyr Ser Leu Asn Ser Lys Lys Leu His Ser Ala Asn Arg Lys
        340                 345                 350 gga cac cta atc gat tgg aag cat ttc att tta ttt ttc ctt gga ata     1104
Gly His Leu Ile Asp Trp Lys His Phe Ile Leu Phe Phe Leu Gly Ile
            355                 360                 365 gct aga tac att gca gtg aag ctt ttc aat tat aat tac agc tta act     1152
Ala Arg Tyr Ile Ala Val Lys Leu Phe Asn Tyr Asn Tyr Ser Leu Thr
370                 375                 380 gag tat ggg atg cac tgg aat ttt ttt ctt act ctc ttt ttt act ctc     1200
Glu Tyr Gly Met His Trp Asn Phe Phe Leu Thr Leu Phe Phe Thr Leu
385                 390                 395                 400 cta act tgt aac gcc cta ctc tgc ttg ata aga ggg gtt aaa cgc acc     1248
Leu Thr Cys Asn Ala Leu Leu Cys Leu Ile Arg Gly Val Lys Arg Thr
                405                 410                 415 ttt cac ctg agc tgc gtc ctc atc tgt ttg tat gaa att ata att tgg     1296
Phe His Leu Ser Cys Val Leu Ile Cys Leu Tyr Glu Ile Ile Ile Trp
            420                 425                 430 cgc ctg gac att acg agt tat tta gtg gtt gac gag gca gaa cgg agc     1344
Arg Leu Asp Ile Thr Ser Tyr Leu Val Val Asp Glu Ala Glu Arg Ser
        435                 440                 445 ggc ttt ttt tcg cag aac aga gag ggc ctt atg aac gtc atc ggg tcc     1392
Gly Phe Phe Ser Gln Asn Arg Glu Gly Leu Met Asn Val Ile Gly Ser
450                 455                 460 gtc aat ttg tac ctc ttt tcg ttt tcg cta tgg aat ggc tat gtg ttt     1440
Val Asn Leu Tyr Leu Phe Ser Phe Ser Leu Trp Asn Gly Tyr Val Phe
465                 470                 475                 480 ccg gat gag ggg cag cag tgg gag cga gga aag gcg gcg cga aga ccg     1488
Pro Asp Glu Gly Gln Gln Trp Glu Arg Gly Lys Ala Ala Arg Arg Pro
                485                 490                 495 gat gag gcg gcg cga acg ccg ggg gag gga cat ggc cag cgc tcc cct     1536
Asp Glu Ala Ala Arg Thr Pro Gly Glu Gly His Gly Gln Arg Ser Pro
            500                 505                 510 gtc cgc ctc acc ctg aag ttg ctt gcc ctg tcc ctc ctc ttc cac ctg     1584
Val Arg Leu Thr Leu Lys Leu Leu Ala Leu Ser Leu Leu Phe His Leu
        515                 520                 525 ctg cac ctg ctg ttg aat tac tac cga aat tac agt gtg cgc atc ctt     1632
Leu His Leu Leu Leu Asn Tyr Tyr Arg Asn Tyr Ser Val Arg Ile Leu
530                 535                 540 tgc aac gcg aac tac ata tgt gtt gtc tcc tcc gtg agt ctc ttc gcg     1680
Cys Asn Ala Asn Tyr Ile Cys Val Val Ser Ser Val Ser Leu Phe Ala
545                 550                 555                 560 gct gcc ctg agc tac ctc gta gag aag gta ctc ctc cgc gag aag acc     1728
Ala Ala Leu Ser Tyr Leu Val Glu Lys Val Leu Leu Arg Glu Lys Thr
                565                 570                 575 acc acc atc cca gtt ttg caa caa atg aac cgg cac tcc ctg gca gtg     1776
Thr Thr Ile Pro Val Leu Gln Gln Met Asn Arg His Ser Leu Ala Val
            580                 585                 590 ttc ctc ttt tgc aac gta aca atg ggc act ttc aac ctc ctc ttt cag     1824
Phe Leu Phe Cys Asn Val Thr Met Gly Thr Phe Asn Leu Leu Phe Gln
```

```
                    595                 600                 605
tct ctc ttg ttt ccc cta ttt ttt gcg tgc ctc gtt ttg gcg gcg tac    1872
Ser Leu Leu Phe Pro Leu Phe Phe Ala Cys Leu Val Leu Ala Ala Tyr
610                 615                 620 tcc tat ggc atg ttg cgc ttc gcc tcc ctg ttg ccc ggc ccc gcg cag    1920
Ser Tyr Gly Met Leu Arg Phe Ala Ser Leu Leu Pro Gly Pro Ala Gln
625                 630                 635                 640 ggg gag aag gga gag aag cgg gag aag cag caa taa                    1956
Gly Glu Lys Gly Glu Lys Arg Glu Lys Gln Gln *
                    645                 650

<210> SEQ ID NO 4
<211> LENGTH: 651
<212> TYPE: PRT
<213> ORGANISM: Plasmodium vivax

<400> SEQUENCE: 4

Met Ala His Leu Asn Leu Leu Val Tyr Leu Ile Met Cys Pro Phe Asn
1               5                   10                  15

Val Arg His Met Leu Asp Ala Pro Ser Phe Pro Phe Arg Leu Gly Ser
                20                  25                  30

Lys Ala Ala Ser Gly Glu Thr Phe Thr Tyr Gly Ala Thr Ala Arg Glu
            35                  40                  45

Asn Leu Gly Ser Tyr Ser Pro Ala His Asp Glu Leu Tyr Met Leu Glu
        50                  55                  60

Leu Ala Lys Met Tyr Tyr Lys Ile Val Leu Thr Tyr Lys Lys Asp Val
65                  70                  75                  80

Arg Lys Gly Gln Glu Glu Ser Tyr Asn Leu Val Val Gly Ser Phe Gly
                85                  90                  95

Lys Glu Ala Lys Gly Glu Val Ser Leu Gln Arg Val Leu Ile Thr Asn
            100                 105                 110

Asp Ala Val Tyr Leu Ser Tyr Gln Asp Val Gln Asn Glu Arg Gly Ile
        115                 120                 125

Gln Val Lys Ile Lys Arg Gly Glu Ile Ser Ser Tyr Leu Asp Leu Leu
130                 135                 140

Ser Trp Asp Ser Cys Leu Tyr Lys Leu Asn Ser Asp Asp Tyr Asn Leu
145                 150                 155                 160

Met Lys Ser Ala Ser Asp His Ser Lys Pro Met Val Val Ser Thr Tyr
                165                 170                 175

His Ile Tyr Met Leu Leu Leu Val Phe Ser Leu Cys Thr Tyr Val Glu
            180                 185                 190

Lys Ser Leu Leu Leu Glu Phe Pro Ala Leu Lys Lys Cys Gln Val Phe
        195                 200                 205

Leu Thr Leu Cys Leu Val Tyr Cys Pro Ile Ile Ser Tyr Leu Phe Phe
210                 215                 220

Phe Tyr Ser His Val Ser Leu Leu Gly Val Leu Leu Val Tyr Val Phe
225                 230                 235                 240

Phe Cys Gly Leu Phe Arg Gly Val Ser Cys Arg Arg Gly Gly Gln His
                245                 250                 255

Met Gly Glu Gln Thr Gly Gln His Thr Gly Asp Trp His Thr Ile Arg
            260                 265                 270

Gly Asn Pro Gln Gly Asp Asp Thr Gln Glu Glu Arg Arg Lys Cys Leu
        275                 280                 285

Val His Met Arg Leu Ala Asn Leu Cys Ile Thr Tyr Ile Cys Ile Phe
290                 295                 300

Ala Val Asp Phe Tyr Phe Phe Pro Arg Gln Phe Ser Lys Ser Phe Phe
```

```
                305                 310                 315                 320
Phe Gly Asn Thr Leu Met Asp Leu Gly Val Gly Gly Cys Ile Thr Ser
                    325                 330                 335

Ser Ala Tyr Ser Leu Asn Ser Lys Lys Leu His Ser Ala Asn Arg Lys
                340                 345                 350

Gly His Leu Ile Asp Trp Lys His Phe Ile Leu Phe Phe Leu Gly Ile
            355                 360                 365

Ala Arg Tyr Ile Ala Val Lys Leu Phe Asn Tyr Asn Tyr Ser Leu Thr
        370                 375                 380

Glu Tyr Gly Met His Trp Asn Phe Phe Leu Thr Leu Phe Phe Thr Leu
385                 390                 395                 400

Leu Thr Cys Asn Ala Leu Leu Cys Leu Ile Arg Gly Val Lys Arg Thr
                405                 410                 415

Phe His Leu Ser Cys Val Leu Ile Cys Leu Tyr Glu Ile Ile Ile Trp
                    420                 425                 430

Arg Leu Asp Ile Thr Ser Tyr Leu Val Val Asp Glu Ala Glu Arg Ser
                435                 440                 445

Gly Phe Phe Ser Gln Asn Arg Glu Gly Leu Met Asn Val Ile Gly Ser
            450                 455                 460

Val Asn Leu Tyr Leu Phe Ser Phe Ser Leu Trp Asn Gly Tyr Val Phe
465                 470                 475                 480

Pro Asp Glu Gly Gln Gln Trp Glu Arg Gly Lys Ala Ala Arg Arg Pro
                485                 490                 495

Asp Glu Ala Ala Arg Thr Pro Gly Gly His Gly Gln Arg Ser Pro
                500                 505                 510

Val Arg Leu Thr Leu Lys Leu Leu Ala Leu Ser Leu Leu Phe His Leu
            515                 520                 525

Leu His Leu Leu Leu Asn Tyr Tyr Arg Asn Tyr Ser Val Arg Ile Leu
        530                 535                 540

Cys Asn Ala Asn Tyr Ile Cys Val Val Ser Ser Val Ser Leu Phe Ala
545                 550                 555                 560

Ala Ala Leu Ser Tyr Leu Val Glu Lys Val Leu Leu Arg Glu Lys Thr
                565                 570                 575

Thr Thr Ile Pro Val Leu Gln Gln Met Asn Arg His Ser Leu Ala Val
                    580                 585                 590

Phe Leu Phe Cys Asn Val Thr Met Gly Thr Phe Asn Leu Leu Phe Gln
                595                 600                 605

Ser Leu Leu Phe Pro Leu Phe Phe Ala Cys Leu Val Leu Ala Ala Tyr
            610                 615                 620

Ser Tyr Gly Met Leu Arg Phe Ala Ser Leu Leu Pro Gly Pro Ala Gln
625                 630                 635                 640

Gly Glu Lys Gly Glu Lys Arg Glu Lys Gln Gln
                    645                 650

<210> SEQ ID NO 5
<211> LENGTH: 2625
<212> TYPE: DNA
<213> ORGANISM: Artificial Sequence
<220> FEATURE:
<223> OTHER INFORMATION: Artificially synthesized sequence

<400> SEQUENCE: 5
atgagtaaca tgaacatcct ggcctacctg ctgatctgtc cattcaacct gatctacatc      60
ttcgacctgc ctagctacat ccctgagcta aacaagaagc tggagaacga cgaagtcttc     120
atctacggta aggagatccg taagaacgaa tccgcatact ctctacacta cgagaagtac     180
```

```
ctatacgaat tgtcacgaag atactacgag atcatcctga agtacaacaa ggagttggga      240
gtcaaccaag agaaggaata caacctgatt atctccagag agatcgataa gaagaagaag      300
aagcagaaga atagtaccca gggtgaatac aataacgacg atgataacaa ttggaagttg      360
ttccagattt acgagaagga agaacctagg agctatgaat tgatcagggt agagatatac      420
aagaaggaca ttctgttgat ctacaagaat gagaagacga agtcctctat caagttcatt      480
atcaagaagc gtaaggatat caagaattac ttctccttgt gttaccagaa ctgtatcaat      540
aagctggaca agaatgatta caacatcttg aagtctacca tcaacaattc caaggaaaac      600
attatcaact ctgcatacat ttacatgtac attatcttct tcttcctgtg catatacgtc      660
gagaagaacc tgttcttgta cttcccaata ttgcttcaga agtatgagat tctcactacg      720
ttgttcatcc tcttcatccc attgatccta ttcgtattct tctatttcta cttcacgatt      780
atcaagctga tttgctcatg cttagtccta tacgtgactt tccagttgat ctactatacg      840
cagggaatgc ctatttacat ggaacatagt attctcaagc acaaggagaa ggaagagatt      900
tgcgatgaga aggaggaaat ctgtgatgaa aaggaagaga tttgcgatga aaggaagag       960 atttgcgatg agaaggaaga gatttgtgat gagaaggaag aaatctgcga tgagaaagaa     1020
gaaatccttg ataagaagaa gaagatccac gagaagaaga agaagatcca tgataagaaa     1080
gaggaaatcg atgagaagaa gaagaagatt catgacaaaa aggacgaaag tcatgataag     1140
aacgaggaca ttacgtatcc agtccagtac aatatcgaga atgacctatg gtattcatcc     1200
aagaacgtgg acatcaagat gtattcatcc agcaacaagg gtgaagaata cattatccag     1260
aacacgttga acatttccg attgatgaac atgtgtatga cgtacatttg tatcttcgct      1320
gttgacttct acttcttccc taaccatttc tgcaagtcct actattacgg aaatacgttg     1380
atggacattg gaatcggtgc atccatttct tccagtgcat actcgcagga gatcaagaag     1440
ttcacgtaca ttaaggagaa gaaacgaatt atcgagttga acatatcgt gttattcatt      1500 ctgggaatta gcagatttat cggtatctac ctattcaact ataactacaa catttctgag     1560 tatgaatcc attggaactt ctttcttacg ctatgtacaa cctttctgat tagcaacatt      1620
tgtttcatcc tcctcaagag gattcgttat atcttcctat tcagtattat ctcgatcatc     1680
ttattcgaaa tcgctatttta ctacttcgat ctacataatt acatcctcct gaagaatgac     1740
cgtttaaact tcttctcttc taacaaggag ggtctattca acattatcgg ttccgtgaac     1800
ctttatttgt tcagtttctc actcttcaag taccttacga agcagcgtac gtatatcacg     1860
acgtccaata tccctaagaa caagaaagat atgaataact caatgtattc gaagaatgga     1920
aaccatacta attcgaatat caacaaccgt aaccataaga tcgtcatccg taataaccac     1980
attaacaagt atgagcagga caacacgaac aagtacatca acaagcaaat caataacaac     2040
aagaacaaat tggatgagga agagaagctg aagaaactca agaagcttaa gaataagaag     2100
aagaacctca agaagaaaat caagtactat ctattgtacc ttcagtatat catcaacatc     2160
tacaaggagg aatactatac gatctactat aacatcaagc taatcatttc gtcgttatata    2220 ttctacctcc ttcacataat ccttaatctg tacaagaact actctgtgcg tattctgtgt     2280
aatgcaaact acatcttcct gattacgagt ctgggtctgt tctcctgtgc attatccttc     2340
tccctggagg acatcctact ccgttataag aaatacaaga tcaatatcga tattactgtg     2400
ctagataaga ttaacaagaa caccttaatc gtgttcctgt ttagtaatat cctagtggga     2460
atgttcaaca tcctgttcca aactttgctc ctaccactga tattcgttat ccctattcta     2520
gtattctaca gcttcttgat cctgctgttc accaagtgtt tgccaccttc tatccgacat     2580
```

```
cctaagaaga agacgcatca cgaagagaag cagaagaaag agtga               2625

<210> SEQ ID NO 6
<211> LENGTH: 2010
<212> TYPE: DNA
<213> ORGANISM: Plasmodium falciparum

<400> SEQUENCE: 6
atgtgcacta caaaaaatga agacaataat aaagtgaatt atctgtatct catttattat    60
aataatatac ctatatttaa aaaaaaaagt ggaaatgaac aaaacataag tgcgctattt   120
attttatatg atgtaaaaaa gtatgtgtat aatatggttc atgatcacgt aaatacatta   180
gtcctagaag cttttagaag agaagacata ataaaaaaaa taaagtaaa agaaaaacaa    240 aataataatg ataaaaataa agaaagtaat attgaaaaag ataaaaatga acaaaccaaa   300
tttacagata tatatgatac aaatagtaag agtgacaaag atatacaaaa gaataatatg   360
aacgatggtg atagtaataa taaaaatagt agtttatttta ttgatccttt tgaaagtgat   420
tcatatgaaa agaataattt tagtaatgaa aaatgtgctt ccaaaatgt cgataaatca    480 aaaaaagata agaacatat atattctgaa atattactc ctagtagtag taataataat    540
aatgataata ataagaaaa tgattgtgat aaggaacaat tagataaata taataaagat   600
aaagaaaata aattaaaatt aaatgataag gatgaatata tttcttctcaa ttttattgaa   660 gataaattaa ccgaatcatt tcatatgaat caaataattc atttaattaa taaaaaatgt   720
gtatttacca aatgcctaga aaattataaa atagatatt ttgtactgaa aaagaagag    780 attttaaaaa aaaaaaaaaa gcaaaaaaaa atgtctatat tttcatatat tgtatcaatc   840 atattattt ttacatatat catatcacttt ataaatagtt gtttatatta tataaatatgt   900 acaccaaaat tgttcagtga atatatattt tcaaaaaaat gtgatggata tctgcagaat   960
tcggcttacc ctaaatttat atttccttct gaatggcata atatattccg cagcttcatg  1020
aaaaataaac aaaaaccatc tgaatattat aaatatagag aaatcttatt aattcgtatt  1080
atcaatttaa taatcgatat tttcttggga ttttctgatat ttttactact ttattttaac  1140
gtaataaacc tacattatat atcagagaag gctcaaatat tttatggaac cagtactta   1200 acttctatct ggtaccctt gttacagaat ccattaggat ttaaattaaa taataatttt   1260
acgtctttca ttggtagcat ccttgtttcg atattagaca aatgggattt attttacaaat  1320 accatcctg tgaataatag tacagttttg aattttgttg gatatacatc actgctgggt  1380
tttttctttt ttttgtcttt tgttattgat tatttgagat tcgtaacagc acatgttacc  1440
attatttatt tattttttgaa aaaaatatgt accctttttc ataaaatat gtattcctta   1500 tacctattat tcaatgggaa aaaatggaac atactaaaac taagagttga tacaaattac  1560
tactcaaatg aagaagtact tttaggaacc atattattta ccatttttaat tttttttgtac  1620 cctaccattt ttgttcttgt tttggttttt ggtcttatat atcttataat aaatagaatt  1680 ataaccttt tgtgtgttat ggagaaaata attttgtaca cccctttcta tattttcttt   1740
attcaaccga attgtaataa atatattagt aagggtttca agtttacaaa atatgaagtt  1800
ggggaacatg aactgttaaa aaggtatccg actaacagct acttgttgct agaaaagatt  1860
cattttttat tttttgataa aataaaattg tttataaata ttttccttta ttttaaaaac   1920
ctcgagtcaa tgtcatcata ttcatatata tttatttctt tttgtttttg tcttttaaaa   1980
aaaaaatata tatatatata tataatataa                                      2010
```

-continued

```
<210> SEQ ID NO 7
<211> LENGTH: 669
<212> TYPE: PRT
<213> ORGANISM: Plasmodium falciparum

<400> SEQUENCE: 7

Met Cys Thr Thr Lys Asn Glu Asp Asn Asn Lys Val Asn Tyr Leu Tyr
  1               5                  10                  15

Leu Ile Tyr Tyr Asn Asn Ile Pro Ile Phe Lys Lys Ser Gly Asn
             20                  25                  30

Glu Gln Asn Ile Ser Ala Leu Phe Ile Leu Tyr Asp Val Lys Lys Tyr
             35                  40                  45

Val Tyr Asn Met Val His Asp His Val Asn Thr Leu Val Leu Glu Ala
         50                  55                  60

Phe Arg Arg Glu Asp Ile Ile Lys Lys Ile Lys Val Lys Glu Lys Gln
 65                  70                  75                  80

Asn Asn Asn Asp Lys Asn Lys Glu Ser Asn Ile Glu Lys Asp Lys Asn
                 85                  90                  95

Glu Gln Thr Lys Phe Thr Asp Ile Tyr Asp Thr Asn Ser Lys Ser Asp
            100                 105                 110

Lys Asp Ile Gln Lys Asn Asn Met Asn Asp Gly Asp Ser Asn Asn Lys
            115                 120                 125

Asn Ser Ser Leu Phe Ile Asp Pro Phe Glu Ser Asp Ser Tyr Glu Lys
        130                 135                 140

Asn Asn Phe Ser Asn Glu Lys Cys Ala Phe Gln Asn Val Asp Lys Ser
145                 150                 155                 160

Lys Lys Asp Lys Glu His Ile Tyr Ser Glu Asn Ile Thr Pro Ser Ser
                165                 170                 175

Ser Asn Asn Asn Asn Asp Asn Asn Lys Glu Asn Asp Cys Asp Lys Glu
            180                 185                 190

Gln Leu Asp Lys Tyr Asn Lys Asp Lys Glu Asn Lys Leu Lys Leu Asn
        195                 200                 205

Asp Lys Asp Glu Tyr Ile Ser Phe Asn Phe Ile Glu Asp Lys Leu Thr
    210                 215                 220

Glu Ser Phe His Met Asn Gln Ile Ile His Leu Ile Asn Lys Lys Cys
225                 230                 235                 240

Val Phe Thr Lys Cys Leu Glu Asn Tyr Lys Asn Arg Tyr Phe Val Leu
                245                 250                 255

Lys Lys Glu Glu Ile Leu Lys Lys Lys Lys Gln Lys Lys Met Ser
            260                 265                 270

Ile Phe Ser Tyr Ile Val Ser Ile Ile Leu Phe Phe Thr Tyr Ile Ile
        275                 280                 285

Ser Leu Ile Asn Ser Cys Leu Tyr Tyr Ile Ile Cys Thr Pro Lys Leu
    290                 295                 300

Phe Ser Glu Tyr Ile Phe Ser Lys Lys Cys Asp Gly Tyr Leu Gln Asn
305                 310                 315                 320

Ser Ala Tyr Pro Lys Phe Ile Phe Pro Ser Glu Trp His Asn Ile Phe
                325                 330                 335

Arg Ser Phe Met Lys Asn Lys Gln Asn Pro Ser Glu Tyr Tyr Lys Tyr
            340                 345                 350

Arg Glu Ile Leu Leu Ile Arg Ile Ile Asn Leu Ile Ile Asp Ile Phe
        355                 360                 365

Leu Gly Phe Leu Ile Phe Leu Leu Tyr Phe Asn Val Ile Asn Leu
    370                 375                 380

His Tyr Ile Ser Glu Lys Ala Gln Ile Phe Tyr Gly Thr Ser Thr Leu
```

```
                385                 390                 395                 400
Thr Ser Ile Leu Gly Thr Leu Leu Gln Asn Pro Leu Gly Phe Lys Leu
                405                 410                 415
Asn Asn Asn Phe Thr Ser Phe Ile Gly Ser Ile Leu Val Ser Ile Leu
                420                 425                 430
Asp Lys Trp Asp Leu Phe Thr Asn Thr Ile Pro Val Asn Asn Ser Thr
                435                 440                 445
Val Leu Asn Phe Val Gly Tyr Thr Ser Leu Leu Gly Phe Ser Phe Phe
            450                 455                 460
Leu Ser Phe Val Ile Asp Tyr Leu Arg Phe Val Thr Ala His Val Thr
465                 470                 475                 480
Ile Ile Tyr Leu Phe Leu Lys Lys Ile Cys Thr Leu Phe His Lys Asn
                485                 490                 495
Met Tyr Ser Leu Tyr Leu Leu Phe Asn Gly Lys Lys Trp Asn Ile Leu
                500                 505                 510
Lys Leu Arg Val Asp Thr Asn Tyr Tyr Ser Asn Glu Glu Val Leu Leu
                515                 520                 525
Gly Thr Ile Leu Phe Thr Ile Leu Ile Phe Leu Tyr Pro Thr Ile Phe
            530                 535                 540
Val Leu Val Leu Val Phe Gly Leu Ile Tyr Leu Ile Ile Asn Arg Ile
545                 550                 555                 560
Ile Tyr Leu Leu Cys Val Met Glu Lys Ile Ile Leu Tyr Thr Pro Phe
                565                 570                 575
Tyr Ile Phe Phe Ile Gln Pro Asn Cys Asn Lys Tyr Ile Ser Lys Gly
                580                 585                 590
Phe Lys Phe Thr Lys Tyr Glu Val Gly Glu His Glu Leu Leu Lys Arg
                595                 600                 605
Tyr Pro Thr Asn Ser Tyr Leu Leu Glu Lys Ile His Phe Leu Phe
            610                 615                 620
Phe Asp Lys Ile Lys Leu Phe Ile Asn Ile Phe Leu Tyr Phe Lys Asn
625                 630                 635                 640
Leu Glu Ser Met Ser Ser Tyr Ser Tyr Ile Phe Ile Ser Phe Cys Phe
                645                 650                 655
Cys Leu Leu Lys Lys Lys Tyr Ile Tyr Ile Tyr Ile Ile
                660                 665

<210> SEQ ID NO 8
<211> LENGTH: 1482
<212> TYPE: DNA
<213> ORGANISM: Plasmodium falciparum

<400> SEQUENCE: 8
atggggataa aaattataat ttatatattt tttctatcgt gggcgaaatg ggtgtgtggg      60
tctgttaatt ttaccgggtt tgataacaaa aatatgatag gtaagcacgt ggaactagaa     120
gggaggtata aaaggaata tatagatagg ttttttttag aagaattaag aaaacacaat      180
tatatgaata acaatgttat attattaagt acatcaagac attattttaa ttatagacat     240
accactaatt tattgattgc atataaatat cttaaatatt tcggtgatac tatggataag     300
aatattttat taatgattcc atttgatcaa gcttgtgatt gtaggaatat aagagaaggt     360
caaatatttc gagaatatga attatttcct agtagtcata taaagaaac aaaaatagaa      420 aatataaatt tatatgagaa tttaaatatt gattataaaa ataataatgt acgtgatgaa      480 caattagaa gagtacttag acatagatat gatgcttta cacctaaaaa aaatagatta       540
tataataatg gaaataatga gaaaaattta tttctttata tgaccggaca tggtggtgtg     600
```

```
aatttttaa aaattcaaga atttaatatt attagttctt ctgaatttaa tatatatata    660
caagaattac ttatcaaaaa ttttataaa tatatattcg taattattga tacgtgtcaa    720
ggatatagtt tttatgatga tattctaaat tttgtatata aaaaaaaaat taataatatc    780
ttctttttat catcttctaa aagaaatgaa aatagttata gtttattttc cagtagttat    840
ttaagcgttt caacggtcga cagatttaca taccatttt ttaattatct tcaacaaata    900
cataaaatat atgaaaaaga accatctaaa aatataaaag cctttcatt atataacatt    960 ttaaattatt taaaaacaca acatattatg tcagaaccta ctacaaataa ttctaaattt   1020
aattcgtcca ttttttaca tgataaaaat attcttttct tcaattctaa tttgttaatt   1080
atacataaag atgatgtttc tataatatat caagataaac aaacacacaa tcacaaatat   1140
atatgtttgg ataatctatc taatgtggt catataaaaa ataatgtaca taaaaaaatg    1200
caaactctat atgaacaaac gttatattat aataataatc aacagaattt cttttctaat   1260
catatgtcta atttacaga ttatttttt acacatgata tatataatat atataatata    1320
tataatgtat ataatatata taatgtatat aatatatata atgtatatga tatatataat   1380
gtatattctt ttcttatatt attgctctct ttatttttta ttatgtgttc tcttcttaca   1440
tattatattg tttttttac agaaaaggct aaaatgacat aa                      1482

<210> SEQ ID NO 9
<211> LENGTH: 493
<212> TYPE: PRT
<213> ORGANISM: Plasmodium falciparum

<400> SEQUENCE: 9

Met Gly Ile Lys Ile Ile Ile Tyr Ile Phe Phe Leu Ser Trp Ala Lys
  1               5                  10                  15

Trp Val Cys Gly Ser Val Asn Phe Thr Gly Phe Asp Asn Lys Asn Met
                 20                  25                  30

Ile Gly Lys His Val Glu Leu Glu Gly Arg Tyr Lys Lys Glu Tyr Ile
             35                  40                  45

Asp Arg Phe Phe Leu Glu Glu Leu Arg Lys His Asn Tyr Met Asn Asn
         50                  55                  60

Asn Val Ile Leu Leu Ser Thr Ser Arg His Tyr Phe Asn Tyr Arg His
 65                  70                  75                  80

Thr Thr Asn Leu Leu Ile Ala Tyr Lys Tyr Leu Lys Tyr Phe Gly Asp
                 85                  90                  95

Thr Met Asp Lys Asn Ile Leu Leu Met Ile Pro Phe Asp Gln Ala Cys
            100                 105                 110

Asp Cys Arg Asn Ile Arg Glu Gly Gln Ile Phe Arg Glu Tyr Glu Leu
        115                 120                 125

Phe Pro Ser Ser His Asn Lys Glu Thr Lys Ile Glu Asn Ile Asn Leu
    130                 135                 140

Tyr Glu Asn Leu Asn Ile Asp Tyr Lys Asn Asn Val Arg Asp Glu
145                 150                 155                 160

Gln Ile Arg Arg Val Leu Arg His Arg Tyr Asp Ala Phe Thr Pro Lys
                165                 170                 175

Lys Asn Arg Leu Tyr Asn Asn Gly Asn Asn Glu Lys Asn Leu Phe Leu
            180                 185                 190

Tyr Met Thr Gly His Gly Gly Val Asn Phe Leu Lys Ile Gln Glu Phe
        195                 200                 205

Asn Ile Ile Ser Ser Ser Glu Phe Asn Ile Tyr Ile Gln Glu Leu Leu
    210                 215                 220
```

-continued

```

Ile Lys Asn Phe Tyr Lys Tyr Ile Phe Val Ile Ile Asp Thr Cys Gln
225                 230                 235                 240

Gly Tyr Ser Phe Tyr Asp Asp Ile Leu Asn Phe Val Tyr Lys Lys Lys
                245                 250                 255

Ile Asn Asn Ile Phe Phe Leu Ser Ser Ser Lys Arg Asn Glu Asn Ser
            260                 265                 270

Tyr Ser Leu Phe Ser Ser Ser Tyr Leu Ser Val Ser Thr Val Asp Arg
        275                 280                 285

Phe Thr Tyr His Phe Phe Asn Tyr Leu Gln Gln Ile His Lys Ile Tyr
    290                 295                 300

Glu Lys Glu Pro Ser Lys Asn Ile Lys Ala Phe Ser Leu Tyr Asn Ile
305                 310                 315                 320

Leu Asn Tyr Leu Lys Thr Gln His Ile Met Ser Glu Pro Thr Thr Asn
                325                 330                 335

Asn Ser Lys Phe Asn Ser Ser Ile Phe Leu His Asp Lys Asn Ile Leu
            340                 345                 350

Phe Phe Asn Ser Asn Leu Leu Ile Ile His Lys Asp Asp Val Ser Ile
        355                 360                 365

Ile Tyr Gln Asp Lys Gln Thr His Asn His Lys Tyr Ile Cys Leu Asp
    370                 375                 380

Asn Leu Ser Lys Cys Gly His Ile Lys Asn Asn Val His Lys Lys Met
385                 390                 395                 400

Gln Thr Leu Tyr Glu Gln Thr Leu Tyr Tyr Asn Asn Asn Gln Gln Asn
                405                 410                 415

Phe Phe Ser Asn His Met Ser Asn Phe Thr Asp Tyr Phe Phe Thr His
            420                 425                 430

Asp Ile Tyr Asn Ile Tyr Asn Ile Tyr Asn Val Tyr Asn Ile Tyr Asn
        435                 440                 445

Val Tyr Asn Ile Tyr Asn Val Tyr Asp Ile Tyr Asn Val Tyr Ser Phe
    450                 455                 460

Leu Ile Leu Leu Leu Ser Leu Phe Phe Ile Met Cys Ser Leu Leu Thr
465                 470                 475                 480

Tyr Tyr Ile Val Phe Phe Thr Glu Lys Ala Lys Met Thr
                485                 490

<210> SEQ ID NO 10
<211> LENGTH: 1494
<212> TYPE: DNA
<213> ORGANISM: Plasmodium falciparum

<400> SEQUENCE: 10
atggaaagtg cagttagcga atgcaatata tacaaaaagg aaaaagataa aaatataatt      60
tacaaacaag aaagaaaatg ttgtatttgc atggtgagtg atttttttta tccaaatttg     120
ggaggaatag aaactcacat ttttgaattg tctaagaatt tgataaaaaa gggtttcaag     180
gttatagttg taacaaattt taataataat aggcatggta taagatggat gggtaatggt     240
attaaggttt attatttgcc cttccagcct tttttagatg tagtgagttt tccaaatatt     300
atagggactt taccactatg tagaaatata ttatataggg aaaaagtcga catagtacat     360
ggtcaccagg ctacgtcagc attagctcat caattcattc ttcatgccaa aaccttagga     420
ataaaaacta tttatacaga tcactcatta tacagttttt cagacaaagg atgcatacat     480
gtaaacaaat tattgaaata ttgtataaac gatgttgatc attctatatg tgtttcccat     540
acgaatagag aaaatttagt tttgagaaca gaaagtaatc catataaaac gtcagttata     600
```

```
ggaaatgccc ttgatactac aaaatttgtt ccttgtatta gtaaaagacc aaagtttcca    660
agaataaata ttattgttat aagtaggtta acatatagaa aaggtataga tttgatagtt    720
aaggtaatac cattagtatg tcaaaaatat ccattcataa aatttattat aggggggagaa   780 ggtcctaaaa gattgttatt agaagaaatg agagaaaagt atcacttaca taattctgtt    840
gtattattag gaaaagtaaa acaagaaaat gtaaaaaata ttttacaaac tggtcatata    900
ttcttaaata catctttaac agaagctttt tgtatagcca taattgaagc agctagttgt    960
ggtttgcttg tcatatctac ggatgtaggt ggaatatctg aagttttacc acacgatatg   1020
atgattttag ctaaaccaaa tcatatcgaa ttatgtaaag cagtcgataa agcattaaaa   1080
attgtacaaa aggtggactc aaatttattc cacgaaaggg taaacatgag tttattaaca   1140
tatgtaaata tatatatata tatatatata tatatatata taatatatat gaataatttt   1200
atttataatc taaccaaaat gtactcttgg gaaaaagtag cggaaaagac ggtaaaatca   1260
cataatacat atattatgaa tattgaaaag gtgtatatga acgtattaaa ttatgcaaat   1320
ccaagcttgt ttaatagaat aagaaaaata tacgaaatta atacacctat tcatgtttcc   1380
tttttttttt tttagacaa aatattgaag aggtcgttag ctttcctcat ttttatgatg   1440
acgaaaataa aaatgaaaaa taagagtttt aaaatgtcga tatataccac ataa         1494
```

<210> SEQ ID NO 11
<211> LENGTH: 497
<212> TYPE: PRT
<213> ORGANISM: Plasmodium falciparum

<400> SEQUENCE: 11

```
Met Glu Ser Ala Val Ser Glu Cys Asn Ile Tyr Lys Lys Glu Lys Asp
 1               5                  10                  15

Lys Asn Ile Ile Tyr Lys Gln Glu Arg Lys Cys Cys Ile Cys Met Val
             20                  25                  30

Ser Asp Phe Phe Tyr Pro Asn Leu Gly Gly Ile Glu Thr His Ile Phe
         35                  40                  45

Glu Leu Ser Lys Asn Leu Ile Lys Lys Gly Phe Lys Val Ile Val Val
     50                  55                  60

Thr Asn Phe Asn Asn Asn Arg His Gly Ile Arg Trp Met Gly Asn Gly
 65                  70                  75                  80

Ile Lys Val Tyr Tyr Leu Pro Phe Gln Pro Phe Leu Asp Val Val Ser
                 85                  90                  95

Phe Pro Asn Ile Ile Gly Thr Leu Pro Leu Cys Arg Asn Ile Leu Tyr
            100                 105                 110

Arg Glu Lys Val Asp Ile Val His Gly His Gln Ala Thr Ser Ala Leu
        115                 120                 125

Ala His Gln Phe Ile Leu His Ala Lys Thr Leu Gly Ile Lys Thr Ile
    130                 135                 140

Tyr Thr Asp His Ser Leu Tyr Ser Phe Ser Asp Lys Gly Cys Ile His
145                 150                 155                 160

Val Asn Lys Leu Leu Lys Tyr Cys Ile Asn Asp Val Asp His Ser Ile
                165                 170                 175

Cys Val Ser His Thr Asn Arg Glu Asn Leu Val Leu Arg Thr Glu Ser
            180                 185                 190

Asn Pro Tyr Lys Thr Ser Val Ile Gly Asn Ala Leu Asp Thr Thr Lys
        195                 200                 205

Phe Val Pro Cys Ile Ser Lys Arg Pro Lys Phe Pro Arg Ile Asn Ile
    210                 215                 220
```

```
Ile Val Ile Ser Arg Leu Thr Tyr Arg Lys Gly Ile Asp Leu Ile Val
225                 230                 235                 240

Lys Val Ile Pro Leu Val Cys Gln Lys Tyr Pro Phe Ile Lys Phe Ile
                245                 250                 255

Ile Gly Gly Glu Gly Pro Lys Arg Leu Leu Glu Glu Met Arg Glu
            260                 265                 270

Lys Tyr His Leu His Asn Ser Val Leu Leu Gly Lys Val Lys Gln
        275                 280                 285

Glu Asn Val Lys Asn Ile Leu Gln Thr Gly His Ile Phe Leu Asn Thr
    290                 295                 300

Ser Leu Thr Glu Ala Phe Cys Ile Ala Ile Glu Ala Ala Ser Cys
305                 310                 315                 320

Gly Leu Leu Val Ile Ser Thr Asp Val Gly Gly Ile Ser Glu Val Leu
                325                 330                 335

Pro His Asp Met Met Ile Leu Ala Lys Pro Asn His Ile Glu Leu Cys
                340                 345                 350

Lys Ala Val Asp Lys Ala Leu Lys Ile Val Gln Lys Val Asp Ser Asn
                355                 360                 365

Leu Phe His Glu Arg Val Asn Met Ser Leu Leu Thr Tyr Val Asn Ile
370                 375                 380

Tyr Ile Tyr Ile Tyr Ile Tyr Ile Tyr Ile Tyr Met Asn Asn Phe
385                 390                 395                 400

Ile Tyr Asn Leu Thr Lys Met Tyr Ser Trp Glu Lys Val Ala Glu Lys
                405                 410                 415

Thr Val Lys Ser His Asn Thr Tyr Ile Met Asn Ile Glu Lys Val Tyr
                420                 425                 430

Met Asn Val Leu Asn Tyr Ala Asn Pro Ser Leu Phe Asn Arg Ile Arg
                435                 440                 445

Lys Ile Tyr Glu Ile Asn Thr Pro Ile His Val Ser Phe Phe Phe
                450                 455                 460

Leu Asp Lys Ile Leu Lys Arg Ser Leu Ala Phe Leu Ile Phe Met Met
465                 470                 475                 480

Thr Lys Ile Lys Met Lys Asn Lys Ser Phe Lys Met Ser Ile Tyr Thr
                485                 490                 495

Thr

<210> SEQ ID NO 12
<211> LENGTH: 2361
<212> TYPE: DNA
<213> ORGANISM: Plasmodium falciparum

<400> SEQUENCE: 12
atgatttaca atgacatttt aacattatgt gcaaataaat taagaggact aattgattca     60
aagatattta tttggttgtt aatattttt agaatattta attgtttatt tgttgtaaca    120
tcattttatc ctgatgaata ttttcaatct gtagaaattg ctcattttg ggcttatgga    180 tatggacata tgtcatggga atgggaacct tgtgtagcat taagatcagt gataactcct    240
tttatttatt atgtattatt tttattttta aaacttatta acatagatca tcctgtttgt    300
gtattataca ttcctaaatt atgtcatggt atatgtgctg ctttgtgtga tttaggtatt    360
tataaattat tgatatattg gtatgttgaa ttgtataatg acgcatggat aaatgaagat    420
aatataaaac gtaatgagaa agatgaaaat aatggaaata acaacaacaa taataataat    480
aacaataata ataacaataa taataataat tattattatc ataataatat attatacaac    540
acaaatgaca ttatttctac aattctatgt tgtcattttt tttgttggtt ttattttat    600
```

```
tccatatgta ggacatcctc gcattccttt gaatgcttgt ttaatatatg gggtgtatat      660
tttttatcac aaaattatta cccccttgaaa aatcaatcaa acaaaataga aaagatagac     720
ttattattac agaacgatgt aatcatacaa aaaggaaaga aacatttaaa tgaatggaca     780
aatttaaaag aaagaaggaa tgatcatcat tttgatacat acgaaaataa ttttatatat     840
cataaaggaa cacaaaattg taaacaatat gataaaaata tggttgatca aaatgtttgt     900
ggtcaaaata tggttgatca cataattcag aacaggaaca atttgtgtag gacacatttt     960
tattcctcca aatttaacaa aatacaagag gcaaaaaatt tattatttag tttattcttt    1020
agctccttgt ctgttatatt tcgtccaaac gctttagtat tttggttatc tttatatata    1080
ctatatatta taaagaatat atttgaaaaa caaaataaaa taaattataa agaaatattc    1140
aaaataggta ttacgtacac tttttttttc ttaactatta ttattataat tgattcttat    1200
tattttgggc acattacatt tcccttttgg aatttttttg tttataattt tttaagtgga    1260
aacaataaat attttggagg gcattctttt tttttttact ttgtatgtgt tataccttct    1320
atatatttaa ctttaacacc ttttttgttt tatggttatt acattatata taataatata    1380
ttgaataagg tgaagtataa gacaattaat atatatatgt atatattgaa acgaattgat    1440
tggatagtat atttagttac acacttagaa atcctatctt tatctttcag taagcataag    1500
gaacataaaa ttgttatagg atatataccg tttcttacaa ttttgttgg atatgcatta    1560 tatataataa aattacatta taaaaaatat aatggcaaaa atggaaagaa tatatataat    1620
aataataaaa tccaatatgg taatataacc ataaagggaa gaaataaata tatttttta    1680 atttcatctt ctcttttttac aaatataagt ttttacttc aatttttatg tattcttttt    1740
ttctgcctta tacataacag atcacctgaa catgtagcct cttatttag aaacttagaa    1800 acgaaagatg atcaaaatat ttatatattt ataacaaatt gttatgatat acctttatat    1860
tcgcatatac atagaaaatt caatatagga ttttttagact gttctcctta tgacacgagt    1920
aatgatgaag ctaccaaaaa ttggagaaaaa cgtatatatg aagataaatt taaggaacaa    1980
ttttttaata ttttttcaaga aaaaaaaaat aataatcatc atataaatag tacatatgga    2040
gatacaatta ctccatatat aataccagat aaatcatttt attggtttgg tcatcatcat    2100
tttaataaaa aaaataattt tcaatatatt tatcaaaaca ttaatttgtc atgtttaaat    2160
tatagatttc atataccttt acaaggacaa ttacctactt atatagttac aacaactatt    2220
gaacttacac atttacaatt attttctgagt acatataatt ataaacttga aacaaagcct    2280 ttttttttctt atttttatgat aagtgaagca aaaggaatag ttccagtata tcattacata    2340
ttcaagaggg ttccttccta a                                                2361
```

<210> SEQ ID NO 13
<211> LENGTH: 786
<212> TYPE: PRT
<213> ORGANISM: Plasmodium falciparum

<400> SEQUENCE: 13

```
Met Ile Tyr Asn Asp Ile Leu Thr Leu Cys Ala Asn Lys Leu Arg Gly
  1               5                  10                  15

Leu Ile Asp Ser Lys Ile Phe Ile Trp Leu Leu Ile Phe Phe Arg Ile
             20                  25                  30

Phe Asn Cys Leu Phe Val Val Thr Ser Phe Tyr Pro Asp Glu Tyr Phe
         35                  40                  45

Gln Ser Val Glu Ile Ala His Phe Trp Ala Tyr Gly Tyr Gly His Met
     50                  55                  60
```

```
Ser Trp Glu Trp Glu Pro Cys Val Ala Leu Arg Ser Val Ile Thr Pro
 65                  70                  75                  80

Phe Ile Tyr Tyr Val Leu Phe Leu Phe Leu Lys Leu Ile Asn Ile Asp
                 85                  90                  95

His Pro Val Cys Val Leu Tyr Ile Pro Lys Leu Cys His Gly Ile Cys
            100                 105                 110

Ala Ala Leu Cys Asp Leu Gly Ile Tyr Lys Leu Leu Ile Tyr Trp Tyr
        115                 120                 125

Val Glu Leu Tyr Asn Asp Ala Trp Ile Asn Glu Asp Asn Ile Lys Arg
130                 135                 140

Asn Glu Lys Asp Glu Asn Asn Gly Asn Asn Asn Asn Asn Asn Asn Asn
145                 150                 155                 160

Asn Asn Asn Asn Asn Asn Asn Asn Tyr Tyr Tyr His Asn Asn
                165                 170                 175

Ile Leu Tyr Asn Thr Asn Asp Ile Ile Ser Thr Ile Leu Cys Cys His
            180                 185                 190

Phe Phe Cys Trp Phe Tyr Phe Tyr Ser Ile Cys Arg Thr Ser Ser His
        195                 200                 205

Ser Phe Glu Cys Leu Phe Asn Ile Trp Gly Val Tyr Phe Leu Ser Gln
    210                 215                 220

Asn Tyr Tyr Pro Leu Lys Asn Gln Ser Asn Lys Ile Glu Lys Ile Asp
225                 230                 235                 240

Leu Leu Leu Gln Asn Asp Val Ile Ile Gln Lys Gly Lys Lys His Leu
                245                 250                 255

Asn Glu Trp Thr Asn Leu Lys Glu Arg Arg Asn Asp His His Phe Asp
            260                 265                 270

Thr Tyr Glu Asn Asn Phe Ile Tyr His Lys Gly Thr Gln Asn Cys Lys
        275                 280                 285

Gln Tyr Asp Lys Asn Met Val Asp Gln Asn Val Cys Gly Gln Asn Met
    290                 295                 300

Val Asp His Ile Ile Gln Asn Arg Asn Asn Leu Cys Arg Thr His Phe
305                 310                 315                 320

Tyr Ser Ser Lys Phe Asn Lys Ile Gln Glu Ala Lys Asn Leu Leu Phe
                325                 330                 335

Ser Leu Phe Phe Ser Ser Leu Ser Val Ile Phe Arg Pro Asn Ala Leu
            340                 345                 350

Val Phe Trp Leu Ser Leu Tyr Ile Leu Tyr Ile Ile Lys Asn Ile Phe
        355                 360                 365

Glu Lys Gln Asn Lys Ile Asn Tyr Lys Glu Ile Phe Lys Ile Gly Ile
    370                 375                 380

Thr Tyr Thr Phe Phe Phe Leu Thr Ile Ile Ile Ile Asp Ser Tyr
385                 390                 395                 400

Tyr Phe Gly His Ile Thr Phe Pro Phe Trp Asn Phe Val Tyr Asn
                405                 410                 415

Phe Leu Ser Gly Asn Asn Lys Tyr Phe Gly Gly His Ser Phe Phe Phe
            420                 425                 430

Tyr Phe Val Cys Val Ile Pro Ser Ile Tyr Leu Thr Leu Thr Pro Phe
        435                 440                 445

Leu Phe Tyr Gly Tyr Tyr Ile Ile Tyr Asn Asn Ile Leu Asn Lys Val
    450                 455                 460

Lys Tyr Lys Thr Ile Asn Ile Tyr Met Tyr Ile Leu Lys Arg Ile Asp
465                 470                 475                 480

Trp Ile Val Tyr Leu Val Thr His Leu Glu Ile Leu Ser Leu Ser Phe
```

```
                        485                 490                 495
Ser Lys His Lys Glu His Lys Ile Val Ile Gly Tyr Ile Pro Phe Leu
                500                 505                 510

Thr Ile Phe Val Gly Tyr Ala Leu Tyr Ile Ile Lys Leu His Tyr Lys
            515                 520                 525

Lys Tyr Asn Gly Lys Asn Gly Lys Asn Ile Tyr Asn Asn Asn Lys Ile
        530                 535                 540

Gln Tyr Gly Asn Ile Thr Ile Lys Gly Arg Asn Lys Tyr Ile Phe Leu
545                 550                 555                 560

Ile Ser Ser Ser Leu Phe Thr Asn Ile Ser Phe Leu Leu Gln Phe Leu
                565                 570                 575

Cys Ile Leu Phe Phe Cys Leu Ile His Asn Arg Ser Pro Glu His Val
                580                 585                 590

Ala Ser Tyr Phe Arg Asn Leu Glu Thr Lys Asp Asp Gln Asn Ile Tyr
            595                 600                 605

Ile Phe Ile Thr Asn Cys Tyr Asp Ile Pro Leu Tyr Ser His Ile His
        610                 615                 620

Arg Lys Phe Asn Ile Gly Phe Leu Asp Cys Ser Pro Tyr Asp Thr Ser
625                 630                 635                 640

Asn Asp Glu Ala Thr Lys Asn Trp Arg Lys Arg Ile Tyr Glu Asp Lys
                645                 650                 655

Phe Lys Glu Gln Phe Phe Asn Ile Phe Gln Lys Lys Asn Asn
                660                 665                 670

His His Ile Asn Ser Thr Tyr Gly Asp Thr Ile Thr Pro Tyr Ile Ile
            675                 680                 685

Pro Asp Lys Ser Phe Tyr Trp Phe Gly His His Phe Asn Lys Lys
        690                 695                 700

Asn Asn Phe Gln Tyr Ile Tyr Gln Asn Ile Asn Leu Ser Cys Leu Asn
705                 710                 715                 720

Tyr Arg Phe His Ile Pro Leu Gln Gly Gln Leu Pro Thr Tyr Ile Val
                725                 730                 735

Thr Thr Thr Ile Glu Leu Thr His Leu Gln Leu Phe Leu Ser Thr Tyr
            740                 745                 750

Asn Tyr Lys Leu Glu Thr Lys Pro Phe Phe Ser Tyr Phe Met Ile Ser
        755                 760                 765

Glu Ala Lys Gly Ile Val Pro Val Tyr His Tyr Ile Phe Lys Arg Val
770                 775                 780

Pro Ser
785

<210> SEQ ID NO 14
<211> LENGTH: 1233
<212> TYPE: DNA
<213> ORGANISM: Plasmodium falciparum

<400> SEQUENCE: 14
atggggcata cacataaaga atataaaaac aatgagaaga gtgcaatatt ttttgagtgg     60 ttgattttt ttgtgggtat aataattcgt ataattattt attattatgg aaggtggcaa    120
gataaaaact ttaatgttaa gtttacagat gtagattatt atgttttttc tgatgctgca    180
aaatatgtac ttatgaacaa atcaccatat gaaagatata catatagata tacacccttta   240 ttagcatata taatgatacc aaatttttt gttcattttt cttttgggaa atattattt     300 tcatttatcg atattcttgt tactattctt ataaatcaaa ttataaaaat caaatatact    360
aattgtaaaa attatatatt ttatacttgt ttatggtttt taaatccatt agtcataatt    420
```

```
atatcccttc gaggtaatgc agatgttatc ccatgcttct taataatagt aacaatcttt      480
tgtatatata aaaacatat cttttgtct tcgattttt atggactagc tgtgaacttt         540
aaaatatata caattattta tgcactacca ttcatgttat atttaaataa aaattattta      600
cttggggaaa atattttca attaaatgaa aaaaaaaaa aaaaaaaaa tgacttccta         660 ttaaacacat ttttatat tttcgtatt atatctaatt tttttgtgga attatttaaa         720
ttaaattatg aacagtttt atttgccata tgtagttcct cggtatttct aattttaaac      780
tgtgtattct atatcatata tggatatgaa ttttgtatg agtctttat atatcatatt       840 attagacgtg atcataggca taacttttcc ctttttttt accttatgta tttaagtatt      900
gagaagaatt caaagattat tcccttaata acctttgtac cacaaataat tttagtagcc    960
ttatttggat ttaaatatgc aagaacgaat ttggaattat ccatgttttt acaaactatt    1020
tcttttattg cattgaataa agtgtgcaca tctcagtatt tcatttggtg tattccattt    1080
ttaccaatta tactttgtgc cataaccta agcaagagaa atatgtttct tataatatcc    1140 tccatttat tttattgt ggcaaaagtg ggctcaaaaa gatttctttt attatataaa      1200
tatgtctttt catatattat ttttttttca tga                                  1233
```

<210> SEQ ID NO 15
<211> LENGTH: 410
<212> TYPE: PRT
<213> ORGANISM: Plasmodium falciparum

<400> SEQUENCE: 15

```
Met Gly His Thr His Lys Glu Tyr Lys Asn Asn Glu Lys Ser Ala Ile
 1               5                  10                  15

Phe Phe Glu Trp Leu Ile Phe Phe Val Gly Ile Ile Arg Ile Ile
            20                  25                  30

Ile Tyr Tyr Tyr Gly Arg Trp Gln Asp Lys Asn Phe Asn Val Lys Phe
        35                  40                  45

Thr Asp Val Asp Tyr Tyr Val Phe Ser Asp Ala Ala Lys Tyr Val Leu
    50                  55                  60

Met Asn Lys Ser Pro Tyr Glu Arg Tyr Thr Tyr Arg Tyr Thr Pro Leu
65                  70                  75                  80

Leu Ala Tyr Ile Met Ile Pro Asn Phe Val His Phe Ser Phe Gly
                85                  90                  95

Lys Ile Leu Phe Ser Phe Ile Asp Ile Leu Val Thr Ile Leu Ile Asn
            100                 105                 110

Gln Ile Ile Lys Ile Lys Tyr Thr Asn Cys Lys Asn Tyr Ile Phe Tyr
        115                 120                 125

Thr Cys Leu Trp Phe Leu Asn Pro Leu Val Ile Ile Ser Leu Arg
    130                 135                 140

Gly Asn Ala Asp Val Ile Pro Cys Phe Leu Ile Ile Val Thr Ile Phe
145                 150                 155                 160

Cys Ile Tyr Lys Lys His Ile Phe Leu Ser Ser Ile Phe Tyr Gly Leu
                165                 170                 175

Ala Val Asn Phe Lys Ile Tyr Thr Ile Ile Tyr Ala Leu Pro Phe Met
            180                 185                 190

Leu Tyr Leu Asn Lys Asn Tyr Leu Leu Gly Glu Asn Ile Phe Gln Leu
        195                 200                 205

Asn Glu Lys Lys Lys Lys Lys Asn Asp Phe Leu Leu Asn Thr Phe
    210                 215                 220

Phe Tyr Ile Phe Arg Ile Ile Ser Asn Phe Phe Val Glu Leu Phe Lys
```

```
                225                 230                 235                 240
Leu Asn Tyr Glu Gln Phe Leu Phe Ala Ile Cys Ser Ser Ser Val Phe
                    245                 250                 255
Leu Ile Leu Asn Cys Val Phe Tyr Ile Ile Tyr Gly Tyr Glu Phe Leu
                260                 265                 270
Tyr Glu Ser Phe Ile Tyr His Ile Ile Arg Arg Asp His Arg His Asn
            275                 280                 285
Phe Ser Leu Phe Phe Tyr Leu Met Tyr Leu Ser Ile Glu Lys Asn Ser
        290                 295                 300
Lys Ile Ile Pro Leu Ile Thr Phe Val Pro Gln Ile Ile Leu Val Ala
305                 310                 315                 320
Leu Phe Gly Phe Lys Tyr Ala Arg Thr Asn Leu Glu Leu Ser Met Phe
                325                 330                 335
Leu Gln Thr Ile Ser Phe Ile Ala Leu Asn Lys Val Cys Thr Ser Gln
                340                 345                 350
Tyr Phe Ile Trp Cys Ile Pro Phe Leu Pro Ile Ile Leu Cys Ala Ile
                355                 360                 365
Thr Leu Ser Lys Arg Asn Met Phe Leu Ile Ile Ser Ser Ile Leu Phe
        370                 375                 380
Phe Ile Val Ala Lys Val Gly Ser Lys Arg Phe Leu Leu Leu Tyr Lys
385                 390                 395                 400
Tyr Val Phe Ser Tyr Ile Ile Phe Phe Ser
                405                 410

<210> SEQ ID NO 16
<211> LENGTH: 3852
<212> TYPE: DNA
<213> ORGANISM: Plasmodium falciparum

<400> SEQUENCE: 16
atgaaaatta aaataatat  taaaaaaaaa aatgataacc tacatcattt cataagtaat     60
catacgctaa tattttctat tatcctactt ataaatctat tgattttttt ctcatttatc    120
aatggctatt tttatgcaag acaaaaactt gaagaaaaat cagaaaacct tgagcttttt    180
agtaggaaag tatttggaga tgaatacgta gaaagtttga aaagaaaaa  aaatacttt     240 tcgattatta atgcaccata tgataaagtt gttatacttt taatagattc cttaagattt    300
gattttaccc tatacgatac taattatgaa aaggaattca taggaaaaga aaaaaataca    360
gatatctaca ataatatatc tagcgaaaaa aaaaatatat caaatgatgg ggaaaaaaaa    420
aactcattat tttttttaaa taatatgata aatgtacatc acatttttaca aaatgaaaaa    480 aacaacactt tattattccg gtttgatgca gatgccccta caataacaac ttcaaggata    540
aaatctatat ttatgggtac cataccaaat tatatggaag taaatgaaaa ctttagtcct    600
acgactagtg ttgaagataa tttttttgaa cagcttcatt taaataataa aaaagtaatt    660
gctatcggtg ataataccat tactcatttg atgaaacatt tttctaaaga attagtttat    720
gagagcttta atgtttttga ttttattca ttagatattg ctgcaaagaa acattttat    780 gaagaatacg aatcaaatga ttgggatatt atgtatatac atatgttggg agttgatcat    840
attggacata taaaaacacc caactcaaaa atcatgggag atgccttaaa agattttgat    900
acattctata tgatatatt aaataaaata aaattagata tcttaaaaaa tattagcaca    960
gaagaaaaag aaaaaaatgaa aataataaaa aaaaaaatat ataaaactta tcgaaacggt   1020
catcacatac aaaatgaaaa tgatcatatt attgataata tacaaaatga aaatgatcat   1080
attattgata atatacaaaa tgaaaatgat catactattg ataatataca aagtgaaaat   1140
```

```
gatcatacta ttgataatat acaaaatgaa aatgatcata ctattgaaga tatacaaatt   1200
gataatgatc atactattga agatattgaa aatcaaagtg aacaaaaaaa tgatgataaa   1260
aaaacactgt tcatatttttt tggtgatcat ggacagctag atacaggaga tcacggagga   1320
tacagcttgg acgaaaccca tagtgctctt tttgcatatt cacccttaaa ctttatatct   1380
ttagataatg acatcattca aaataatttt gttttatatg ataaagataa attaaaaaaa   1440
aatgtgaata cactgaatga agaaaataat aataatgaga atatagataa ttataaaaaa   1500
tatcattcat atttaaaaga tagaaataaa aaatattctt accattataa tgttaaatat   1560
acaaaacaag taaatttaat gagtaccctta tccttattaa ttggatcaac attaccttat   1620
ggaaatatag gaaatattat tatggatttc attcccaatg catatataaa aaataataat   1680
aaaaaaaaaa ataataataa taataataat aataataatt cttcattacc taatgaacag   1740
acaaatttat attatgatct tttaaattta cattatattg ctgaattaaa ttatgctaac   1800
ttatggcaat tgaatagata cctgaatgaa tatgaaaaaa agtataatat aataaaaaat   1860
gaagattatc atttattaa atcctcatgg catattatac aaaaagacaa aaagaattg    1920 ttttttcaac caaataaaaa atttattaaa aatgacattt tattaaaaaa agaaaagaa    1980 tcatatatag aattcataaa tgaaatgaca actctaatgg atatcacaca aaaatatttt   2040
tactatatat tcaacataaa agaaaaatat ttcttaattt tatctattgt tttaaatata   2100
ttcttattat tatttttaaa acattttttat tattattcta aattaaatta ttaccataaa   2160
ttaattaaag taacctttaa tgattttaat aaaaatatttt atttattact ttgtatatgt   2220
gcattacttt tatatttttt tatcttctgt ttatcaatta aagaatataa agatatattc   2280
cgaatatttt ctcatgctaa aatcattttc ataagcaata atatagatat gataatacct   2340
agtataaaaa attaccatat gagcgctaaa cgtaacatga atattacgaa taatgacacc   2400
taccatacat cacataagga tcggaaatca ttcacaaata aagaagagaa acaaaataat   2460
acacttatga atatattcta taatattatt tatttcttaa gaataattcg aaaaaaaatt   2520
gttcagtata taatctttat acatttgaca atatacaatc taactatagg taatattatc   2580
tttattctat ttaaattatt tccgaaaatt ataactaatt catttcaaat attaagaagt   2640
aattatttcc ttttgtttgt tattatatgg agctgttgtg aaatgtcctt taattatata   2700
gataaagaaa gatattatat tcattacatt ttaattgtat atgttatatt tgggatgctt   2760
aaatggaagt atcaccgtgt ctttaatata ctaaaagcct tcattttgtt ggtgcttcta   2820
ataattaatg ctttgtatag ccatacaccc gaatattttg accatggtaa agaaaaaata   2880
tatttaaaag aatctgtact aaaatcagtt tttccaatat catcttatat tcttagctta   2940
atattaataa atagtggtat taataattta ctgaaaaaac gaataaaaat aataataacc   3000
caaatatgga cattacaata tatcctcgtt ttttgttct taaataatat ataccataga   3060
tatattcaat ttataacacc cccaagtatt tatttcttaa ccatttcaac cttcatattc   3120
atattcaata caaatttagg tgtattattt ctcttttata tgacatttct tttttctac    3180 tttattctta taagttccaa ttgttcagaa aatatgatcc aaatgaatga cataacatcg   3240
acatggataa atgaaaatat acataataga aatgatccta taattacaaa aggaaatttg   3300
gagaataaag aaaagtgtac ttcatgtaat acatctataa aagaaaaatt ttattataaa   3360
ttaatgatag aaaaattcaa attattaaat acatgctctg tattaaatga agaagaaata   3420
atgggaatac aaatttataa attaattaga gatatttctt atttttatat aaatgaaaca   3480
gatttttata ttttatcatg tgtacttttta atatattctt tttttataac gggacataaa   3540
```

```
tttattttaa ataacttacc actagtttca ggttatgttg gattgtataa atatgtgtgg    3600
ccaataagtc agttttatat ttttaatcat attttttttc cattcttctt ttcgttattt    3660
tttatcattt atatttataa cataagaagg ataaaaatta taaattcttt taagcaattt    3720
gatttgtatt attttatgt ttatccacta atgaactttt ccttcaaggc ctccttttg     3780 ttttgttgca agtttattat atctgtatgg gtttcatatt acttgaatct gcacataatg    3840
gtaaaaatat aa                                                        3852
```

<210> SEQ ID NO 17
<211> LENGTH: 1283
<212> TYPE: PRT
<213> ORGANISM: Plasmodium falciparum

<400> SEQUENCE: 17

```
Met Lys Ile Lys Asn Asn Ile Lys Lys Asn Asp Asn Leu His His
  1               5                  10                  15

Phe Ile Ser Asn His Thr Leu Ile Phe Ser Ile Ile Leu Leu Ile Asn
                 20                  25                  30

Leu Leu Ile Phe Phe Ser Phe Ile Asn Gly Tyr Phe Tyr Ala Arg Gln
             35                  40                  45

Lys Leu Glu Glu Lys Ser Glu Asn Leu Glu Leu Phe Ser Arg Lys Val
     50                  55                  60

Phe Gly Asp Glu Tyr Val Glu Ser Leu Lys Lys Lys Asn Thr Phe
 65                  70                  75                  80

Ser Ile Ile Asn Ala Pro Tyr Asp Lys Val Val Ile Leu Leu Ile Asp
                 85                  90                  95

Ser Leu Arg Phe Asp Phe Thr Leu Tyr Asp Thr Asn Tyr Glu Lys Glu
            100                 105                 110

Phe Ile Gly Lys Glu Lys Asn Thr Asp Ile Tyr Asn Asn Ile Ser Ser
        115                 120                 125

Glu Lys Lys Asn Ile Ser Asn Asp Gly Glu Lys Lys Asn Ser Leu Phe
    130                 135                 140

Phe Leu Asn Asn Met Ile Asn Val His His Ile Leu Gln Asn Glu Lys
145                 150                 155                 160

Asn Asn Thr Leu Leu Phe Arg Phe Asp Ala Asp Ala Pro Thr Ile Thr
                165                 170                 175

Thr Ser Arg Ile Lys Ser Ile Phe Met Gly Thr Ile Pro Asn Tyr Met
            180                 185                 190

Glu Val Asn Glu Asn Phe Ser Pro Thr Thr Ser Val Glu Asp Asn Phe
        195                 200                 205

Phe Glu Gln Leu His Leu Asn Asn Lys Lys Val Ile Ala Ile Gly Asp
    210                 215                 220

Asn Thr Ile Thr His Leu Met Lys His Phe Ser Lys Glu Leu Val Tyr
225                 230                 235                 240

Glu Ser Phe Asn Val Phe Asp Phe Tyr Ser Leu Asp Ile Ala Ala Lys
                245                 250                 255

Lys His Phe Tyr Glu Glu Tyr Glu Ser Asn Asp Trp Asp Ile Met Tyr
            260                 265                 270

Ile His Met Leu Gly Val Asp His Ile Gly His Ile Lys Thr Pro Asn
        275                 280                 285

Ser Lys Ile Met Gly Asp Ala Leu Lys Asp Phe Asp Thr Phe Ile Tyr
    290                 295                 300

Asp Ile Ile Asn Lys Ile Lys Leu Asp Asn Leu Lys Asn Ile Ser Thr
305                 310                 315                 320
```

```
Glu Glu Lys Glu Lys Met Lys Ile Ile Lys Lys Ile Tyr Lys Thr
            325                 330                 335
Tyr Arg Asn Gly His His Ile Gln Asn Glu Asn Asp His Ile Ile Asp
            340                 345                 350
Asn Ile Gln Asn Glu Asn Asp His Ile Ile Asp Asn Ile Gln Asn Glu
            355                 360                 365
Asn Asp His Thr Ile Asp Asn Ile Gln Ser Glu Asn Asp His Thr Ile
            370                 375                 380
Asp Asn Ile Gln Asn Glu Asn Asp His Thr Ile Glu Asp Ile Gln Ile
385                 390                 395                 400
Asp Asn Asp His Thr Ile Glu Asp Ile Glu Asn Gln Ser Glu Gln Lys
            405                 410                 415
Asn Asp Asp Lys Lys Thr Leu Phe Ile Phe Gly Asp His Gly Gln
            420                 425                 430
Leu Asp Thr Gly Asp His Gly Gly Tyr Ser Leu Asp Glu Thr His Ser
            435                 440                 445
Ala Leu Phe Ala Tyr Ser Pro Leu Asn Phe Ile Ser Leu Asp Asn Asp
            450                 455                 460
Ile Ile Gln Asn Asn Phe Val Leu Tyr Asp Lys Asp Lys Leu Lys Lys
465                 470                 475                 480
Asn Val Asn Thr Leu Asn Glu Glu Asn Asn Asn Glu Asn Ile Asp
            485                 490                 495
Asn Tyr Lys Lys Tyr His Ser Tyr Leu Lys Asp Arg Asn Lys Lys Tyr
            500                 505                 510
Ser Tyr His Tyr Asn Val Lys Tyr Thr Lys Gln Val Asn Leu Met Ser
            515                 520                 525
Thr Leu Ser Leu Leu Ile Gly Ser Thr Leu Pro Tyr Gly Asn Ile Gly
            530                 535                 540
Asn Ile Ile Met Asp Phe Ile Pro Asn Ala Tyr Ile Lys Asn Asn
545                 550                 555                 560
Lys Lys Lys Asn Asn Asn Asn Asn Asn Asn Asn Ser Ser Leu
            565                 570                 575
Pro Asn Glu Gln Thr Asn Leu Tyr Tyr Asp Leu Leu Asn Leu His Tyr
            580                 585                 590
Ile Ala Glu Leu Asn Tyr Ala Asn Leu Trp Gln Leu Asn Arg Tyr Leu
            595                 600                 605
Asn Glu Tyr Glu Lys Lys Tyr Asn Ile Ile Lys Asn Glu Asp Tyr His
            610                 615                 620
Phe Ile Lys Ser Ser Trp His Ile Ile Gln Lys Asp Lys Glu Leu
625                 630                 635                 640
Phe Phe Gln Pro Asn Lys Lys Phe Ile Lys Asn Asp Ile Leu Leu Lys
            645                 650                 655
Lys Glu Lys Glu Ser Tyr Ile Glu Phe Ile Asn Glu Met Thr Thr Leu
            660                 665                 670
Met Asp Ile Thr Gln Lys Tyr Phe Tyr Tyr Ile Phe Asn Ile Lys Glu
            675                 680                 685
Lys Tyr Phe Leu Ile Leu Ser Ile Val Leu Asn Ile Phe Leu Leu
            690                 695                 700
Phe Leu Lys His Phe Tyr Tyr Tyr Ser Lys Leu Asn Tyr Tyr His Lys
705                 710                 715                 720
Leu Ile Lys Val Thr Phe Asn Asp Phe Asn Lys Asn Ile Tyr Leu Leu
            725                 730                 735
Leu Cys Ile Cys Ala Leu Leu Leu Tyr Phe Phe Ile Phe Cys Leu Ser
```

```
                740             745             750
Ile Lys Glu Tyr Lys Asp Ile Phe Arg Ile Phe Ser His Ala Lys Ile
        755                 760             765

Ile Phe Ile Ser Asn Asn Ile Asp Met Ile Ile Pro Ser Ile Lys Asn
        770             775                 780

Tyr His Met Ser Ala Lys Arg Asn Met Asn Ile Thr Asn Asn Asp Thr
785                 790                 795                 800

Tyr His Thr Ser His Lys Asp Arg Lys Ser Phe Thr Asn Lys Glu Glu
                805                 810                 815

Lys Gln Asn Asn Thr Leu Met Asn Ile Phe Tyr Asn Ile Ile Tyr Phe
            820                 825                 830

Leu Arg Ile Ile Arg Lys Lys Ile Val Gln Tyr Ile Ile Phe Ile His
                835                 840                 845

Leu Thr Ile Tyr Asn Leu Thr Ile Gly Asn Ile Ile Phe Ile Leu Phe
        850                 855                 860

Lys Leu Phe Pro Lys Ile Ile Thr Asn Ser Phe Gln Ile Leu Arg Ser
865                 870                 875                 880

Asn Tyr Phe Leu Leu Phe Val Ile Ile Trp Ser Cys Cys Glu Met Ser
                885                 890                 895

Phe Asn Tyr Ile Asp Lys Glu Arg Tyr Tyr Ile His Tyr Ile Leu Ile
                900                 905                 910

Val Tyr Val Ile Phe Gly Met Leu Lys Trp Lys Tyr His Arg Val Phe
        915                 920                 925

Asn Ile Leu Lys Ala Phe Ile Leu Leu Val Leu Leu Ile Ile Asn Ala
        930                 935                 940

Leu Tyr Ser His Thr Pro Glu Tyr Phe Asp His Gly Lys Glu Lys Ile
945                 950                 955                 960

Tyr Leu Lys Glu Ser Val Leu Lys Ser Val Phe Pro Ile Ser Ser Tyr
                965                 970                 975

Ile Leu Ser Leu Ile Leu Ile Asn Ser Gly Ile Asn Asn Leu Leu Lys
            980                 985                 990

Lys Arg Ile Lys Ile Ile Ile Thr Gln Ile Trp Thr Leu Gln Tyr Ile
            995                 1000                1005

Leu Val Phe Leu Phe Leu Asn Asn Ile Tyr His Arg Tyr Ile Gln Phe
        1010                1015                1020

Ile Thr Pro Pro Ser Ile Tyr Phe Leu Thr Ile Ser Thr Phe Ile Phe
1025                1030                1035                1040

Ile Phe Asn Thr Asn Leu Gly Val Leu Phe Leu Phe Tyr Met Thr Phe
            1045                1050                1055

Leu Phe Phe Tyr Phe Ile Leu Ile Ser Ser Asn Cys Ser Glu Asn Met
            1060                1065                1070

Ile Gln Met Asn Asp Ile Thr Ser Thr Trp Ile Asn Glu Asn Ile His
        1075                1080                1085

Asn Arg Asn Asp Pro Ile Ile Thr Lys Gly Asn Leu Glu Asn Lys Glu
            1090                1095                1100

Lys Cys Thr Ser Cys Asn Thr Ser Ile Lys Glu Lys Phe Tyr Tyr Lys
1105                1110                1115                1120

Leu Met Ile Glu Lys Phe Lys Leu Leu Asn Thr Cys Ser Val Leu Asn
                1125                1130                1135

Glu Glu Glu Ile Met Gly Ile Gln Ile Tyr Lys Leu Ile Arg Asp Ile
                1140                1145                1150

Ser Tyr Phe Tyr Ile Asn Glu Thr Asp Phe Tyr Ile Leu Ser Cys Val
            1155                1160                1165
```

```
Leu Leu Ile Tyr Ser Phe Phe Ile Thr Gly His Lys Phe Ile Leu Asn
    1170                1175                1180

Asn Leu Pro Leu Val Ser Gly Tyr Val Gly Leu Tyr Lys Tyr Val Trp
1185                1190                1195                1200

Pro Ile Ser Gln Phe Tyr Ile Phe Asn His Ile Phe Phe Pro Phe Phe
                1205                1210                1215

Phe Ser Leu Phe Phe Ile Ile Tyr Ile Tyr Asn Ile Arg Arg Ile Lys
            1220                1225                1230

Ile Ile Asn Ser Phe Lys Gln Phe Asp Leu Tyr Tyr Phe Tyr Val Tyr
        1235                1240                1245

Pro Leu Met Asn Phe Ser Phe Lys Ala Ser Phe Leu Phe Cys Cys Lys
    1250                1255                1260

Phe Ile Ile Ser Val Trp Val Ser Tyr Tyr Leu Asn Leu His Ile Met
1265                1270                1275                1280

Val Lys Ile

<210> SEQ ID NO 18
<211> LENGTH: 2433
<212> TYPE: DNA
<213> ORGANISM: Plasmodium falciparum

<400> SEQUENCE: 18
atgggatttt cagaaaatcc caaattctgc ctgctcataa ataagcttat caagaaatct      60
aaagttatag gcgttttctt atcaattatt ggtgtgattt tcttttttggt gtttaataag    120 tttaataaga atgctgaatt agacgctagg acatttaccc aatttgttgg taattcagta    180
ttgaacaaaa agaatgagaa gttttataat gatacaaatt cttatttcat gaactataca    240
tatgaaggga agaagatat aataaagttg atatatgatt atattagaaa aaatatatta    300
gtaaatgtag agaatgagat ggttaaaata aaattaacgg atagaattga acagaatata    360
ttgataagta atgtaggatg taaatattgt aataatatgg aaagtttagt tgtggtaata    420
aattttgatt ttaaagaaag gaaatatttt catagcgtaa ttatcggttt aacgttaatg    480
gaacattttt ctaaatgtaa ctatatgagt aaggatgtga ctttttttatt taccaataaa    540 gaattattat attctttagg tgttcaagaa tttatacaaa atatttttta taataatact    600
aatagaattg gaaaaaaaat tattagatct tctactatta ttgaatttga ttctatttat    660
ccttcttata ttaaaattaa ttatgaagga ttaaatggta tgttacctaa tcaagactta    720
atattattat taacaaatga acttcatttt tattctattc ctattaaaat ggagcttact    780
catggttcca tatttgatat ggccctagaa aagaattatg aaaatggtca catatacttt    840
ctgaggtaca aaaaaaaata tgaatatata cgtgatgata atgatgaaat caagaacatt    900
cccgcattta ctgcaacggg gggtagcaaa gtacccataa gaaataaaat gattaatttg    960
ttcaacttaa ccaaagcatt acaaagttat ttaagaagtc agagtaatac acatgaaggc   1020
ttttgtcatt cttcaaattt ttattttttt aatacattca gaaggcatat accaataagt   1080
atatattgtt atagtgttta tttaatatgc gcatatagca taatgaaatt atttaaatca   1140 acgatatta gaagctacat aaatttttta acaggtttct acacttattt gattacaata   1200
ttaattattt ccctacctat atatttaatt tcaacaaata aaaaattttta tgagttgttg   1260 aattttgaag aaaattatat tccttcatgt tatgaatggc atcctgataa ttttgataaa   1320
tatataaaaa ttgcaaatat atggtggaat gttttatttt tctcaatttt tggtgcattt   1380 tttttaatt tatttatttc tttttagtt aataaaaaaa gaaagttat accaaaaaaa   1440 aatgatcaaa atgaatcatt tgatggctat aaaaaggtag agaaggtaga acgaattta   1500
```

```
atattagaaa aaatcaaaga attgcaaaat gaaataatga aacgaaaagg tattacaaat      1560
aatcataata atattaaaaa ttataatatt tatacaaatg aaaatatata caataataat      1620
ataaataata taaataataa taataatatt tatgaaaact tatatgataa tggagaagta      1680
aaaaaaaaca ttctggttaa accaaaaatt ataaatagcg atgatgaaga ttttcttctt      1740
gaaaaaaaaa attccgaatt cattaaaaaa atagaaaaac aaatagaaat attagaagaa      1800
aaattggaat ttttaagtaa tgatgaaaat gtaaaatata ttttttataa taattctata      1860
gcaccattta atacaatgat gatatatatg aatattttt atttcatatt agtagcgcta      1920
ttaagttcgt tatataattg gtcctattct gtattattta gcctgctatt tgtaattcct      1980
atatcaattt tacataattt aaaaacaaaa ccagtcagaa tttttaagaa gattattctt      2040
tcacttttta ttctttgtat gtttatttat atgtatccta atgataatca tctttggaat      2100
ataagacaga agctaactaa tttatttagg aataatatat caaaatgttg taaatattta      2160
gacaagcaca aaatattaca aagcaaatat ttcccagaaa gtttgcaatt tatttgttcg      2220
aataggttat ttgattcatt ttactcaaat aaatatttt tggataatct aaatattaaa      2280
tttagttatg tcttggatat tcaaaatgga ttccttattaa ctttatacaa tttagcaaga      2340
aatcattttt gtattggtac agctacctat cctttaatat gctttacctt attcccaata      2400
gtattttata tagttttttt attttttgt taa                                    2433
```

<210> SEQ ID NO 19
<211> LENGTH: 810
<212> TYPE: PRT
<213> ORGANISM: Plasmodium falciparum

<400> SEQUENCE: 19

```
Met Gly Phe Ser Glu Asn Pro Lys Phe Cys Leu Leu Ile Asn Lys Leu
1               5                  10                  15

Ile Lys Lys Ser Lys Val Ile Gly Val Phe Leu Ser Ile Ile Gly Val
            20                  25                  30

Ile Phe Phe Leu Val Phe Asn Lys Phe Asn Lys Asn Ala Glu Leu Asp
        35                  40                  45

Ala Arg Thr Phe Thr Gln Phe Val Gly Asn Ser Val Leu Asn Lys Lys
    50                  55                  60

Asn Glu Lys Phe Tyr Asn Asp Thr Asn Ser Tyr Phe Met Asn Tyr Thr
65                  70                  75                  80

Tyr Glu Gly Lys Glu Asp Ile Ile Lys Leu Ile Tyr Asp Tyr Ile Arg
                85                  90                  95

Lys Asn Ile Leu Val Asn Val Glu Asn Glu Met Val Lys Ile Lys Leu
            100                 105                 110

Thr Asp Arg Ile Glu Gln Asn Ile Leu Ile Ser Asn Val Gly Cys Lys
        115                 120                 125

Tyr Cys Asn Asn Met Glu Ser Leu Val Val Ile Asn Phe Asp Phe
    130                 135                 140

Lys Glu Arg Lys Tyr Phe His Ser Val Ile Ile Gly Leu Thr Leu Met
145                 150                 155                 160

Glu His Phe Ser Lys Cys Asn Tyr Met Ser Lys Asp Val Thr Phe Leu
                165                 170                 175

Phe Thr Asn Lys Glu Leu Leu Tyr Ser Leu Gly Val Gln Glu Phe Ile
            180                 185                 190

Gln Lys Tyr Phe Tyr Asn Asn Thr Asn Arg Ile Gly Lys Lys Ile Ile
        195                 200                 205
```

-continued

```
Arg Ser Ser Thr Ile Ile Glu Phe Asp Ser Ile Tyr Pro Ser Tyr Ile
    210                 215                 220

Lys Ile Asn Tyr Glu Gly Leu Asn Gly Met Leu Pro Asn Gln Asp Leu
225                 230                 235                 240

Ile Leu Leu Leu Thr Asn Glu Leu His Phe Tyr Ser Ile Pro Ile Lys
                245                 250                 255

Met Glu Leu Thr His Gly Ser Ile Phe Asp Met Ala Leu Glu Lys Asn
                260                 265                 270

Tyr Glu Asn Gly His Ile Tyr Phe Leu Arg Tyr Lys Lys Tyr Glu
            275                 280                 285

Tyr Ile Arg Asp Asp Asn Asp Glu Ile Lys Asn Ile Pro Ala Phe Thr
290                 295                 300

Ala Thr Gly Gly Ser Lys Val Pro Ile Arg Asn Lys Met Ile Asn Leu
305                 310                 315                 320

Phe Asn Leu Thr Lys Ala Leu Gln Ser Tyr Leu Arg Ser Gln Ser Asn
                325                 330                 335

Thr His Glu Gly Phe Cys His Ser Ser Asn Phe Tyr Phe Asn Thr
                340                 345                 350

Phe Arg Arg His Ile Pro Ile Ser Ile Tyr Cys Tyr Ser Val Tyr Leu
                355                 360                 365

Ile Cys Ala Tyr Ser Ile Met Lys Leu Phe Lys Ser Thr Ile Phe Arg
370                 375                 380

Ser Tyr Ile Asn Phe Leu Thr Gly Phe Tyr Thr Tyr Leu Ile Thr Ile
385                 390                 395                 400

Leu Ile Ile Ser Leu Pro Ile Tyr Leu Ile Ser Thr Asn Lys Lys Phe
                405                 410                 415

Tyr Glu Leu Leu Asn Phe Glu Glu Asn Tyr Ile Pro Ser Cys Tyr Glu
                420                 425                 430

Trp His Pro Asp Asn Phe Asp Lys Tyr Ile Lys Ile Ala Asn Ile Trp
                435                 440                 445

Trp Asn Val Leu Phe Phe Ser Ile Phe Gly Ala Phe Phe Asn Leu
    450                 455                 460

Phe Ile Ser Phe Leu Val Asn Lys Lys Arg Lys Val Ile Pro Lys Lys
465                 470                 475                 480

Asn Asp Gln Asn Glu Ser Phe Asp Gly Tyr Lys Lys Val Glu Lys Val
                485                 490                 495

Glu Arg Ile Leu Ile Leu Glu Lys Ile Lys Glu Leu Gln Asn Glu Ile
                500                 505                 510

Met Lys Arg Lys Gly Ile Thr Asn Asn His Asn Asn Ile Lys Asn Tyr
                515                 520                 525

Asn Ile Tyr Thr Asn Glu Asn Ile Tyr Asn Asn Ile Asn Asn Ile
530                 535                 540

Asn Asn Asn Asn Asn Ile Tyr Glu Asn Leu Tyr Asp Asn Gly Glu Val
545                 550                 555                 560

Lys Lys Asn Ile Leu Val Lys Pro Lys Ile Ile Asn Ser Asp Asp Glu
                565                 570                 575

Asp Phe Leu Leu Glu Lys Lys Asn Ser Glu Phe Ile Lys Ile Glu
                580                 585                 590

Lys Gln Ile Glu Ile Leu Glu Glu Lys Leu Glu Phe Leu Ser Asn Asp
                595                 600                 605

Glu Asn Val Lys Tyr Ile Phe Tyr Asn Asn Ser Ile Ala Pro Phe Asn
610                 615                 620

Thr Met Met Ile Tyr Met Asn Ile Phe Tyr Phe Ile Leu Val Ala Leu
625                 630                 635                 640
```

```
Leu Ser Ser Leu Tyr Asn Trp Ser Tyr Ser Val Leu Phe Ser Leu Leu
                645                 650                 655

Phe Val Ile Pro Ile Ser Ile Leu His Asn Leu Lys Thr Lys Pro Val
                660                 665                 670

Arg Ile Phe Lys Lys Ile Ile Leu Ser Leu Phe Ile Leu Cys Met Phe
                675                 680                 685

Ile Tyr Met Tyr Pro Asn Asp Asn His Leu Trp Asn Ile Arg Gln Lys
                690                 695                 700

Leu Thr Asn Leu Phe Arg Asn Asn Ile Ser Lys Cys Cys Lys Tyr Leu
705                 710                 715                 720

Asp Lys His Lys Ile Leu Gln Ser Lys Tyr Phe Pro Glu Ser Leu Gln
                725                 730                 735

Phe Ile Cys Ser Asn Arg Leu Phe Asp Ser Phe Tyr Ser Asn Lys Tyr
                740                 745                 750

Phe Leu Asp Asn Leu Asn Ile Lys Phe Ser Tyr Val Leu Asp Ile Gln
                755                 760                 765

Asn Gly Phe Leu Leu Thr Leu Tyr Asn Leu Ala Arg Asn His Phe Cys
                770                 775                 780

Ile Gly Thr Ala Thr Tyr Pro Leu Ile Cys Phe Thr Leu Phe Pro Ile
785                 790                 795                 800

Val Phe Tyr Ile Val Phe Leu Phe Phe Cys
                805                 810

<210> SEQ ID NO 20
<211> LENGTH: 780
<212> TYPE: DNA
<213> ORGANISM: Plasmodium falciparum

<400> SEQUENCE: 20
atggttattc gatttttcct gtttgtcatt acactcttag gcttatgcat aaatatggtg      60
tgttgtaatt ttaaatattc gattatatta cctacttaca atgaaaaaga aaacttacca     120
tatcttattt atatgataat tgatgaatta aataaacatg aaattaaatt tgaaataatt     180
gtaatagatg ataatagtca agatggtact gcagatgtgt acaaaaagtt acaaacatt      240 tttaaggatg aagaattatt attaatacaa agaaaaggaa aattagggtt aggttctgca     300
tatatggaag gtttaaaaaa tgtaacagga gattttgtta ataatggga tgctgattta      360 tcacatcatc ctaaatatat ttataacttt attaaaaaac aaagagaaaa aaattgtgac     420
attgttacag gcacaagata taagaaccaa ggtggaatat caggatggtc atttaataga     480
attataataa gtagagtagc aaattttta gctcaatttc tattattcat taatctatca      540
gatttaaccg ggtcttttag attatataaa actaatgtac tgaaggaact tatgcaatct     600
attaataata caggttatgt ttttcaaatg gaagttcttg taagagcata taaaatggga     660
aaatctatag aagaagttgg ttacgttttt gttgatagat tatttggaaa atcaaaactg     720
gaaactacag atattttaca atacttatca ggtcttttca agttattctg gtcaatataa     780

<210> SEQ ID NO 21
<211> LENGTH: 259
<212> TYPE: PRT
<213> ORGANISM: Plasmodium falciparum

<400> SEQUENCE: 21

Met Val Ile Arg Phe Phe Leu Phe Val Ile Thr Leu Leu Gly Leu Cys
1               5                  10                  15

Ile Asn Met Val Cys Cys Asn Phe Lys Tyr Ser Ile Ile Leu Pro Thr
```

|  |  |  | 20 |  |  |  | 25 |  |  |  | 30 |  |  |
|---|---|---|---|---|---|---|---|---|---|---|---|---|---|

Tyr Asn Glu Lys Glu Asn Leu Pro Tyr Leu Ile Tyr Met Ile Ile Asp
          35                  40                  45

Glu Leu Asn Lys His Glu Ile Lys Phe Glu Ile Ile Val Ile Asp Asp
 50                   55                  60

Asn Ser Gln Asp Gly Thr Ala Asp Val Tyr Lys Lys Leu Gln Asn Ile
65                   70                   75                  80

Phe Lys Asp Glu Glu Leu Leu Leu Ile Gln Arg Lys Gly Lys Leu Gly
                 85                  90                   95

Leu Gly Ser Ala Tyr Met Glu Gly Leu Lys Asn Val Thr Gly Asp Phe
          100                  105                110

Val Ile Ile Met Asp Ala Asp Leu Ser His His Pro Lys Tyr Ile Tyr
         115                  120                125

Asn Phe Ile Lys Lys Gln Arg Glu Lys Asn Cys Asp Ile Val Thr Gly
     130                  135                140

Thr Arg Tyr Lys Asn Gln Gly Gly Ile Ser Gly Trp Ser Phe Asn Arg
145                  150                  155               160

Ile Ile Ile Ser Arg Val Ala Asn Phe Leu Ala Gln Phe Leu Leu Phe
         165                  170                175

Ile Asn Leu Ser Asp Leu Thr Gly Ser Phe Arg Leu Tyr Lys Thr Asn
     180                  185                190

Val Leu Lys Glu Leu Met Gln Ser Ile Asn Asn Thr Gly Tyr Val Phe
         195                  200                205

Gln Met Glu Val Leu Val Arg Ala Tyr Lys Met Gly Lys Ser Ile Glu
     210                  215                220

Glu Val Gly Tyr Val Phe Val Asp Arg Leu Phe Gly Lys Ser Lys Leu
225                  230                  235               240

Glu Thr Thr Asp Ile Leu Gln Tyr Leu Ser Gly Leu Phe Lys Leu Phe
         245                  250                255

Trp Ser Ile

<210> SEQ ID NO 22
<211> LENGTH: 843
<212> TYPE: DNA
<213> ORGANISM: Saccharomyces cerevisiae

<400> SEQUENCE: 22

```
atgacaagat ctccctggaa gcgcctacta tggttgaaac aggagtaccc agataattat      60
acagatccaa gttttattga gttgagagca agacaaaagg ctgagagtaa ccagaagtct     120
gatagaaaat tatcagaagc tgctcgcgct caaattaggt tggattttat aagtttctac     180
caaaccatat tgaacacttc tttcatttac atcactttta catatattta ctattatggc     240
ttcgatccta ttccgccaac tattttcctt tcatttataa cattgattat atcaaggacg     300
aaagtcgacc ctctattgtc ctcattcatg gacgtaaagt cttcgctgat atcacatttt     360
gcaatgttga ctctctctcc agtcctcaaa tctctttcta aaacaactgc atctgattcc     420
atatggacat tgtctttttg gctgacccta tggtacattt cgttatttc gtcaacaaag     480
tccaaagata aaccctctaa cctttccacc aatatacttg tcgcccttgt tgctgtccta     540
tcatcgaggc tttcgaccac aatcgacgta ttctgttttc ttttaatttg tattcagttg     600
aatatcattc tacccactta tttatcggtg acgaataagg tagtaccaat aatttcaaat     660
attattgtat actcattttt gaatgttgct ctaggttgga tttatatgct gttgattttc     720
tttgcttcag tatttatat tactgtttta cctaagtggt tcatctactg gaaaatcaat     780
```
tatcataaac gggataacga tctactaagt acatgggatg caagaacacc aatattggat    840
tag    843

<210> SEQ ID NO 23
<211> LENGTH: 280
<212> TYPE: PRT
<213> ORGANISM: Saccharomyces cerevisiae

<400> SEQUENCE: 23

Met Thr Arg Ser Pro Trp Lys Arg Leu Leu Trp Leu Lys Gln Glu Tyr
1               5                   10                  15

Pro Asp Asn Tyr Thr Asp Pro Ser Phe Ile Glu Leu Arg Ala Arg Gln
            20                  25                  30

Lys Ala Glu Ser Asn Gln Lys Ser Asp Arg Lys Leu Ser Glu Ala Ala
        35                  40                  45

Arg Ala Gln Ile Arg Leu Asp Phe Ile Ser Phe Tyr Gln Thr Ile Leu
    50                  55                  60

Asn Thr Ser Phe Ile Tyr Ile Thr Phe Thr Tyr Ile Tyr Tyr Tyr Gly
65                  70                  75                  80

Phe Asp Pro Ile Pro Pro Thr Ile Phe Leu Ser Phe Ile Thr Leu Ile
                85                  90                  95

Ile Ser Arg Thr Lys Val Asp Pro Leu Leu Ser Ser Phe Met Asp Val
            100                 105                 110

Lys Ser Ser Leu Ile Ile Thr Phe Ala Met Leu Thr Leu Ser Pro Val
        115                 120                 125

Leu Lys Ser Leu Ser Lys Thr Thr Ala Ser Asp Ser Ile Trp Thr Leu
    130                 135                 140

Ser Phe Trp Leu Thr Leu Trp Tyr Ile Phe Val Ile Ser Ser Thr Lys
145                 150                 155                 160

Ser Lys Asp Lys Pro Ser Asn Leu Ser Thr Asn Ile Leu Val Ala Leu
                165                 170                 175

Val Ala Val Leu Ser Ser Arg Leu Ser Thr Thr Ile Asp Val Phe Cys
            180                 185                 190

Phe Leu Leu Ile Cys Ile Gln Leu Asn Ile Ile Leu Pro Thr Tyr Leu
        195                 200                 205

Ser Val Thr Asn Lys Val Val Pro Ile Ile Ser Asn Ile Ile Val Tyr
    210                 215                 220

Ser Phe Leu Asn Val Ala Leu Gly Trp Ile Tyr Met Leu Leu Ile Phe
225                 230                 235                 240

Phe Ala Ser Val Phe Tyr Ile Thr Val Leu Pro Lys Trp Phe Ile Tyr
                245                 250                 255

Trp Lys Ile Asn Tyr His Lys Arg Asp Asn Asp Leu Leu Ser Thr Trp
            260                 265                 270

Asp Ala Arg Thr Pro Ile Leu Asp
        275                 280

<210> SEQ ID NO 24
<211> LENGTH: 764
<212> TYPE: DNA
<213> ORGANISM: Saccharomyces cerevisiae

<400> SEQUENCE: 24
atgattagta aagagtatga atttggtaag actagtatac tgaatagaaa gaagtataca     60
ttagttatcg atgaagacaa gaatggcaat tttataagat ttaccgtttt acctgtatct    120
aaccgaaagt tcaaaaaagt caagcaaaat gggagggtag agattaacat gggcatacaa    180

```
tatcaccaaa ttgtacttat tttactactg aatattttgt tctatgtaat ttgcctaaga    240
tcaagatttc tcgaacatat taatagaact tttgaagtga caatcgcgcg aagtttccag    300
atcttaatta taatgggatt gtttgcctta ggtacaatta tacttgtgag gggacctagt    360
gtggaaactg taacaatttt caaagaaagt ggactacagc tgtccagagt gaagggtatg    420
gttatatttc ctcaacaatg gaatcggaag ttctttgaac aagtagagtt tatatccaat    480
gaaagaatta ttgatgtagt gatcaatgaa ggattctgtc ggggatttcg agtgatattc    540
tatcttgcag caattgtacg taaatcgtct acgcttaagc tattatttcc agtatgtatt    600
caagcgaatt taagattgtt tcttacttca acgatctgat tagaaatact aacacaacaa    660
tgcagtcaaa tttgcccagt atcgatgacc aacgtctaat atacaacata tctagaaaat    720
atctcagtaa gcaagaaaaa ccctgagca gaccaaaaga ttga                     764
```

<210> SEQ ID NO 25
<211> LENGTH: 229
<212> TYPE: PRT
<213> ORGANISM: Saccharomyces cerevisiae

<400> SEQUENCE: 25

```
Met Ile Ser Lys Glu Tyr Glu Phe Gly Lys Thr Ser Ile Leu Asn Arg
 1               5                  10                  15

Lys Lys Tyr Thr Leu Val Ile Asp Glu Asp Lys Asn Gly Asn Phe Ile
            20                  25                  30

Arg Phe Thr Val Leu Pro Val Ser Asn Arg Lys Phe Lys Lys Val Lys
        35                  40                  45

Gln Asn Gly Arg Val Glu Ile Asn Met Gly Ile Gln Tyr His Gln Ile
    50                  55                  60

Val Leu Ile Leu Leu Asn Ile Leu Phe Tyr Val Ile Cys Leu Arg
65                  70                  75                  80

Ser Arg Phe Leu Glu His Ile Asn Arg Thr Phe Glu Val Thr Ile Ala
                85                  90                  95

Arg Ser Phe Gln Ile Leu Ile Ile Met Gly Leu Phe Ala Leu Gly Thr
           100                 105                 110

Ile Ile Leu Val Arg Gly Pro Ser Val Glu Thr Val Thr Ile Phe Lys
       115                 120                 125

Glu Ser Gly Leu Gln Leu Ser Arg Val Lys Gly Met Val Ile Phe Pro
   130                 135                 140

Gln Gln Trp Asn Arg Lys Phe Phe Glu Gln Val Glu Phe Ile Ser Asn
145                 150                 155                 160

Glu Arg Ile Ile Asp Val Val Ile Asn Glu Gly Phe Cys Arg Gly Phe
                165                 170                 175

Arg Val Ile Phe Tyr Leu Ala Ala Ile Val Arg Lys Ser Ser Thr Leu
            180                 185                 190

Lys Leu Leu Phe Pro Ser Asn Leu Pro Ser Ile Asp Asp Gln Arg Leu
        195                 200                 205

Ile Tyr Asn Ile Ser Arg Lys Tyr Leu Ser Lys Gln Glu Lys Pro Leu
    210                 215                 220

Ser Arg Pro Lys Asp
225
```

<210> SEQ ID NO 26
<211> LENGTH: 423
<212> TYPE: DNA
<213> ORGANISM: Saccharomyces cerevisiae

<400> SEQUENCE: 26

```
atgtatacaa aagagtacta ctggttttca caatatatga taataacaag cactttggtg    60
ctcaccataa tatggtccat cttaccatca tcgctgggtg aggctgcacc aaagcagttt   120
atcaacacgc tattggacat cttcccacaa agaagatgga ttattacctt ggagagcata   180
atgctgatgg gcatgctatg cacatacatc ggccttctga tgtacaatga agatacatta   240
acaccgccgc tagattctct atctacagta acggatgccg gtggtcaact tgtaatagag   300
gacgacccgg acgtattcgt taagaaatgg gcctttaaag aaacaagtgg tatttacgat   360
ctgtctctga tggatgcctg ccaacttctc tacctatatg ataacgacca taccagcaca   420
tag                                                                423
```

<210> SEQ ID NO 27
<211> LENGTH: 140
<212> TYPE: PRT
<213> ORGANISM: Saccharomyces cerevisiae

<400> SEQUENCE: 27

```
Met Tyr Thr Lys Glu Tyr Tyr Trp Phe Ser Gln Tyr Met Ile Ile Thr
1               5                   10                  15

Ser Thr Leu Val Leu Thr Ile Ile Trp Ser Ile Leu Pro Ser Ser Leu
            20                  25                  30

Gly Glu Ala Ala Pro Lys Gln Phe Ile Asn Thr Leu Leu Asp Ile Phe
        35                  40                  45

Pro Gln Arg Arg Trp Ile Ile Thr Leu Glu Ser Ile Met Leu Met Gly
    50                  55                  60

Met Leu Cys Thr Tyr Ile Gly Leu Leu Met Tyr Asn Glu Asp Thr Leu
65                  70                  75                  80

Thr Pro Pro Leu Asp Ser Leu Ser Thr Val Thr Asp Ala Gly Gly Gln
                85                  90                  95

Leu Val Ile Glu Asp Asp Pro Asp Val Phe Val Lys Lys Trp Ala Phe
            100                 105                 110

Lys Glu Thr Ser Gly Ile Tyr Asp Leu Ser Leu Met Asp Ala Cys Gln
        115                 120                 125

Leu Leu Tyr Leu Tyr Asp Asn Asp His Thr Ser Thr
    130                 135                 140
```

<210> SEQ ID NO 28
<211> LENGTH: 915
<212> TYPE: DNA
<213> ORGANISM: Saccharomyces cerevisiae

<400> SEQUENCE: 28

```
atgaagatgt tgaggcgtac aaaggtaaat ttttcaaaat tgctttacaa gattactaaa    60
ctagcaatag tactgacgat cctatatatt tattttacgc ccaaaatcgt ctcccgaaac   120
aatgcatcat tgcagcatat ttttcctcat aaatatggcg attatgaaat caatttggtc   180
atagcgcacc ctgacgacga agttatgttt ttttccccca taatttctca actgaattcg   240
tactttccga gaaccgtccc atttaacata atctgcttat caagggcaa cgccgaaggt   300
cttggcgaaa ccagggtaag agaattaaat gagtcggccg ctttattgct acacaatgaa   360
agagcagtct ccgtacaggt gatggatttc caggatggta tggacgaaat atgggatatt   420
gattctataa cttcttctct ttcacaaaag atagatataa agaatcataa cttgaaccag   480
attatcgtta cctttgattc atatggtgta tcaaatcata tcaaccacaa aagctgttat   540
gctgccgtta aaaagttggt ggatgattat gctcaaccta agaccaaaag aaatgaacaa   600
```

```
ccacctcatg tcactgcgct ttatttgaga agctacaaga acaacatcgt tttaaagtac    660 aactcctta  tttgggaaat cctaaaaata ctttacgacc tgatttctcc attccgtaga    720
ataattcagg cgcttccgcc taacacagcc gccgaaaaag acaagctttc acttatgaat    780
acacatgcac aatacgtact agcgtttgcc actatgctaa atgctcacga atcccaagtt    840
gtgtggttta gatacggatg gtggatattt tccagatttg tcttcgttaa tgaatttgat    900
gtttatacat attag                                                    915
```

<210> SEQ ID NO 29
<211> LENGTH: 304
<212> TYPE: PRT
<213> ORGANISM: Saccharomyces cerevisiae

<400> SEQUENCE: 29

```
Met Lys Met Leu Arg Thr Lys Val Asn Phe Ser Lys Leu Leu Tyr
 1               5                  10                  15

Lys Ile Thr Lys Leu Ala Ile Val Leu Thr Ile Leu Tyr Ile Tyr Phe
            20                  25                  30

Thr Pro Lys Ile Val Ser Arg Asn Asn Ala Ser Leu Gln His Ile Phe
        35                  40                  45

Pro His Lys Tyr Gly Asp Tyr Glu Ile Asn Leu Val Ile Ala His Pro
    50                  55                  60

Asp Asp Glu Val Met Phe Phe Ser Pro Ile Ile Ser Gln Leu Asn Ser
65                  70                  75                  80

Tyr Phe Pro Arg Thr Val Pro Phe Asn Ile Ile Cys Leu Ser Lys Gly
                85                  90                  95

Asn Ala Glu Gly Leu Gly Glu Thr Arg Val Arg Glu Leu Asn Glu Ser
            100                 105                 110

Ala Ala Leu Leu Leu His Asn Glu Arg Ala Val Ser Val Gln Val Met
        115                 120                 125

Asp Phe Gln Asp Gly Met Asp Glu Ile Trp Asp Ile Asp Ser Ile Thr
    130                 135                 140

Ser Ser Leu Ser Gln Lys Ile Asp Ile Lys Asn His Asn Leu Asn Gln
145                 150                 155                 160

Ile Ile Val Thr Phe Asp Ser Tyr Gly Val Ser Asn His Ile Asn His
                165                 170                 175

Lys Ser Cys Tyr Ala Ala Val Lys Lys Leu Val Asp Tyr Ala Gln
            180                 185                 190

Pro Lys Thr Lys Arg Asn Glu Gln Pro Pro His Val Thr Ala Leu Tyr
        195                 200                 205

Leu Arg Ser Tyr Lys Asn Asn Ile Val Leu Lys Tyr Asn Ser Phe Ile
    210                 215                 220

Trp Glu Ile Leu Lys Ile Leu Tyr Asp Leu Ile Ser Pro Phe Arg Arg
225                 230                 235                 240

Ile Ile Gln Ala Leu Pro Pro Asn Thr Ala Ala Glu Lys Asp Lys Leu
                245                 250                 255

Ser Leu Met Asn Thr His Ala Gln Tyr Val Leu Ala Phe Ala Thr Met
            260                 265                 270

Leu Asn Ala His Glu Ser Gln Val Val Trp Phe Arg Tyr Gly Trp Trp
        275                 280                 285

Ile Phe Ser Arg Phe Val Phe Val Asn Glu Phe Asp Val Tyr Thr Tyr
    290                 295                 300
```

<210> SEQ ID NO 30
<211> LENGTH: 2760

<212> TYPE: DNA
<213> ORGANISM: Saccharomyces cerevisiae

<400> SEQUENCE: 30

```
atgtggaaca aaaccagaac gacgcttctg gctgttggtg tcttatttca tttattttac    60
ctatggtcta tttttgatat ctatttcatt tcaccgctcg ttcatggtat gagcccatat   120
caaagtactc caacccctcc tgcaaagaga ttgtttttga ttgtcggtga tggtttacgt   180
gcagatacca cttttgataa agtcactcat ccagtatccg gaaaaacaga atttctggca   240
ccttttatta gatctttggt aatgaataat gccacctacg gtatatcaca taccagaatg   300
ccaactgaat cccgtcctgg tcatgttgct atgattgctg ggttttacga agatgttagt   360
gccgtcacaa aaggttggaa gtcaaaccct gtcaatttcg atagtttttt caaccaatct   420
actcatactt attcattcgg ttcacctgac attttaccta tgttcaaaga tggcgcttct   480
gacccaaata aagttgacac ttggatgtat gatcatactt tcgaggattt tacgcaatct   540
tccatcgagc tggatgcttt tgtctttaga cacttggatc aattattcca caattccaca   600
ctgaactcaa cattggatta tgaaattagg caagacggta atgtattctt tctacatcta   660
ctaggttgcg atactgccgg acattcttat agaccatatt ctgccgagta ttatgacaat   720
gtcaaatata ttgatgatca aatccctatc cttatagaca aagtcaacaa gttttttgcg   780
gacgacaaaa ccgcatttat ttttacagca gatcatggta tgagtgcatt tggatcacat   840
ggtgacggtc atcctaacaa cacaaggacc cctcttgttg cttggggtgc gggtttgaat   900
aaaccagtac ataatccttt tccggtatcc gacaactata ctgaaaattg ggagctttcg   960
agcattaaaa gaaatgatgt caagcaagca gatattgctt ctttaatgtc atacttgatt  1020
ggtgtgaact atcctaaaaa ttcagttggt gagttaccaa tagcatatat cgatggaaaa  1080
gaaagtgaca agcttgccgc attgtacaac aacgcaagaa gcattttaga gcagtactta  1140
gtcaagcaag atgaggtaat agactctcaa tttttttata aggaatactt caagtttgtt  1200
gaaaagtctc attcacatta cttagaagag atagaaacct taattcagcg tatatctgaa  1260
ggagaaaact atttggaaca agaagcaatc acccttacag aggaattaat gcagataaca  1320
ttggaaggtt tacattattt gacaacctat aattggagat tcattagaac tattgttaca  1380
tttgggtttg ttgggtggat cttttttttct tttataatat ttttgaaatc attcatatta  1440
gagaatgtaa ttgatgacca aaaagcgtca ccattaagcc atgcagtatt tggttccata  1500
ggaattttac taaattggat tttgttctac caacattctc cgttcaattt ttacatgtac  1560
cttcttttcc cattatactt ttggagctat atttttacaa atagatccgt actacgttca  1620
ggtatcaagg aattcttcaa aggtacctct ccttggaaaa gagttttaat aacaatctct  1680
attatatcag tttatgaggg aattgtatat ggattttttcc atagatggac gtttacgcta  1740
attacaaata tattggcgtt ttacccgttt atttgtgggg tgagagagct atccgtgaat  1800
atattgtgga tcataactag tgttcttttta tctacattta ccttatttga cgctgttaaa  1860
attgaggact tgaaccagat acatctagca gggttattaa tcattctcag tgccttttat  1920
gctctttaca aaatacattc caggataaat tcctacacgc gtgctatatt tgccattcaa  1980
atttccttgg tggctgccat gttggcggtt actcatcgtt cagttatctc tttacagcta  2040
agacaagggt taccaagaga gtcacaggtc gctggatgga taatttttttt tgtatctctt  2100
tttgtaatgc caattttaca ttataggaag cccaacaatg attacaaagt gagattattg  2160
atcatttatt taaccttcgc accatccttt atcatttgda ctatatcatt cgaatcccdt  2220
ttctacttct tgttcactag ttacatggta caatggattg aaattgagaa caaaatcaaa  2280
```

-continued

```
gaaatgaaga cccaaaaaga tgaaaattgg ttacaagtgc taagagtttc agtaatcggg    2340 ttcttttac ttcaagtcgc attctttgga actggtaacg tcgcttcaat ctcttcattt     2400
tcattggagt ctgtttgtag attgttgcca attttgatc ctttcctgat gggcgcatta     2460
ttgatgttga aattgataat tccctacggg ctattgtcca catgcctagg tatactgaat    2520
ttaaaactta acttcaagga ctacacaatc tcatcattaa ttatttccat gagtgatatt    2580
ctgtcgttga atttttcta ccttttaaga acggagggt cgtggttgga tattggcata      2640
accatttcca actattgttt ggcgatccta tcatctttgt tcatgcttat tttggaagta    2700
ctcggtcatg tgttgctaaa aaatgtcatc atacaggata aaccaaaaa aacacaatag     2760
```

<210> SEQ ID NO 31
<211> LENGTH: 919
<212> TYPE: PRT
<213> ORGANISM: Saccharomyces cerevisiae

<400> SEQUENCE: 31

```
Met Trp Asn Lys Thr Arg Thr Leu Leu Ala Val Gly Val Leu Phe
 1               5                  10                  15

His Leu Phe Tyr Leu Trp Ser Ile Phe Asp Ile Tyr Phe Ile Ser Pro
                20                  25                  30

Leu Val His Gly Met Ser Pro Tyr Gln Ser Thr Pro Thr Pro Pro Ala
            35                  40                  45

Lys Arg Leu Phe Leu Ile Val Gly Asp Gly Leu Arg Ala Asp Thr Thr
        50                  55                  60

Phe Asp Lys Val Thr His Pro Val Ser Gly Lys Thr Glu Phe Leu Ala
 65                  70                  75                  80

Pro Phe Ile Arg Ser Leu Val Met Asn Asn Ala Thr Tyr Gly Ile Ser
                    85                  90                  95

His Thr Arg Met Pro Thr Glu Ser Arg Pro Gly His Val Ala Met Ile
                100                 105                 110

Ala Gly Phe Tyr Glu Asp Val Ser Ala Val Thr Lys Gly Trp Lys Ser
            115                 120                 125

Asn Pro Val Asn Phe Asp Ser Phe Phe Asn Gln Ser Thr His Thr Tyr
        130                 135                 140

Ser Phe Gly Ser Pro Asp Ile Leu Pro Met Phe Lys Asp Gly Ala Ser
145                 150                 155                 160

Asp Pro Asn Lys Val Asp Thr Trp Met Tyr Asp His Thr Phe Glu Asp
                165                 170                 175

Phe Thr Gln Ser Ser Ile Glu Leu Asp Ala Phe Val Phe Arg His Leu
            180                 185                 190

Asp Gln Leu Phe His Asn Ser Thr Leu Asn Ser Thr Leu Asp Tyr Glu
        195                 200                 205

Ile Arg Gln Asp Gly Asn Val Phe Phe Leu His Leu Leu Gly Cys Asp
    210                 215                 220

Thr Ala Gly His Ser Tyr Arg Pro Tyr Ser Ala Glu Tyr Tyr Asp Asn
225                 230                 235                 240

Val Lys Tyr Ile Asp Asp Gln Ile Pro Ile Leu Ile Asp Lys Val Asn
                245                 250                 255

Lys Phe Phe Ala Asp Asp Lys Thr Ala Phe Ile Phe Thr Ala Asp His
            260                 265                 270

Gly Met Ser Ala Phe Gly Ser His Gly Asp Gly His Pro Asn Asn Thr
        275                 280                 285

Arg Thr Pro Leu Val Ala Trp Gly Ala Gly Leu Asn Lys Pro Val His
```

```
            290                 295                 300
Asn Pro Phe Pro Val Ser Asp Asn Tyr Thr Glu Asn Trp Glu Leu Ser
305                 310                 315                 320

Ser Ile Lys Arg Asn Asp Val Lys Gln Ala Asp Ile Ala Ser Leu Met
                325                 330                 335

Ser Tyr Leu Ile Gly Val Asn Tyr Pro Lys Asn Ser Val Gly Glu Leu
                340                 345                 350

Pro Ile Ala Tyr Ile Asp Gly Lys Glu Ser Asp Lys Leu Ala Ala Leu
                355                 360                 365

Tyr Asn Asn Ala Arg Ser Ile Leu Glu Gln Tyr Leu Val Lys Gln Asp
370                 375                 380

Glu Val Ile Asp Ser Gln Phe Phe Tyr Lys Tyr Phe Lys Phe Val
385                 390                 395                 400

Glu Lys Ser His Ser His Tyr Leu Glu Glu Ile Glu Thr Leu Ile Gln
                405                 410                 415

Arg Ile Ser Glu Gly Glu Asn Tyr Leu Glu Gln Glu Ala Ile Thr Leu
                420                 425                 430

Thr Glu Glu Leu Met Gln Ile Thr Leu Glu Gly Leu His Tyr Leu Thr
                435                 440                 445

Thr Tyr Asn Trp Arg Phe Ile Arg Thr Ile Val Thr Phe Gly Phe Val
450                 455                 460

Gly Trp Ile Phe Phe Ser Phe Ile Ile Phe Leu Lys Ser Phe Ile Leu
465                 470                 475                 480

Glu Asn Val Ile Asp Asp Gln Lys Ala Ser Pro Leu Ser His Ala Val
                485                 490                 495

Phe Gly Ser Ile Gly Ile Leu Leu Asn Trp Ile Leu Phe Tyr Gln His
                500                 505                 510

Ser Pro Phe Asn Phe Tyr Met Tyr Leu Leu Phe Pro Leu Tyr Phe Trp
                515                 520                 525

Ser Tyr Ile Phe Thr Asn Arg Ser Val Leu Arg Ser Gly Ile Lys Glu
                530                 535                 540

Phe Phe Lys Gly Thr Ser Pro Trp Lys Arg Val Leu Ile Thr Ile Ser
545                 550                 555                 560

Ile Ile Ser Val Tyr Glu Gly Ile Val Tyr Gly Phe Phe His Arg Trp
                565                 570                 575

Thr Phe Thr Leu Ile Thr Asn Ile Leu Ala Phe Tyr Pro Phe Ile Cys
                580                 585                 590

Gly Val Arg Glu Leu Ser Val Asn Ile Leu Trp Ile Ile Thr Ser Val
                595                 600                 605

Leu Leu Ser Thr Phe Thr Leu Phe Asp Ala Val Lys Ile Glu Asp Leu
                610                 615                 620

Asn Gln Ile His Leu Ala Gly Leu Leu Ile Ile Leu Ser Ala Phe Tyr
625                 630                 635                 640

Ala Leu Tyr Lys Ile His Ser Arg Ile Asn Ser Tyr Thr Arg Ala Ile
                645                 650                 655

Phe Ala Ile Gln Ile Ser Leu Val Ala Ala Met Leu Ala Val Thr His
                660                 665                 670

Arg Ser Val Ile Ser Leu Gln Leu Arg Gln Gly Leu Pro Arg Glu Ser
                675                 680                 685

Gln Val Ala Gly Trp Ile Ile Phe Phe Val Ser Leu Phe Val Met Pro
                690                 695                 700

Ile Leu His Tyr Arg Lys Pro Asn Asn Asp Tyr Lys Val Arg Leu Leu
705                 710                 715                 720
```

```
Ile Ile Tyr Leu Thr Phe Ala Pro Ser Phe Ile Ile Leu Thr Ile Ser
            725                 730                 735

Phe Glu Ser Leu Phe Tyr Phe Leu Phe Thr Ser Tyr Met Val Gln Trp
            740                 745                 750

Ile Glu Ile Glu Asn Lys Ile Lys Glu Met Lys Thr Gln Lys Asp Glu
            755                 760                 765

Asn Trp Leu Gln Val Leu Arg Val Ser Val Ile Gly Phe Phe Leu Leu
        770                 775                 780

Gln Val Ala Phe Phe Gly Thr Gly Asn Val Ala Ser Ile Ser Ser Phe
785                 790                 795                 800

Ser Leu Glu Ser Val Cys Arg Leu Leu Pro Ile Phe Asp Pro Phe Leu
            805                 810                 815

Met Gly Ala Leu Leu Met Leu Lys Leu Ile Pro Tyr Gly Leu Leu
            820                 825                 830

Ser Thr Cys Leu Gly Ile Leu Asn Leu Lys Leu Asn Phe Lys Asp Tyr
            835                 840                 845

Thr Ile Ser Ser Leu Ile Ile Ser Met Ser Asp Ile Leu Ser Leu Asn
            850                 855                 860

Phe Phe Tyr Leu Leu Arg Thr Glu Gly Ser Trp Leu Asp Ile Gly Ile
865                 870                 875                 880

Thr Ile Ser Asn Tyr Cys Leu Ala Ile Leu Ser Ser Leu Phe Met Leu
            885                 890                 895

Ile Leu Glu Val Leu Gly His Val Leu Leu Lys Asn Val Ile Ile Gln
            900                 905                 910

Asp Lys Thr Lys Lys Thr Gln
            915

<210> SEQ ID NO 32
<211> LENGTH: 660
<212> TYPE: DNA
<213> ORGANISM: Saccharomyces cerevisiae

<400> SEQUENCE: 32
atgccagcta aaaaaggac tagaaagaca gtgaaaaaaa ccgtatcatt ctccgatgac       60
acaacattaa caacgcacca aaatcgtgag aaaaagaacg tagatcatga tcgtccacct      120
gtgtatgtga ggaaaacccc tctgatgaca tttccatacc atttagtagc actactttat      180
tactacgttt ttgtatcttc aaatttcaat acggtgaagt tgctaagttt tttgattcct      240
acacaagttg cttatttagt tttacaattc aataaatgca cagtttacgg taacaaaatc      300
attaagatca attactcatt gaccattatt tgtctaggtg ttacattttt gttgagcttt      360
cccacaatgt tattaactat attatttggt gcgccattaa tggacttatt gtgggaaacc      420
tggctgttgt cactgcattt tgcattttta gcatacccctg cagtttattc tgtatttaat      480
tgtgatttca aagtgggatt atggaagaag tattttatct ttatcgttgt aggggggttgg     540 attagttgtg ttgtcattcc tttggattgg gatagagatt ggcagaattg gccaattcct      600
attgttgttg gaggttattt gggcgctttg gtgggctata ctatcggtgc ctatatataa      660

<210> SEQ ID NO 33
<211> LENGTH: 219
<212> TYPE: PRT
<213> ORGANISM: Saccharomyces cerevisiae

<400> SEQUENCE: 33

Met Pro Ala Lys Lys Arg Thr Arg Lys Thr Val Lys Thr Val Ser
1               5                   10                  15
```

```
Phe Ser Asp Asp Thr Thr Leu Thr Thr His Gln Asn Arg Glu Lys Lys
             20                  25                  30

Asn Val Asp His Asp Arg Pro Pro Val Tyr Val Arg Lys Thr Pro Leu
         35                  40                  45

Met Thr Phe Pro Tyr His Leu Val Ala Leu Leu Tyr Tyr Tyr Val Phe
 50                  55                  60

Val Ser Ser Asn Phe Asn Thr Val Lys Leu Leu Ser Phe Leu Ile Pro
 65                  70                  75                  80

Thr Gln Val Ala Tyr Leu Val Leu Gln Phe Asn Lys Cys Thr Val Tyr
                 85                  90                  95

Gly Asn Lys Ile Ile Lys Ile Asn Tyr Ser Leu Thr Ile Ile Cys Leu
            100                 105                 110

Gly Val Thr Phe Leu Leu Ser Phe Pro Thr Met Leu Leu Thr Ile Leu
            115                 120                 125

Phe Gly Ala Pro Leu Met Asp Leu Leu Trp Glu Thr Trp Leu Leu Ser
130                 135                 140

Leu His Phe Ala Phe Leu Ala Tyr Pro Ala Val Tyr Ser Val Phe Asn
145                 150                 155                 160

Cys Asp Phe Lys Val Gly Leu Trp Lys Lys Tyr Phe Ile Phe Ile Val
                165                 170                 175

Val Gly Gly Trp Ile Ser Cys Val Val Ile Pro Leu Asp Trp Asp Arg
            180                 185                 190

Asp Trp Gln Asn Trp Pro Ile Pro Ile Val Val Gly Gly Tyr Leu Gly
        195                 200                 205

Ala Leu Val Gly Tyr Thr Ile Gly Ala Tyr Ile
        210                 215

<210> SEQ ID NO 34
<211> LENGTH: 2493
<212> TYPE: DNA
<213> ORGANISM: Saccharomyces cerevisiae

<400> SEQUENCE: 34
atgaacttga agcagttcac gtgcctatca tgcgctcaat tactcgctat tctgctcttt      60
atctttgctt tttccctag aaaaatcgtg ctgacaggta tatcaaagca agatccggat      120
caagaccgtg atctccagcg cgataggccc ttccagaaat tggtgttttgt gatcattgat     180 gctctcagat cagactttct ttttgattcg cagatttccc acttcaacaa cgtgcaccaa     240
tggctcaata cgggcgaagc atggggttac acgtcatttg ctaatccgcc taccgtgacg     300
ctgcctagac tcaaaagtat tactacggga tctacaccta gcttcattga cttgctgctg     360
aatgtagccc aggacataga ttccaacgat ctttcggagc acgattcctg ctgcagcag      420 ttcatccaac ataataacac gattcgtttc atgggcgatg acacctggct gaaactgttc     480
ccacagcaat ggtttgactt cgctgacccg acacactcgt tctttgtcag tgatttcact     540
caagtcgata taatgtgac gaggaacttg cccgggaaat tatttcagga atgggcccag      600
tgggacgtgg ctatcctgca ttacttgggt cttgaccata tcgggcataa agatggcccg     660
cattcaaagt ttatggctgc taaacatcaa gaaatggaca gcattctgaa gtcaatatat     720
gatgaagtgt tggaacatga agatgacgat gatacactga tttgtgttct tggcgaccat     780
ggaatgaacg aactgggcaa ccatggtggc tcttcagccg cgaaacatc agcaggattg      840 ttgttttttgt cacctaagct ggcgcaattt gctaggccag aatcgcaagt aaactacaca    900
ttgcccatca acgctagtcc ggactggaat ttccagtatt tagagactgt tcaacaaatt     960
gatatcgtcc ccaccatagc agcactgttt ggtatgccaa tccccatgaa cagtgttggg   1020
```

-continued

```
ataataatac ctgactttt acaactgttg cccaataagt tggcaagtat gaaagaaaat    1080
tttatgcatt tgtggaaatt atcagaccat cacggcgagg ttgctcttga cgatttcact    1140
gccgaagata tttatacaaa gatgtacact attcaagaaa cgttaaccaa gtctgcaaca    1200
aattataatt atcctctttt gacactggct tttgttggtt tcctcataat aacaatcatc    1260
gccatttatg tattattacg ttattctggg cctgattttt ggcagttgcg cgtttcttcc    1320
ctgtctgttc tgttagtttc cattatacta ggcgtttcca catttgcaag tagtttcatt    1380
gaagaggagc accaactgtg gtggtggata gtaactgcat tctcggcggt ccctctgttc    1440
gtataccgat tgaatgtgct cataatcgtg cgctggttta atgatggc atgcgtacgc      1500
tcaatcaagt tttggaataa cagtggccag aaattcattt attctaacgt tatgtccaat    1560
ctacttaatc agaatccttc ctggaagtgg tgcttaaata tgttgacatt tctagtgctg    1620
ataatggcat ctgctggttt tcaagtacta catttattg tcactactat tttggtgggg     1680
ttgtgtttca cgtacaaaat ctcgtgggaa atcgtcaatg gtaaccaggc agaaataccg    1740
ctctttatgc atgatttact ggctaagata gactttgcac caactgaaag taacttgatt    1800
gtacttgcgc gcgttttctt ccaagcttgg gctattgttg tcatttcaag gttggtcctg    1860
acgaaattga agtacttaa caagaactac ctcattaaag atatgaaagt ttatataaca     1920
attcttttga tgttccaaac ttcttctcag aacataggtc aatttctcgt tttccaaata    1980
ttagagtccc aaatttttta cttttttccaa atatattccaa ccgcctcatt aacatcaaca  2040
agtaagattt atttttcgaa tttggtgtcc ttaattttac aaaattttac attttttccaa   2100
ttcggtggca caaattccat ttctactata gaccttggaa acgcatacca tggtgtttcc    2160
tcagactaca acatctacgt agtggggata ttaatgtccg ttgccaattt cgcgccggca    2220
atatactggt ccatgctacc gtggtcaata aactacgcct ctattccagc acaagttaag    2280
ttgcaaacgt tcatcagaag taagttacct gccttcacct atcattgtat atttggaact    2340
tgtttgatga cggcatgcgt cgttttgaga tttcatctct ttatttggtc cgttttcagt    2400
ccaaaattat gttatttcct tgggtggaat tttgtgatgg gattgctgaa tggctggtta    2460
cctgaattgg ccctcctttg cgctcttgat taa                                 2493
```

<210> SEQ ID NO 35
<211> LENGTH: 830
<212> TYPE: PRT
<213> ORGANISM: Saccharomyces cerevisiae

<400> SEQUENCE: 35

```
Met Asn Leu Lys Gln Phe Thr Cys Leu Ser Cys Ala Gln Leu Leu Ala
 1               5                  10                  15

Ile Leu Leu Phe Ile Phe Ala Phe Phe Pro Arg Lys Ile Val Leu Thr
            20                  25                  30

Gly Ile Ser Lys Gln Asp Pro Asp Gln Asp Arg Asp Leu Gln Arg Asp
        35                  40                  45

Arg Pro Phe Gln Lys Leu Val Phe Val Ile Asp Ala Leu Arg Ser
    50                  55                  60

Asp Phe Leu Phe Asp Ser Gln Ile Ser His Phe Asn Asn Val His Gln
65                  70                  75                  80

Trp Leu Asn Thr Gly Glu Ala Trp Gly Tyr Thr Ser Phe Ala Asn Pro
                85                  90                  95

Pro Thr Val Thr Leu Pro Arg Leu Lys Ser Ile Thr Thr Gly Ser Thr
            100                 105                 110
```

-continued

```
Pro Ser Phe Ile Asp Leu Leu Asn Val Ala Gln Asp Ile Asp Ser
        115                 120                 125
Asn Asp Leu Ser Glu His Asp Ser Trp Leu Gln Gln Phe Ile Gln His
130                 135                 140
Asn Asn Thr Ile Arg Phe Met Gly Asp Thr Trp Leu Lys Leu Phe
145                 150                 155                 160
Pro Gln Gln Trp Phe Asp Phe Ala Asp Pro Thr His Ser Phe Phe Val
                    165                 170                 175
Ser Asp Phe Thr Gln Val Asp Asn Asn Val Thr Arg Asn Leu Pro Gly
                180                 185                 190
Lys Leu Phe Gln Glu Trp Ala Gln Trp Asp Val Ala Ile Leu His Tyr
            195                 200                 205
Leu Gly Leu Asp His Ile Gly His Lys Asp Gly Pro His Ser Lys Phe
        210                 215                 220
Met Ala Ala Lys His Gln Glu Met Asp Ser Ile Leu Lys Ser Ile Tyr
225                 230                 235                 240
Asp Glu Val Leu Glu His Asp Asp Asp Thr Leu Ile Cys Val
                    245                 250                 255
Leu Gly Asp His Gly Met Asn Glu Leu Gly Asn His Gly Gly Ser Ser
                260                 265                 270
Ala Gly Glu Thr Ser Ala Gly Leu Leu Phe Leu Ser Pro Lys Leu Ala
            275                 280                 285
Gln Phe Ala Arg Pro Glu Ser Gln Val Asn Tyr Thr Leu Pro Ile Asn
        290                 295                 300
Ala Ser Pro Asp Trp Asn Phe Gln Tyr Leu Glu Thr Val Gln Gln Ile
305                 310                 315                 320
Asp Ile Val Pro Thr Ile Ala Ala Leu Phe Gly Met Pro Ile Pro Met
                    325                 330                 335
Asn Ser Val Gly Ile Ile Pro Asp Phe Leu Gln Leu Leu Pro Asn
                340                 345                 350
Lys Leu Ala Ser Met Lys Glu Asn Phe Met His Leu Trp Lys Leu Ser
            355                 360                 365
Asp His His Gly Glu Val Ala Leu Asp Asp Phe Thr Ala Glu Asp Ile
        370                 375                 380
Tyr Thr Lys Met Tyr Thr Ile Gln Glu Thr Leu Thr Lys Ser Ala Thr
385                 390                 395                 400
Asn Tyr Asn Tyr Pro Leu Leu Thr Leu Ala Phe Val Gly Phe Leu Ile
                    405                 410                 415
Ile Thr Ile Ile Ala Ile Tyr Val Leu Leu Arg Tyr Ser Gly Pro Asp
                420                 425                 430
Phe Trp Gln Leu Arg Val Ser Ser Leu Ser Val Leu Leu Val Ser Ile
            435                 440                 445
Ile Leu Gly Val Ser Thr Phe Ala Ser Ser Phe Ile Glu Glu His
        450                 455                 460
Gln Leu Trp Trp Trp Ile Val Thr Ala Phe Ser Ala Val Pro Leu Phe
465                 470                 475                 480
Val Tyr Arg Leu Asn Val Leu Ile Val Arg Trp Phe Ile Met Met
                    485                 490                 495
Ala Cys Val Arg Ser Ile Lys Phe Trp Asn Asn Ser Gly Gln Lys Phe
                500                 505                 510
Ile Tyr Ser Asn Val Met Ser Asn Leu Leu Asn Gln Asn Pro Ser Trp
            515                 520                 525
Lys Trp Cys Leu Asn Met Leu Thr Phe Leu Val Leu Ile Met Ala Ser
        530                 535                 540
```

Ala Gly Phe Gln Val Leu His Phe Ile Val Thr Thr Ile Leu Val Gly
545                 550                 555                 560

Leu Cys Phe Thr Tyr Lys Ile Ser Trp Glu Ile Val Asn Gly Asn Gln
                565                 570                 575

Ala Glu Ile Pro Leu Phe Met His Asp Leu Leu Ala Lys Ile Asp Phe
            580                 585                 590

Ala Pro Thr Glu Ser Asn Leu Ile Val Leu Ala Arg Val Phe Phe Gln
        595                 600                 605

Ala Trp Ala Ile Val Val Ile Ser Arg Leu Val Leu Thr Lys Leu Lys
610                 615                 620

Val Leu Asn Lys Asn Tyr Leu Ile Lys Asp Met Lys Val Tyr Ile Thr
625                 630                 635                 640

Ile Leu Leu Met Phe Gln Thr Ser Ser Gln Asn Ile Gly Gln Phe Leu
                645                 650                 655

Val Phe Gln Ile Leu Glu Ser Gln Ile Phe Tyr Phe Gln Asn Ile
            660                 665                 670

Pro Thr Ala Ser Leu Thr Ser Thr Ser Lys Ile Tyr Phe Ser Asn Leu
        675                 680                 685

Val Ser Leu Ile Leu Gln Asn Phe Thr Phe Gln Phe Gly Gly Thr
690                 695                 700

Asn Ser Ile Ser Thr Ile Asp Leu Gly Asn Ala Tyr His Gly Val Ser
705                 710                 715                 720

Ser Asp Tyr Asn Ile Tyr Val Val Gly Ile Leu Met Ser Val Ala Asn
                725                 730                 735

Phe Ala Pro Ala Ile Tyr Trp Ser Met Leu Pro Trp Ser Ile Asn Tyr
            740                 745                 750

Ala Ser Ile Pro Ala Gln Val Lys Leu Gln Thr Phe Ile Arg Ser Lys
        755                 760                 765

Leu Pro Ala Phe Thr Tyr His Cys Ile Phe Gly Thr Cys Leu Met Thr
770                 775                 780

Ala Cys Val Val Leu Arg Phe His Leu Phe Ile Trp Ser Val Phe Ser
785                 790                 795                 800

Pro Lys Leu Cys Tyr Phe Leu Gly Trp Asn Phe Val Met Gly Leu Leu
                805                 810                 815

Asn Gly Trp Leu Pro Glu Leu Ala Leu Leu Cys Ala Leu Asp
            820                 825                 830

<210> SEQ ID NO 36
<211> LENGTH: 1605
<212> TYPE: DNA
<213> ORGANISM: Saccharomyces cerevisiae

<400> SEQUENCE: 36
atgtccaatg caaatctaag aaaatgggtt ggttttttgct tgttgccat ttatctcttt        60 ttaggtgttc cactgtggta caagctaact acagtttata gagcatcact accaataaat      120
tacattgagt cacttcaaaa taacaaattc caagatattc atctcgtaat accggtgtat      180
gttaagtcag atacttacag atttcctgac gttcatgacg ctatccaagt acaagttaac      240
catttattga attctcagga gcaacgggtc ccttggtctt acaagttct tccatataat      300 gagactattg agcagatgga aagtgaaggc aaccagtttc atgtcgttac ttgaagtta      360 gacgaattta ttggttactc atcagcttac gacaccaaag aaacactagt atattacgac      420
gatgctgccg ttttaagtaa tgatctaccg ttttttgttg ctcaaacatt ggtagagcac      480
actttccaat tggaatggac gcatttgaat aaaacgtgtg aaggcgtttc tacaaacaac      540

```
gatgtcgcaa tatcttatga tccaaacatt catttaagtg taactttatt gtcaggtgat      600
gggaatcctg ttgcatggga aattgagcct acattaactg actactttc acctttagg       660 aagttcttat caccactggt aaattttaca gtagattcat ccattgttta tcataatgat     720
ttgaatttgc attcattaaa tggatcatgt acaagcgtta cgtggtttga tctctctcat     780
actattgatc tttctgaact ttcttcaatg gcctattacc cagaagattc tgcactgaat     840
ttagccatag tctttcctag tgcttcttca gtcccgatg gtctggcgtt cattaatggc      900
actcggattt cagacgaaat aaccacatta gattggaata gttatctagt tcctcaatgg     960
ggggttataa taataaataa aatgccgttg aagccaaatt cagtcattag cgaagattat    1020
ttagaaccta tgatgtaccg ttttgcgaca gatattttc aactattggg attaacggag     1080
ggctcgcaag atttgttatc acctatatt accatagatt cattcaaaag gttgacaatt     1140
ttacagaatc tagataaagc tacgaaaaca ttatggtcgt tagtgaaatt aactcaacaa    1200
tttcagggca tgtctatccc acgcgaagta tcggataatg ttatcgaagc tttagactta    1260
aggctacaga ttattgattt attaaatgat cctggaaagg gtggagatat cgtctggaac    1320
aatgccctgc atctaagtaa tgaattggtt aaactatgcg aaaaggcatt ttcaatgga     1380 gaaatggttc aacaaaattt cttcccacaa gagcacatga tagctgtgta tttacctta    1440 ttaggcccaa tatcggcagt catgttcttt ggtttctaca acgtgatgaa ggaaaagaat    1500
caaaagagta aaagaatgg aaccgagaga gaagttgcta agaaaaatt agagttgaaa      1560 gaggctcaaa aattacatgc tattgatggt gaagatgaat tatga                    1605
```

<210> SEQ ID NO 37
<211> LENGTH: 534
<212> TYPE: PRT
<213> ORGANISM: Saccharomyces cerevisiae

<400> SEQUENCE: 37

```
Met Ser Asn Ala Asn Leu Arg Lys Trp Val Gly Phe Cys Phe Val Ala
1               5                   10                  15

Ile Tyr Leu Phe Leu Gly Val Pro Leu Trp Tyr Lys Leu Thr Thr Val
            20                  25                  30

Tyr Arg Ala Ser Leu Pro Ile Asn Tyr Ile Glu Ser Leu Gln Asn Asn
        35                  40                  45

Lys Phe Gln Asp Ile His Leu Val Ile Pro Val Tyr Val Lys Ser Asp
    50                  55                  60

Thr Tyr Arg Phe Pro Asp Val His Asp Ala Ile Gln Val Gln Val Asn
65                  70                  75                  80

His Leu Leu Asn Ser Gln Glu Gln Arg Val Pro Trp Ser Leu Gln Val
                85                  90                  95

Leu Pro Tyr Asn Glu Thr Ile Glu Gln Met Glu Ser Glu Gly Asn Gln
            100                 105                 110

Phe His Val Val Thr Leu Lys Leu Asp Glu Phe Ile Gly Tyr Ser Ser
        115                 120                 125

Ala Tyr Asp Thr Lys Glu Thr Leu Val Tyr Tyr Asp Asp Ala Ala Val
    130                 135                 140

Leu Ser Asn Asp Leu Pro Phe Phe Val Ala Gln Thr Leu Val Glu His
145                 150                 155                 160

Thr Phe Gln Leu Glu Trp Thr His Leu Asn Lys Thr Cys Glu Gly Val
                165                 170                 175

Ser Thr Asn Asn Asp Val Ala Ile Ser Tyr Asp Pro Asn Ile His Leu
            180                 185                 190
```

Ser Val Thr Leu Leu Ser Gly Asp Gly Asn Pro Val Ala Trp Glu Ile
        195                 200                 205

Glu Pro Thr Leu Thr Asp Tyr Phe Ser Pro Phe Arg Lys Phe Leu Ser
    210                 215                 220

Pro Leu Val Asn Phe Thr Val Asp Ser Ser Ile Val Tyr His Asn Asp
225                 230                 235                 240

Leu Asn Leu His Ser Leu Asn Gly Ser Cys Thr Ser Val Thr Trp Phe
                245                 250                 255

Asp Leu Ser His Thr Ile Asp Leu Ser Glu Leu Ser Ser Met Ala Tyr
            260                 265                 270

Tyr Pro Glu Asp Ser Ala Leu Asn Leu Ala Ile Val Phe Pro Ser Ala
        275                 280                 285

Ser Ser Ser Pro Asp Gly Leu Ala Phe Ile Asn Gly Thr Arg Ile Ser
    290                 295                 300

Asp Glu Ile Thr Thr Leu Asp Trp Asn Ser Tyr Leu Val Pro Gln Trp
305                 310                 315                 320

Gly Val Ile Ile Ile Asn Lys Met Pro Leu Lys Pro Asn Ser Val Ile
                325                 330                 335

Ser Glu Asp Tyr Leu Glu Pro Met Met Tyr Arg Phe Ala Thr Asp Ile
            340                 345                 350

Phe Gln Leu Leu Gly Leu Thr Glu Gly Ser Gln Asp Leu Leu Ser Pro
        355                 360                 365

Tyr Ile Thr Ile Asp Ser Phe Lys Arg Leu Thr Ile Leu Gln Asn Leu
    370                 375                 380

Asp Lys Ala Thr Glu Thr Leu Trp Ser Leu Val Lys Leu Thr Gln Gln
385                 390                 395                 400

Phe Gln Gly Met Ser Ile Pro Arg Glu Val Ser Asp Asn Val Ile Glu
                405                 410                 415

Ala Leu Asp Leu Arg Leu Gln Ile Ile Asp Leu Leu Asn Asp Pro Gly
            420                 425                 430

Lys Gly Gly Asp Ile Val Trp Asn Asn Ala Leu His Leu Ser Asn Glu
        435                 440                 445

Leu Val Lys Leu Cys Glu Lys Ala Phe Phe Asn Gly Glu Met Val Gln
    450                 455                 460

Gln Asn Phe Phe Pro Gln Glu His Met Ile Ala Val Tyr Leu Pro Leu
465                 470                 475                 480

Leu Gly Pro Ile Ser Ala Val Met Phe Phe Gly Phe Tyr Asn Val Met
                485                 490                 495

Lys Glu Lys Asn Gln Lys Ser Lys Lys Asn Gly Thr Glu Arg Glu Val
            500                 505                 510

Ala Lys Glu Lys Leu Glu Leu Lys Glu Ala Gln Lys Leu His Ala Ile
        515                 520                 525

Asp Gly Glu Asp Glu Leu
    530

<210> SEQ ID NO 38
<211> LENGTH: 1833
<212> TYPE: DNA
<213> ORGANISM: Saccharomyces cerevisiae

<400> SEQUENCE: 38
atgatcctca cactggccta tttcatgctg ggcactctac tactgggtgt gttcgcagaa      60
gacacggtgt cgcagattgg tataaatgac agtttatggt atccgtacga cgaagcactg     120
gtgttgaagc cgctgcccaa caatgatctg ctactctcat ttgcattcca actgcaatcg     180

```
gaaccgtttg acccggccgt atcatccatg tcatatgatg cgtatgagca ctacacgact    240
ttcccacggg ccatcccacc attgttggaa tctactgcca cgcgtcagtt tcatttaaga    300
tttaccagag gattctggga tgccctgtcg tggggacagt tgccacatgc tggaaaagag    360
gcaggtgcct caggtgtgga attgtggtcg caagtgcagg ccatggatca ggaacaggcg    420
ttccataatt ggaaaaaact gtccaattca ttgagcggat tgttttgttc ttctttaaat    480
tttatcgacg agtcaaggac gacctttccc cggcggtcat atgcttctga tataggagct    540
cctcttttca atagcaccga gaaactgtac ctgatgcgag catcgttgcc caatgaaccc    600
atctgtaccg agaacttgac gccgttcata aaactattgc ctactagggg caaatccggt    660
ttgacatctc tcttggatgg tcataaattg ttcgactctc tatggaatag tatttccttg    720
gatattgcca ctatttgttc tgaagatgaa gatgctcttt gtcactacga gatggacgca    780
cgcatagaaa tggtaacaca cgttccctcc gccttggcaa gaggtgagag acctatcccc    840
aaacctttgg atgggaacac attgcgttgt gacacggata acccctttga ttcttaccaa    900
tgcttccctc taccggaacc ttcgcagact cacttcaagc tgtctcagct gtttgccaga    960
ccaataaaca atggcaacct gtttgctaat aggcccacaa gaatttgtgc agaagttgac   1020
cgttctacct ggactgcgtt tttgtcagtt gacgatacta ttttcagcac acatgataat   1080
tgctttgact tatcaaacga tcaaaatgag ggtggttcgg gctacgactt tattttagaa   1140
tcgacggaca ctactaaagt tactcccata gttcctgtcc caattcacgt aagcagatct   1200
ctgactggta tggacaaga tcgtggtgga atgcgtattg ttttccataa cgacaatgat   1260
accctgtga agttgattta tttcgaatca ttgccatggt tcatgagagt ttacctatcc   1320
tctcttcaaa ttacttctac tacctctccg caattgcaag aaaacgatat catcttagat   1380
aaatactatt tacaagcggc cgatagaaaa agacctggcc acttggagtt cacgatgtta   1440
attccagcta atacgacat tgtaatgact tatcaattcg ataaagctct tctgcaattt   1500
gccgagtatc caccagatgc aaaccatggt tttgaaatcg atgcagctgt aatcaccgtg   1560
ctatctttgg agtcctcatc gtctctttat gaaatgagaa cctctaccct attgttatcc   1620
ctgtctacac cggatttag tatgccgtat aacgtcatca ttctaacatc tacaatcatg   1680
ggactcatat tcggtatgct atacaatttg atggtgaaga gaatggtcac cgtcgaagag   1740
gccgataaga ttacgttgca atctggctta aaatacaaat tgctaaagct aaaggaaaag   1800
ttcctaggga aaaaaagac taaaacagac taa                                 1833
```

<210> SEQ ID NO 39
<211> LENGTH: 610
<212> TYPE: PRT
<213> ORGANISM: Saccharomyces cerevisiae

<400> SEQUENCE: 39

Met Ile Leu Thr Leu Ala Tyr Phe Met Leu Gly Thr Leu Leu Leu Gly
1               5                   10                  15

Val Phe Ala Glu Asp Thr Val Ser Gln Ile Gly Ile Asn Asp Ser Leu
            20                  25                  30

Trp Tyr Pro Tyr Asp Glu Ala Leu Val Leu Lys Pro Leu Pro Asn Asn
        35                  40                  45

Asp Leu Leu Leu Ser Phe Ala Phe Gln Leu Gln Ser Glu Pro Phe Asp
    50                  55                  60

Pro Ala Val Ser Ser Met Ser Tyr Asp Ala Tyr Glu His Tyr Thr Thr
65                  70                  75                  80

-continued

```
Phe Pro Arg Ala Ile Pro Pro Leu Leu Glu Ser Thr Ala Thr Arg Gln
                85                  90                  95
Phe His Leu Arg Phe Thr Arg Gly Phe Trp Asp Ala Leu Ser Trp Gly
            100                 105                 110
Gln Leu Pro His Ala Gly Lys Glu Ala Gly Ala Ser Gly Val Glu Leu
        115                 120                 125
Trp Ser Gln Val Gln Ala Met Asp Gln Glu Gln Ala Phe His Asn Trp
    130                 135                 140
Lys Lys Leu Ser Asn Ser Leu Ser Gly Leu Phe Cys Ser Ser Leu Asn
145                 150                 155                 160
Phe Ile Asp Glu Ser Arg Thr Thr Phe Pro Arg Arg Ser Tyr Ala Ser
                165                 170                 175
Asp Ile Gly Ala Pro Leu Phe Asn Ser Thr Glu Lys Leu Tyr Leu Met
            180                 185                 190
Arg Ala Ser Leu Pro Asn Glu Pro Ile Cys Thr Glu Asn Leu Thr Pro
        195                 200                 205
Phe Ile Lys Leu Leu Pro Thr Arg Gly Lys Ser Gly Leu Thr Ser Leu
    210                 215                 220
Leu Asp Gly His Lys Leu Phe Asp Ser Leu Trp Asn Ser Ile Ser Leu
225                 230                 235                 240
Asp Ile Ala Thr Ile Cys Ser Glu Asp Glu Asp Ala Leu Cys His Tyr
                245                 250                 255
Glu Met Asp Ala Arg Ile Glu Met Val Thr His Val Pro Ser Ala Leu
            260                 265                 270
Ala Arg Gly Glu Arg Pro Ile Pro Lys Pro Leu Asp Gly Asn Thr Leu
        275                 280                 285
Arg Cys Asp Thr Asp Lys Pro Phe Asp Ser Tyr Gln Cys Phe Pro Leu
    290                 295                 300
Pro Glu Pro Ser Gln Thr His Phe Lys Leu Ser Gln Leu Phe Ala Arg
305                 310                 315                 320
Pro Ile Asn Asn Gly Asn Leu Phe Ala Asn Arg Pro Thr Arg Ile Cys
                325                 330                 335
Ala Glu Val Asp Arg Ser Thr Trp Thr Ala Phe Leu Ser Val Asp Asp
            340                 345                 350
Thr Ile Phe Ser Thr His Asp Asn Cys Phe Asp Leu Ser Asn Asp Gln
        355                 360                 365
Asn Glu Gly Gly Ser Gly Tyr Asp Phe Ile Leu Glu Ser Thr Asp Thr
    370                 375                 380
Thr Lys Val Thr Pro Ile Val Pro Val Pro Ile His Val Ser Arg Ser
385                 390                 395                 400
Leu Thr Gly Asn Gly Gln Asp Arg Gly Gly Met Arg Ile Val Phe His
                405                 410                 415
Asn Asp Asn Asp Thr Pro Val Lys Leu Ile Tyr Phe Glu Ser Leu Pro
            420                 425                 430
Trp Phe Met Arg Val Tyr Leu Ser Ser Leu Gln Ile Thr Ser Thr Thr
        435                 440                 445
Ser Pro Gln Leu Gln Glu Asn Asp Ile Ile Leu Asp Lys Tyr Tyr Leu
    450                 455                 460
Gln Ala Ala Asp Arg Lys Arg Pro Gly His Leu Glu Phe Thr Met Leu
465                 470                 475                 480
Ile Pro Ala Asn Thr Asp Ile Val Met Thr Tyr Gln Phe Asp Lys Ala
                485                 490                 495
Leu Leu Gln Phe Ala Glu Tyr Pro Pro Asp Ala Asn His Gly Phe Glu
            500                 505                 510
```

Ile Asp Ala Ala Val Ile Thr Val Leu Ser Leu Glu Ser Ser Ser
        515                 520                 525

Leu Tyr Glu Met Arg Thr Ser Thr Leu Leu Leu Ser Leu Ser Thr Pro
    530                 535                 540

Asp Phe Ser Met Pro Tyr Asn Val Ile Ile Leu Thr Ser Thr Ile Met
545                 550                 555                 560

Gly Leu Ile Phe Gly Met Leu Tyr Asn Leu Met Val Lys Arg Met Val
                565                 570                 575

Thr Val Glu Glu Ala Asp Lys Ile Thr Leu Gln Ser Gly Leu Lys Tyr
            580                 585                 590

Lys Leu Leu Lys Leu Lys Glu Lys Phe Leu Gly Lys Lys Lys Thr Lys
    595                 600                 605

Thr Asp
    610

<210> SEQ ID NO 40
<211> LENGTH: 1185
<212> TYPE: DNA
<213> ORGANISM: Saccharomyces cerevisiae

<400> SEQUENCE: 40
atggattcca cagcacttaa ggtagctcta ggctgtattg caattcgttt ggctgtgaac      60 agccttttc cctctctaca acaacaactg gaccagtctg tagaattctc aactcccgta     120
acttcattta ggtcactaca ggaaggtata tacctactgc ggaacaacat ccaagtatat     180
aatcatgggg ttgttcacca tcctccaatt ttgatttttt ttctttccct ctttaattcc     240
gacaggttaa tttccctcat atacgcttta attgatggat taattgcgta tcagctgaca     300
gaggtaacaa aggctttcaa aaacttgaaa ctgaaagttt ggctacctgg acttctttat     360
gccgtgaatc ctttgacccct tttatcgtgc attagtcggt catcaatcat attcacaaat     420
tttgctattt catcgtcatt gtattgcata ttagctgaag aaacgttct tttgtcctct     480 gttatgattt ctatatctgg atatttgtca gtatacccta ttctcctctt aattccgcta     540
ttaggtatgc tgaaaagttg gaggcaaaga atattatctg ccattgtttc catactatct     600
ttattaattc tgctattatt cagctacagt atattaggca gccaaagttg gtcattttg     660 acacaggttt atggatctat tataaccttt gagaaggttt ttccaaatct gggtttgtgg     720
tggtacttct tcattgaaat gtttgacacc ttcataccgt tcttcaaggc tgtattcaac     780 attttattg cagtattcat tacaccattt actttgcgct atcataagca gccattctac     840
gcattcattt tatgcattgg gtggattgtc cttacaaagc catatccctc actaggtgac     900
gctggttttt tcttcagctt cctacctttc ttcacgccac tatttggata tttaagatac     960
cccatcatat cagcattact gtttttacac gcaattgttt tggcgccaat tttctatcat    1020
ctttgggttg ttttaggttc agggaatagt aattttttct atgctatttc cctagtttat    1080
gctctggcta tagcatctat attagttgac ttgaactggg cgatgctgag aattgaatac    1140
gataacggta tcccaaatttt caaattgaag gtaacacaaa tttaa                   1185

<210> SEQ ID NO 41
<211> LENGTH: 394
<212> TYPE: PRT
<213> ORGANISM: Saccharomyces cerevisiae

<400> SEQUENCE: 41

Met Asp Ser Thr Ala Leu Lys Val Ala Leu Gly Cys Ile Ala Ile Arg
1               5                   10                  15

Leu Ala Val Asn Ser Leu Phe Pro Ser Leu Gln Gln Gln Leu Asp Gln
            20                  25                  30

Ser Val Glu Phe Ser Thr Pro Val Thr Ser Phe Arg Ser Leu Gln Glu
            35                  40                  45

Gly Ile Tyr Leu Leu Arg Asn Asn Ile Gln Val Tyr Asn His Gly Val
        50                  55                  60

Val His His Pro Pro Ile Leu Ile Phe Phe Leu Ser Leu Phe Asn Ser
65                  70                  75                  80

Asp Arg Leu Ile Ser Leu Ile Tyr Ala Leu Ile Asp Gly Leu Ile Ala
                85                  90                  95

Tyr Gln Leu Thr Glu Val Thr Lys Ala Phe Lys Asn Leu Lys Leu Lys
            100                 105                 110

Val Trp Leu Pro Gly Leu Leu Tyr Ala Val Asn Pro Leu Thr Leu Leu
        115                 120                 125

Ser Cys Ile Ser Arg Ser Ser Ile Ile Phe Thr Asn Phe Ala Ile Ser
    130                 135                 140

Ser Ser Leu Tyr Cys Ile Leu Ala Glu Gly Asn Val Leu Leu Ser Ser
145                 150                 155                 160

Val Met Ile Ser Ile Ser Gly Tyr Leu Ser Val Tyr Pro Ile Leu Leu
                165                 170                 175

Leu Ile Pro Leu Leu Gly Met Leu Lys Ser Trp Arg Gln Arg Ile Leu
            180                 185                 190

Ser Ala Ile Val Ser Ile Leu Ser Leu Leu Ile Leu Leu Leu Phe Ser
        195                 200                 205

Tyr Ser Ile Leu Gly Ser Gln Ser Trp Ser Phe Leu Thr Gln Val Tyr
    210                 215                 220

Gly Ser Ile Ile Thr Phe Glu Lys Val Phe Pro Asn Leu Gly Leu Trp
225                 230                 235                 240

Trp Tyr Phe Phe Ile Glu Met Phe Asp Thr Phe Ile Pro Phe Phe Lys
                245                 250                 255

Ala Val Phe Asn Ile Phe Ile Ala Val Phe Ile Thr Pro Phe Thr Leu
            260                 265                 270

Arg Tyr His Lys Gln Pro Phe Tyr Ala Phe Ile Leu Cys Ile Gly Trp
        275                 280                 285

Ile Val Leu Thr Lys Pro Tyr Pro Ser Leu Gly Asp Ala Gly Phe Phe
    290                 295                 300

Phe Ser Phe Leu Pro Phe Phe Thr Pro Leu Phe Gly Tyr Leu Arg Tyr
305                 310                 315                 320

Pro Ile Ile Ser Ala Leu Leu Phe Leu His Ala Ile Val Leu Ala Pro
                325                 330                 335

Ile Phe Tyr His Leu Trp Val Val Leu Gly Ser Gly Asn Ser Asn Phe
            340                 345                 350

Phe Tyr Ala Ile Ser Leu Val Tyr Ala Leu Ala Ile Ala Ser Ile Leu
        355                 360                 365

Val Asp Leu Asn Trp Ala Met Leu Arg Ile Glu Tyr Asp Asn Gly Ile
    370                 375                 380

Pro Asn Phe Lys Leu Lys Val Thr Gln Ile
385                 390

<210> SEQ ID NO 42
<211> LENGTH: 255
<212> TYPE: DNA
<213> ORGANISM: Homo sapiens

<400> SEQUENCE: 42

```
atggccacgg ggacagacca ggtggtggga ctcggcctcg tcgccgttag cctgatcatc      60 ttcaccctact acaccgcctg ggtgattctc ttgccattca tcgacagtca gcatgtcatc    120
cacaagtatt tcctgccccg agcctatgct gtcgccatcc cactggctgc aggcctcctg    180
ctgctcctgt ttgtgggact gttcatctcc tatgtgatgc tgaagaccaa gagagtgacc    240
aagaaggctc agtga                                                      255
```

```
<210> SEQ ID NO 43
<211> LENGTH: 84
<212> TYPE: PRT
<213> ORGANISM: Homo sapiens

<400> SEQUENCE: 43
```

Met Ala Thr Gly Thr Asp Gln Val Val Gly Leu Gly Leu Val Ala Val
1               5                   10                  15

Ser Leu Ile Ile Phe Thr Tyr Tyr Thr Ala Trp Val Ile Leu Leu Pro
            20                  25                  30

Phe Ile Asp Ser Gln His Val Ile His Lys Tyr Phe Leu Pro Arg Ala
        35                  40                  45

Tyr Ala Val Ala Ile Pro Leu Ala Ala Gly Leu Leu Leu Leu Leu Phe
    50                  55                  60

Val Gly Leu Phe Ile Ser Tyr Val Met Leu Lys Thr Lys Arg Val Thr
65                  70                  75                  80

Lys Lys Ala Gln

```
<210> SEQ ID NO 44
<211> LENGTH: 369
<212> TYPE: DNA
<213> ORGANISM: Homo sapiens

<400> SEQUENCE: 44
atgctctccg tgggcgggct tcggttgagt ttggtccgct tttcctttct gctcctcagg      60
ggagcattgc ttccttctct cgcagtgacc atgacgaaat tagcgcagtg gctttgggga    120
ctagcgatcc tgggctccac ctgggtggcc ctgaccacgg gagccttggg cctggagctg    180
cccttgtcct gccaggaagt cctgtggcca ctgcccgcct acttgctggt gtccgccggc    240
tgctatgccc tgggcactgt gggctatcgt gtggccactt tcatgactg cgaggacgcc    300 gcacgcgagc tgcagagcca gatacaggag gcccgagccg acttagcccg caggggctg    360 cgcttctga                                                             369
```

```
<210> SEQ ID NO 45
<211> LENGTH: 122
<212> TYPE: PRT
<213> ORGANISM: Homo sapiens

<400> SEQUENCE: 45
```

Met Leu Ser Val Gly Gly Leu Arg Leu Ser Leu Val Arg Phe Ser Phe
1               5                   10                  15

Leu Leu Leu Arg Gly Ala Leu Leu Pro Ser Leu Ala Val Thr Met Thr
            20                  25                  30

Lys Leu Ala Gln Trp Leu Trp Gly Leu Ala Ile Leu Gly Ser Thr Trp
        35                  40                  45

Val Ala Leu Thr Thr Gly Ala Leu Gly Leu Glu Leu Pro Leu Ser Cys
    50                  55                  60

Gln Glu Val Leu Trp Pro Leu Pro Ala Tyr Leu Leu Val Ser Ala Gly
65                  70                  75                  80

```
Cys Tyr Ala Leu Gly Thr Val Gly Tyr Arg Val Ala Thr Phe His Asp
                85                  90                  95

Cys Glu Asp Ala Ala Arg Glu Leu Gln Ser Gln Ile Gln Glu Ala Arg
           100                 105                 110

Ala Asp Leu Ala Arg Arg Gly Leu Arg Phe
       115                 120
```

<210> SEQ ID NO 46
<211> LENGTH: 744
<212> TYPE: DNA
<213> ORGANISM: Homo sapiens

<400> SEQUENCE: 46

```
atggcggccg aggcggacgg accgcttaaa cggctgctcg tgccgattct tttacctgag       60
aaatgctacg accaactttt cgttcagtgg gacttgcttc acgtcccctg cctcaagatt      120
ctcctcagca aaggcctggg gctgggcatt gtggctggct cacttctagt aaagctgccc      180
caggtgttta aaatccgggg agccaagagt gctgaagggt tgagtctcca gtctgtaatg      240
ctggagctag tggcattgac tgggaccatg gtctacagca tcactaacaa cttcccattc      300
agctcttggg gtgaagcctt attcctgatg ctccagacga tcaccatctg cttcctggtc      360
atgcactaca gaggacagac tgtgaaaggt gtcgctttcc tcgcttgcta cggcctggtc      420
ctgctggtgc ttctctcacc tctgacgccc ttgactgtag tcaccctgct ccaggcctcc      480
aatgtgcctg ctgtggtggt ggggaggctt ctccaggcag ccaccaacta ccacaacggg      540
tacacaggcc agctctcagc catcacagtc ttcctgctgt ttgggggctc cctggcccga      600
atcttcactt ccattcagga aaccggagat ccccctgatgg ctgggacctt tgtggtctcc      660
tctctctgca acggcctcat cgccgcccag ctgctcttct actggaatgc aaagcctccc      720
cacaagcaga aaaaggcgca gtag                                            744
```

<210> SEQ ID NO 47
<211> LENGTH: 247
<212> TYPE: PRT
<213> ORGANISM: Homo sapiens

<400> SEQUENCE: 47

```
Met Ala Ala Glu Ala Asp Gly Pro Leu Lys Arg Leu Leu Val Pro Ile
  1               5                  10                  15

Leu Leu Pro Glu Lys Cys Tyr Asp Gln Leu Phe Val Gln Trp Asp Leu
            20                  25                  30

Leu His Val Pro Cys Leu Lys Ile Leu Leu Ser Lys Gly Leu Gly Leu
        35                  40                  45

Gly Ile Val Ala Gly Ser Leu Leu Val Lys Leu Pro Gln Val Phe Lys
    50                  55                  60

Ile Arg Gly Ala Lys Ser Ala Glu Gly Leu Ser Leu Gln Ser Val Met
 65                  70                  75                  80

Leu Glu Leu Val Ala Leu Thr Gly Thr Met Val Tyr Ser Ile Thr Asn
                85                  90                  95

Asn Phe Pro Phe Ser Ser Trp Gly Glu Ala Leu Phe Leu Met Leu Gln
           100                 105                 110

Thr Ile Thr Ile Cys Phe Leu Val Met His Tyr Arg Gly Gln Thr Val
       115                 120                 125

Lys Gly Val Ala Phe Leu Ala Cys Tyr Gly Leu Val Leu Leu Val Leu
   130                 135                 140

Leu Ser Pro Leu Thr Pro Leu Thr Val Val Thr Leu Leu Gln Ala Ser
```

```
                145                 150                 155                 160
Asn Val Pro Ala Val Val Gly Arg Leu Leu Gln Ala Ala Thr Asn
                    165                 170                 175
Tyr His Asn Gly Tyr Thr Gly Gln Leu Ser Ala Ile Thr Val Phe Leu
                180                 185                 190
Leu Phe Gly Gly Ser Leu Ala Arg Ile Phe Thr Ser Ile Gln Glu Thr
            195                 200                 205
Gly Asp Pro Leu Met Ala Gly Thr Phe Val Val Ser Ser Leu Cys Asn
        210                 215                 220
Gly Leu Ile Ala Ala Gln Leu Leu Phe Tyr Trp Asn Ala Lys Pro Pro
225                 230                 235                 240
His Lys Gln Lys Lys Ala Gln
                245

<210> SEQ ID NO 48
<211> LENGTH: 25
<212> TYPE: DNA
<213> ORGANISM: Artificial Sequence
<220> FEATURE:
<223> OTHER INFORMATION: Artificially synthesized primer sequence

<400> SEQUENCE: 48
atgacaatgt ggggaagtca acggg                                             25

<210> SEQ ID NO 49
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 49
tgtgtggtta ccgttctttg aatacataga                                        30

<210> SEQ ID NO 50
<211> LENGTH: 29
<212> TYPE: DNA
<213> ORGANISM: Artificial Sequence
<220> FEATURE:
<223> OTHER INFORMATION: Artificially synthesized primer sequence

<400> SEQUENCE: 50
atagaaaatg atttatggta cagctcaaa                                         29

<210> SEQ ID NO 51
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 51
agaccaaatt aattatgcct ttacatgtac                                        30

<210> SEQ ID NO 52
<211> LENGTH: 40
<212> TYPE: DNA
<213> ORGANISM: Artificial Sequence
<220> FEATURE:
<223> OTHER INFORMATION: Artificially synthesized primer sequence
```

```
<400> SEQUENCE: 52
agaattcacc atgagcaaca tgaatatact tgcgtatctt                              40

<210> SEQ ID NO 53
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 53
gaaattccaa tgtattccat attcacttat                                        30

<210> SEQ ID NO 54
<211> LENGTH: 42
<212> TYPE: DNA
<213> ORGANISM: Artificial Sequence
<220> FEATURE:
<223> OTHER INFORMATION: Artificially synthesized primer sequence

<400> SEQUENCE: 54
aagatctaat acattaaaac attttagatt aatgaatatg tg                          42

<210> SEQ ID NO 55
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 55
aggtaccgta cactccactc tatgatgatc attc                                   34
```

METHODS OF SCREENING FOR COMPOUNDS THAT INHIBIT THE BIOSYNTHESIS OF GPI IN MALARIA PARASITES

CROSS-REFERENCES TO RELATED APPLICATIONS

This application is a divisional application of U.S. patent application Ser. No. 10/535,928, filed Dec. 9, 2005, now U.S. Pat. No. 7,928,215, which claims the benefit of PCT/JP03/14920, filed Nov. 21, 2003, which claims the benefit of U.S. Provisional Application No. 60/428,589, filed Nov. 22, 2002. The entire disclosures of all of the above-referenced prior applications are expressly incorporated herein by reference.

TECHNICAL FIELD

The present invention relates to methods of screening for compounds that inhibit the biosynthesis of GPI in malaria parasites.

BACKGROUND ART

Malaria is the most common infectious human disease caused by parasitic protozoans. The disease is caused by infection with malaria parasites and is mediated by the mosquito, *Anopheles gambiae*. Every year there are estimated 500 million cases of malaria infection, including more than two million fatal cases (Gardner, et al., Nature 419:498-511, 2003). At present 40% of the world's population lives in malaria-epidemic areas, where it is said that one in every three infants dies from malaria.

Glycosylphosphatidylinositol (GPI) is known to play a key role in the growth and infectivity of parasites, including malaria parasites. There are many GPI-anchored proteins on the cell surface of these parasites. GPI-anchored proteins include proteins such as MSP-1 that function when the parasites invade red blood cells. GPI-anchored proteins act as parasitic antigens and initiate an immune response in the host. Thus, they have long been the subject of research aimed at vaccine development.

GPI not only functions as an anchor to tether proteins to the cell membrane, but is also an abundant glycolipid component of malaria parasite cell membranes. Recent studies have revealed that GPI is toxic and causes lethal symptoms. GPI induces the expression of inflammatory cytokines such as TNF-$\alpha$, and of adhesion molecules. As a result, infected red blood cells adhere to capillaries, obstructing vessels (sequestration), brain blood vessels in particular. This induces further inflammatory reactions that are believed to lead to encephalopathy. Very recently, Schofield et al. reported that an anti-GPI antibody reduces lethality in an in vivo infection model system using the murine malaria parasite *Plasmodium berghei*, and that in vitro, the antibody inhibits late inflammatory reactions caused by *Plasmodium falciparum* (Schofield L, et al., Nature 418:785-789, 2002). These findings suggest that GPI is a major factor in the lethality of malarial infections.

It has also been reported that the acylation of inositol is essential for binding mannose to GPI (Gerold, P. et al., Biochem. J. 344:731-738, 1999), and that the inhibition of inositol acylation, caused by excess glucosamine, inhibits the maturation of the malaria parasite *P. falciparum* (Naik, R. S. et al., J. Biol. Chem. 278:2036-2042, 2003). Thus, compounds that can selectively inhibit GPI biosynthesis, particularly the acylation of inositol, may be highly useful antimalarial drugs.

DISCLOSURE OF THE INVENTION

An objective of the present invention is to provide antimalarial drugs that inhibit the biosynthesis of GPI. More specifically, the present invention provides the malaria parasite DNA that encodes the GWT1 protein, which is a protein involved in the biosynthesis of GPI (GPI synthase). The present invention also provides a method of using this DNA in methods of screening for antimalarial drugs. The present invention also provides degenerate mutant DNAs of the DNA that encodes the malaria parasite GPI biosynthesis protein. These degenerate mutant DNAs have a lower AT content than the original DNA. The present invention also provides a method of using the degenerate mutant DNAs in methods of screening for antimalarial drugs.

The GWT1 gene was originally found to encode a fungal GPI-anchored protein synthase (WO 02/04626), and is conserved in organisms ranging from yeasts to humans. The present inventors confirmed that GWT1 homologues (PfGWT1 for *P. falciparum* GWT1; PyGWT1 for *P. yoelii yoelii* GWT1) are included in the entire genomic sequences of *Plasmodium falciparum* (*P. falciparum*) and *Plasmodium yoelii yoelii* (*P. yoelii yoelii*) (Gardner, et al., Nature 419:498-511, 2003; Carlton et al., Nature 419:512-519, 2003). The present inventors also found that the GWT1 gene product acts as a GlcN-PI acyltransferase in the GPI biosynthesis pathway. The PfGWT1 gene product is expected to have similar activity, and thus compounds that inhibit this activity can be promising antimalarial drugs.

In WO 02/04626, the present inventors disclosed a group of compounds that inhibit the activity of the fungal GWT1 gene product. Compounds inhibiting the activity of the PfGWT1 gene product were expected to be antimalarial drugs.

In the present invention, the present inventors succeeded in isolating a region thought to be almost the full length of the PfGWT1. Using the GWT1 gene products of malaria parasites such as *P. falciparum*, antimalarial drugs can be screened through binding assays, glucosaminyl (acyl)phosphatidylinositol (PI-GlcN) acyltransferase assays, or using GPI-anchored protein detection systems. Compounds obtained from such screenings can be promising antimalarial drugs. Furthermore, the present inventors revealed that degenerate mutant DNAs (degenerate mutants of the DNA that encodes the malaria parasite GPI biosynthesis protein) having a lower AT content than the original DNA, complement the phenotype of the GWT1 gene-deficient fungus. Thus, it is possible to screen for compounds that inhibit the activity of proteins involved in GPI biosynthesis in malarial parasites by using, as an index, the phenotype of a GPI synthase gene-deficient fungus, into which a degenerate mutant DNA with a lower AT content (than the DNA encoding the GPI biosynthesis protein in malaria parasites) has been introduced.

Specifically, the present invention provides the following [1] to [25]:

[1] a DNA according to any one of (a) to (d), which encodes a protein of a malaria parasite having a GlcN-PI acyltransferase activity:

(a) a DNA encoding a protein comprising the amino acid sequence of SEQ ID NO: 2 or 4, (b) a DNA comprising the nucleotide sequence of SEQ ID NO: 1 or 3, (c) a DNA hybridizing to a DNA comprising the nucleotide sequence of SEQ ID NO: 1 or 3 under stringent conditions, and (d) a DNA encoding a protein which comprises the amino acid sequence of SEQ ID NO: 2 or 4, in which one or more amino acids have been added, deleted, substituted, and/or inserted;

[2] a protein encoded by the DNA according to [1];

[3] a vector into which the DNA according to [1] is inserted;

[4] a transformant which retains, in an expressible state, the DNA according to [1] or the vector according to [3];

[5] an antimalarial drug which comprises as an active ingredient a compound that inhibits the activity of the protein according to [2];

[6] the antimalarial drug according to [5], wherein the compound that inhibits the activity of the protein according to [2] is at least one selected from the group consisting of the following compounds (1) to (5):

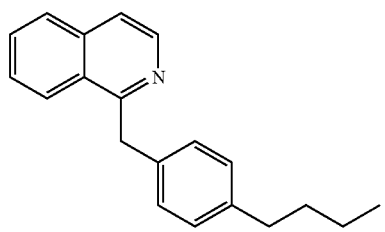

(1)

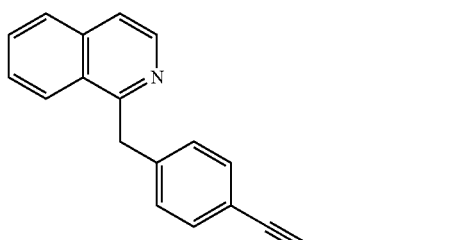

(2)

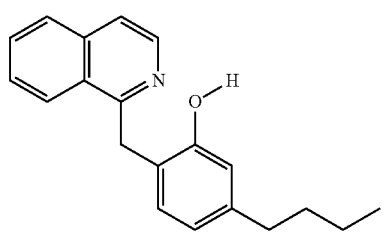

(3)

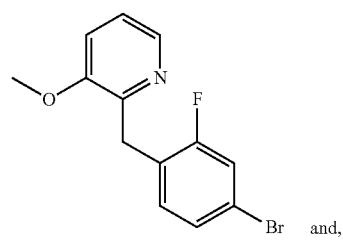

(4) and,

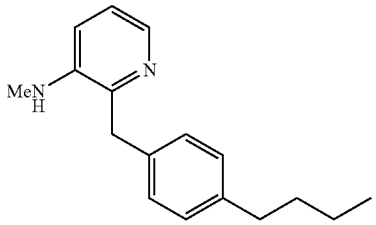

(5)

[7] a method of screening for a compound having antimalarial activity, which comprises the steps of:

(1) contacting the protein according to [2] with a test sample and a labeled compound that has the activity of binding to the protein, (2) detecting the labeled compound that binds to the protein, and, (3) selecting a test sample that decreases the amount of labeled compound that binds to the protein;

[8] the method according to [7], wherein the labeled compound that has the activity of binding to the protein is produced by labeling at least one compound selected from the group consisting of the compounds (1) to (5) according to [6];

[9] a method of screening for a compound having antimalarial activity, which comprises the steps of:

(1) contacting a test sample with the protein according to [2], (2) detecting GlcN-(acyl)PI, and, (3) selecting a test compound that decreases the level of GlcN-(acyl)PI;

[10] a method of screening for a compound having antimalarial activity, which comprises the steps of:

(1) contacting a test sample with a cell overexpressing the protein according to [2], (2) determining the amount of GPI-anchored protein transported to the cell wall, and, (3) selecting a test sample that decreases the amount of the GPI-anchored protein transported to the cell wall, as determined in step (2);

[11] a method for treating malaria, which comprises administering a compound that inhibits the activity of the protein according to [2];

[12] the method according to [11], wherein the compound that inhibits the activity of the protein according to [2] is the compound according to [5];

[13] a DNA encoding a protein that has the activity of complementing the phenotype of a GPI synthase gene-deficient yeast, which is a degenerate mutant of a DNA encoding a protein involved in GPI biosynthesis in malaria parasites, and that has a lower AT content than the original DNA;

[14] a DNA encoding a protein that has the activity of complementing the phenotype of a GPI synthase gene-deficient yeast, which is a degenerate mutant of a DNA encoding a protein involved in GPI biosynthesis in malaria parasites, and that has an AT content which is reduced by 70%;

[15] the DNA according to [13] or [14], which is selected from the group consisting of:

(a) a DNA encoding a protein that comprises any one of the amino acid sequences of SEQ ID NOs: 2 and 4, and odd sequence identification numbers in SEQ ID NOs: 6-47, (b) a DNA comprising any one of the nucleotide sequences of SEQ ID NOs: 1 and 3, and even sequence identification numbers in—SEQ ID NOs: 6-47, (c) a DNA hybridizing under stringent conditions to a DNA that comprises any one of the nucleotide sequences of SEQ ID NOs: 1 and 3, and even sequence identification numbers in SEQ ID NOs: 6-47, and, (d) a DNA encoding a protein which comprises any one of the amino acid sequences of SEQ ID NOs: 2 and 4, and odd sequence identification numbers in SEQ ID NOs: 6-47, in which one or more amino acids have been added, deleted, substituted, and/or inserted;

[16] a DNA comprising the nucleotide sequence of SEQ ID NO: 5;

[17] a vector in which a DNA according to any one of [13] to [16] is inserted;

[18] a transformant which retains, in an expressible state, the DNA according to any one of [13] to [16] or the vector according to [17];

[19] the transformant according to [18], which is a GPI synthase gene-deficient fungus;

[20] the transformant according to [18], which is a GPI synthase gene-deficient yeast;

[21] a method for producing a protein encoded by a DNA according to any one of [13] to [16], which comprises the steps of culturing the transformant according to any one of [18] to [20], and recovering the expressed protein from the transformant or the culture supernatant;

[22] a method of screening for a compound having antimalarial activity, which comprises the steps of:

(1) contacting a test sample with a GPI synthae gene-deficient fungus expressing the DNA according to any one of [13] to [16], (2) assaying the growth of that fungus, and, (3) selecting a test compound that inhibits the growth of that fungus;

[23] a method of screening for a compound having antimalarial activity, which comprises the steps of:

(1) contacting a test sample with a GPI synthase gene-deficient fungus expressing the DNA according to any one of [13] to [16], (2) determining the amount of a GPI-anchored protein transported to the fungal cell walls, and, (3) selecting a test sample that decreases the amount of the GPI-anchored protein transported to the cell wall, as determined in step (2);

[24] a method of screening for a compound having antimalarial activity, which comprises the steps of:

(1) introducing the DNA according to anyone of [13] to [16] into a GPI synthase gene-deficient fungus and expressing the protein encoded by the DNA, (2) preparing the protein expressed in step (1), (3) contacting the prepared protein with a test sample and a labeled compound that has the activity of binding to the protein, (4) detecting the labeled compound that binds to the protein, and, (5) selecting a test sample that decreases the amount of labeled compound that binds to the protein; and,

[25] a method of screening for a compound having antimalarial activity, which comprises the steps of:

(1) introducing into a GWT1-deficient fungus, (i) a DNA encoding a protein that has the activity of complementing the phenotype of a GWT1-deficient yeast, wherein the DNA is a degenerate mutant of a DNA encoding a malaria parasite GWT1 protein that has a lower AT content than the original DNA, or (ii) a vector into which the degenerate mutant of DNA has been inserted, and expressing the protein encoded by the degenerate mutant DNA, (2) preparing the protein expressed in step (1), (3) contacting the prepared protein with a test sample, (4) detecting GlcN-(acyl)PI, and (5) selecting a test compound that decreases the level of GlcN-(acyl)PI.

The DNA encoding the GWT1 protein of *Plasmodium falciparum* (PfGWT1) was isolated for the first time in the present invention. The nucleotide sequence of the DNA encoding the PfGWT1 protein is shown in SEQ ID NO: 1, and the amino acid sequence of the PfGWT1 protein is set forth in SEQ ID NO: 2. In addition, the nucleotide sequence of the DNA encoding the GWT1 protein of *Plasmodium vivax* (PvGWT1) is shown in SEQ ID NO: 3, and the amino acid sequence of the PvGWT1 protein is set forth in SEQ ID NO: 4.

The GWT1 protein is involved in the biosynthesis of glycosylphosphatidylinositol (GPI), which is essential for the growth and infectivity of malaria parasites. Thus, compounds that inhibit the activity of the malaria parasite GWT1 protein can be used as antimalarial drugs. Such antimalarial drugs can be screened using this malaria parasite GWT1 protein.

The present invention provides DNAs encoding the malaria parasite GWT1 protein. Such DNAs include DNA encoding a protein comprising the amino acid sequence of SEQ ID NO: 2 or 4, and DNA comprising the nucleotide sequence of SEQ ID NO: 1 or 3.

The present invention also provides DNAs encoding proteins that are functionally equivalent to the protein comprising the amino acid sequence of SEQ ID NO: 2 or 4. Herein, the expression "functionally equivalent" refers to having biological properties equivalent to those of the protein of interest, comprising the amino acid sequence of SEQ ID NO: 2 or 4 (the PfGWT1 or PvGWT1 proteins). The biological properties of the PfGWT1 and PvGWT1 proteins include GlcN-PI acyltransferase activity. The GlcN-PI acyltransferase activity can be measured by the method reported by Costello and Orlean (J. Biol. Chem. (1992) 267:8599-8603), or Franzot and Doering (Biochem. J. (1999) 340:25-32).

DNAs encoding proteins functionally equivalent to the protein comprising the amino acid sequence of SEQ ID NO: 2 or 4 include: DNAs that hybridize under stringent conditions to the DNA comprising the nucleotide sequence of SEQ ID NO: 1 or 3, and DNA encoding a protein which comprises the amino acid sequence of SEQ ID NO: 2 or 4, in which one or more amino acids have been added, deleted, substituted, and/or inserted.

The DNAs of the present invention can be isolated by methods well known to those skilled in the art. Examples of such methods include the use of hybridization (Southern E. M., J. Mol. Biol. 98: 503-517, 1975) and the polymerase chain reaction (PCR) (Saiki R. K. et al., Science 230: 1350-1354, 1985; Saiki R. K. et al. Science 239:487-491, 1988). More specifically, it would be routine experimentation for those skilled in the art to isolate, from malaria parasites, a DNA highly homologous to DNA comprising the nucleotide sequence of SEQ ID NO: 1 or 3, using the DNA of SEQ ID NO: 1 or 3 or portions thereof as a probe, or by using as a primer a DNA which specifically hybridizes to the DNA comprising the nucleotide sequence of SEQ ID NO: 1 or 3. Furthermore, DNAs that can be isolated by hybridization or PCR techniques, and that hybridize with the DNA comprising the nucleotide sequence of SEQ ID NO: 1 or 3, are also comprised in the DNAs of the present invention. Such DNAs include DNA encoding a malaria parasite homologue of the protein comprising the amino acid sequence of SEQ ID NO: 2 or 4. The malaria parasite homologue includes those of *Plasmodium falciparum, Plasmodium vivax, Plasmodium*

*malariae*, and *Plasmodium ovale*, which comprise the amino acid sequence of SEQ ID NO: 2 or 4.

Preferably, a DNA described above is isolated using hybridization reactions under stringent hybridization conditions. As used herein, the expression "stringent hybridization conditions" refers to, for example, hybridization in 4×SSC at 65° C. followed by washing in 0.1×SSC at 65° C. for one hour. Alternative stringent conditions are hybridization in 4×SSC containing 50% formamide at 42° C. Further alternative stringent conditions are hybridization in PerfectHyb™ (TOYOBO) solution at 65° C. for 2.5 hours, followed by washing: (1) in 2×SSC containing 0.05% SDS at 25° C. for five minutes; (2) in 2×SSC containing 0.05% SDS at 25° C. for 15 minutes; and (3) in 0.1×SSC containing 0.1% SDS at 50° C. for 20 minutes. The DNA thus isolated is expected to encode a polypeptide with a high homology at the amino acid level to the amino acid sequence of SEQ ID NO: 2 or 4. Herein, "high homology" means a sequence identity of at least 70% or more, preferably 80% or more, more preferably 90% or more, and most preferably 95% or more, in the whole amino acid sequence.

The degree of identity at the amino acid sequence level or nucleotide sequence level can be determined using the BLAST algorithm of Karlin and Altschul (Karlin S. and Altschul S. F, Proc. Natl. Acad. Sci. USA. 87: 2264-2268, 1990; Karlin S. and Altschul S. F, Proc. Natl. Acad. Sci. USA. 90: 5873-5877, 1993). BLAST algorithm-based programs, called BLASTN and BLASTX, have been developed (Altschul S. F. et al., J. Mol. Biol. 215: 403, 1990). When a nucleotide sequence is analyzed using BLASTN, the parameters are set, for example, at score=100 and word length=12. On the other hand, when an amino acid sequence is analyzed using BLASTX, the parameters are set, for example, at score=50 and word length=3. When the BLAST and Gapped BLAST programs are used, the default parameters for each program are used. Specific procedures for such analysis are known (please see the web site of the National Institute of Biotechnology Information).

DNAs of the present invention comprise genomic DNAs, cDNAs, and chemically synthesized DNAs. A Genomic DNA or cDNA can be prepared according to conventional methods known to those skilled in the art. For example, a genomic DNA can be prepared as follows: (i) extracting a genomic DNA from malaria parasites; (ii) constructing a genomic library (using, for example, a plasmid, phage, cosmid, BAC, or PAC, as a vector); (iii) spreading the library; and then (iv) conducting colony hybridization or plaque hybridization using probes prepared based on a DNA which encodes the malaria parasite GWT1 protein of the present invention (e.g., SEQ ID NO: 1 or 3). Alternatively, genomic DNA can be prepared by PCR, using primers specific to a DNA which encodes the malaria parasite GWT1 protein of the present invention (e.g., SEQ ID NO: 1 or 3). On the other hand, cDNA can be prepared, for example, as follows: (i) synthesizing cDNA based on mRNA extracted from malaria parasites; (ii) constructing a cDNA library by inserting the synthesized cDNA into vectors such as λZAP; (iii) spreading the cDNA library; and (iv) conducting colony hybridization or plaque hybridization as described above. Alternatively, the cDNA can also be prepared using PCR.

The present invention also provides DNAs encoding proteins structurally similar to the protein comprising the amino acid sequence of SEQ ID NO: 2 or 4. Such DNAs include those which comprise nucleotide sequences encoding proteins comprising amino acid sequences in which one or more amino acid residues are substituted, deleted, inserted, and/or added. There is no limitation on the number and site of the amino acid mutation in proteins mentioned above, so long as the mutated protein retains functions of the original protein such as those described in Mark, D. F. et al., Proc. Natl. Acad. Sci. USA (1984) 81, 5662-5666; Zoller, M. J. & Smith, M., Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413. The percentage of mutated amino acids is typically 10% or less, preferably 5% or less, and more preferably 1% or less of the total amino acid residues. In addition, the number of mutated amino acids is usually 30 amino acids or less, preferably 15 amino acids or less, more preferably five amino acids or less, still more preferably three amino acids or less, even more preferably two amino acids or less.

It is preferable that the mutant amino acid residue be one that retains the properties of the side-chain after its mutation (a process known as conservative amino acid substitution). Examples of amino acid side chain properties are hydrophobicity (A, I, L, M, F, P, W, Y, V) and hydrophilicity (R, D, N, C, E, Q, G, H, K, S, T). Side chains include: aliphatic side-chains (G, A, V, L, I, P); side chains containing an hydroxyl group (S, T, Y); side chains containing a sulfur atom (C, M); side chains containing a carboxylic acid and an amide (D, N, E, Q); basic side-chains (R, K, H); and aromatic side-chains (H, F, Y, W).

A fusion protein comprising the malaria parasite GWT1 protein is an example of a protein to which one or more amino acids residues have been added. Fusion proteins can be made by techniques well known to a person skilled in the art. For example, and without limitation to this particular technique, the DNA encoding the malaria parasite GWT1 protein of the present invention can be combined with DNA encoding another peptide or protein such that their reading frames match. A protein of the present invention can form a fusion protein with a number of known peptides. Such peptides include FLAG (Hopp, T. P. et al., Biotechnology (1988) 6, 1204-1210), 6×His, 10×His, Influenza agglutinin (HA), human c-myc fragment, VSP-GP fragment, p18HIV fragment, T7-tag, HSV-tag, E-tag, SV40T antigen fragment, lck tag, α-tubulin fragment, B-tag, and Protein C fragment. Examples of proteins that may be fused to a protein of the present invention include glutathione-S-transferase (GST), HA, immunoglobulin constant region, β-galactosidase, and maltose-binding protein (MBP).

In addition to using the above-mentioned hybridization and PCR techniques, those skilled in the art could prepare the above-described DNA by methods including, for example, site-directed mutagenesis to introduce mutations in that DNA (Kramer W. and Fritz H-J., Methods Enzymol. 154: 350, 1987). A protein's amino acid sequence may also be mutated in nature due to mutation of the nucleotide sequence which encodes the protein. In addition, degenerate mutant DNAs, in which nucleotide mutations do not result in amino acid mutations in the proteins (degeneracy mutants), are also comprised in the present invention. Furthermore, the present invention also comprises proteins encoded by the above-described DNAs of this invention.

The present invention provides vectors containing the DNAs of the present invention, transformants retaining the DNAs or vectors of the present invention, and methods for producing proteins of the present invention which utilize these transformants.

A vector of the present invention is not limited so long as the DNA inserted into the vector is stably retained. For example, pBluescript® vector (Stratagene) is preferable as a cloning vector when using *E. coli* as a host. An expression vector is particularly useful when using a vector to produce a protein of the present invention. The expression vector is not specifically limited, so long as it expresses proteins in vitro, in *E. coli*, in cultured cells, and in vivo. Preferable examples of expression vectors include the pBEST vector (Promega Corporation) for in vitro expression, the pET vector (Novagen) for expression in *E. coli*, the pME18S-FL3 vector (GenBank Accession No. AB009864) for expression in cultured cells, and the pME18S vector (Mol. Cell. Biol. 8: 466-472, 1988) for in vivo expression. The insertion of a DNA of the present invention into a vector can be carried out by conventional methods, for example, by a ligase reaction using restriction enzyme sites (Current Protocols in Molecular Biology, ed. by Ausubel et al., John Wiley & Sons, Inc. 1987, Section 11.4-11.11).

The host cell into which the vector of the present invention is introduced is not specifically limited, and various host cells can be used according to the objectives of this invention. For example, cells that can be used to express the proteins include, but are not limited to, bacterial cells (e.g., *Streptococcus, Staphylococcus, E. coli, Streptomyces, Bacillus subtilis*), fungal cells (e.g., yeast, *Aspergillus*), insect cells (e.g., *Drosophila* S2, *Spodoptera* SF9), animal cells (e.g., CHO, COS, HeLa, C127, 3T3, BHK, HEK293, Bowes melanoma cell), and plant cells. The transfection of a vector to a host cell can be carried out by conventional methods such as calcium phosphate precipitation, electroporation (Current protocols in Molecular Biology, ed. by Ausubel et al., John Wiley & Sons, Inc. 1987, Section 9.1-9.9), the Lipofectamine method (GIBCO-BRL), and microinjection.

By incorporating an appropriate secretion signal into the protein of interest, the protein expressed in host cells can be secreted into the lumen of the endoplasmic reticulum, into cavities around the cells, or into the extracellular environment. These signals may be endogenous or exogenous to the protein of interest.

When a protein of the present invention is secreted into the culture medium, it is collected from that medium. If a protein of the present invention is produced intracellularly, the cells are lysed and then the protein is collected.

A protein of the present invention can be collected and purified from a recombinant cell culture using methods known in the art, including, but not limited to, ammonium sulfate or ethanol precipitation, acid extraction, anionic or cationic exchange chromatography, phosphocellulose chromatography, hydrophobic interaction chromatography, affinity chromatography, hydroxylapatite chromatography, and lectin chromatography.

Compounds including DNAs of the present invention are isolated compounds. Herein; the term "isolated" refers to being separated from the original environment (for example, the natural environment if it is naturally-occurring). A compound in a sample where the compound of interest is substantially abundant, and/or in a sample where the compound of interest has been partially or substantially purified, is an "isolated" compound. The term "substantially purified", as used herein, refers to a state where the compound has been separated from the original environment, and from which at least 60%, preferably 75%, and most preferably 90% of other coexisting natural components have been removed.

The present invention provides an antimalarial drug that inhibits the activity of the GWT1 gene product of malaria parasites. A preferred compound inhibiting the activity of the GWT1 gene product of malaria parasites is the compound described in WO 02/04626, and includes the compounds (1) to (5):

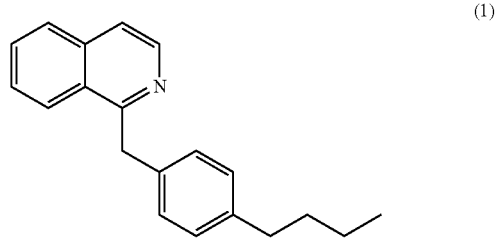

(1)

compound (1): 1-(4-butyl benzyl) isoquinoline

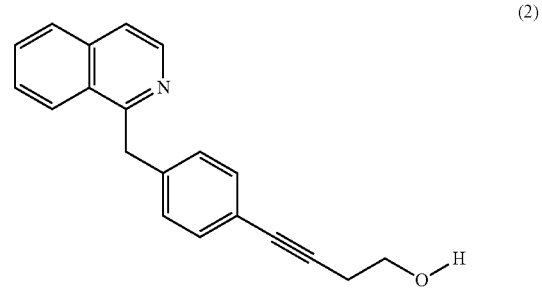

(2)

compound (2): 4-[4-(1-isoquinolyl methyl) phenyl]-3-butyne-1-ol

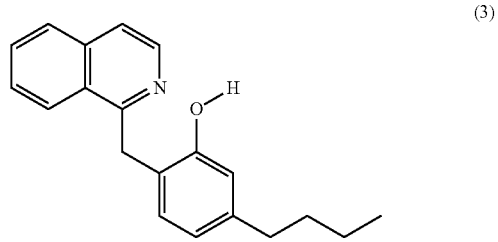

(3)

compound (3): 5-butyl-2-(1-isoquinolyl methyl) phenol

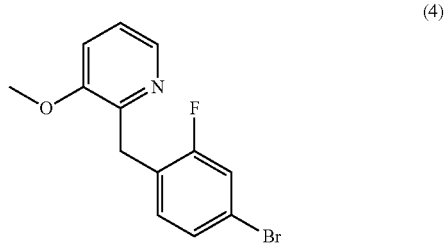

(4)

compound (4): 2-(4-bromo-2-fluorobenzyl)-3-methoxypyridine

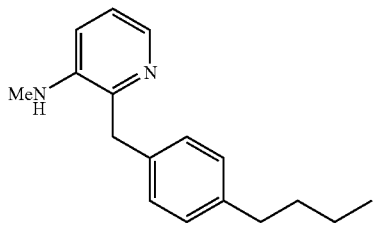

compound (5): N-(2-(4-butyl benzyl)-3-pyridyl)-N-methylamine

A Compound that inhibits the activity of the malaria parasite GWT1 gene product, or a salt thereof, or a hydrate thereof, can be administered as it is to mammals (preferably humans). It can also be formulated by a conventional method into a tablet, powder, fine granule, granule, coated tablet, capsule, syrup, troche, inhalant, suppository, injection, ointment, eye ointment, eye drop, nasal drop, ear drop, cataplasm, lotion, and such, and then administered.

For formulation of a pharmaceutical, auxiliary agents ordinarily used in pharmaceutical formulations (for example, fillers, binders, lubricants, coloring agents, flavoring agents, and as necessary, stabilizers, emulsifiers, absorbefacient, surfactants, pH regulators, antiseptics, and antioxidants) can be used. A pharmaceutical formulation can be prepared using an ordinary method combining components that are generally used as ingredients for pharmaceutical preparations.

For example, oral formulations can be produced by combining a compound of the present invention or a pharmaceutically acceptable salt thereof with a filler, and as necessary, a binder, disintegrator, lubricant, coloring agent, flavoring agent, and such, and then formulating the mixture into a powder, fine granule, granule, tablet, coated tablet, capsule, and such by usual methods.

Examples of these components include: animal fat and vegetable oils such as soybean oil, beef tallow, and synthetic glyceride; hydrocarbons such as liquid paraffin, squalene, and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hardened castor oil, and polyoxyethylene polyoxypropylene block copolymer; water-soluble macromolecules such as hydroxyethyl cellulose, polyacrylic acid, carboxyvinyl polymer, polyethylene glycol, polyvinyl pyrrolidone, and methyl cellulose; lower alcohols such as ethanol and isopropanol; polyhydric alcohols such as glycerol, propylene glycol, dipropylene glycol, and sorbitol; sugars such as glucose and sucrose; inorganic powder such as silicic acid anhydride, magnesium aluminum silicate, and aluminum silicate; and purified water. Examples of fillers include lactose, corn starch, refined white sugar, glucose, mannitol, sorbitol, crystalline cellulose, and silicon dioxide. Binders are polyvinyl alcohol, polyvinyl ether, methyl cellulose, ethyl cellulose, gum arabic, tragacanth, gelatin, shellac, hydroxypropylmethyl cellulose, hydroxypropyl cellulose, polyvinyl pyrrolidone, polypropyleneglycol polyoxyethylene block polymer, meglumine, and such. Examples of disintegrators include starch, agar, powdered gelatin, crystalline cellulose, calcium carbonate, sodium hydrogencarbonate, calcium citrate, dextrin, pectin, and calcium carboxymethylcellulose. Lubricants are magnesium stearate, talc, polyethyleneglycol, silica, hardened vegetable oil, and such. Examples of coloring agents are those accepted for addition to pharmaceuticals. Flavoring agents are cocoa powder, l-menthol, aromatic dispersant, mint oil, borneol, cinnamon powder, and such. The use of sugar coating and other appropriate coating as necessary is of course permissible for these tablets and granules.

Furthermore, liquid formulations such as syrups and injections can be prepared using conventional methods. In such methods, pH regulators, solubilizers, isotonizing agents, and such, and as necessary solubilizing adjuvants, stabilizers, and so on, are added to the compounds of this invention or pharmaceutically acceptable salts thereof.

Methods for producing external formulations is not restricted and can be a conventional method. That is, base materials used for formulation can be selected from various materials ordinarily used for medicaments, quasi-drugs, cosmetics, and such. Specifically, the base materials to be used are, for example, animal fat and vegetable oils, mineral oils, ester oils, waxes, higher alcohols, fatty acids, silicone oils, surfactants, phospholipids, alcohols, polyhydric alcohols, water soluble macromolecules, clay minerals, and purified water. As necessary, pH regulators, antioxidants, chelating agents, antiseptic and antifungal agents, coloring matters, fragrances, and such may also be added. However the base materials of the external formulations of the present invention are not limited thereto. Furthermore, as necessary, components such as those that have a differentiation-inducing effect, blood flow accelerants, fungicides, antiphlogistic agents, cell activators, vitamins, amino acids, humectants, and keratolytic agents can be combined. The above-mentioned base materials are added in an amount that leads to the concentration usually used for external formulations.

The term "salt" as described in the present invention preferably includes, for example, a salt with an inorganic or organic acid, a salt with an inorganic or inorganic base, or a salt with an acidic or basic amino acid. In particular, a pharmaceutically acceptable salt is preferable. Acids and bases form salts at an appropriate ratio of 0.1 to 5 molecules of acid or base to one molecule of the compound.

Preferable examples of a salt with an inorganic acid are a salt with hydrochloric acid, hydrobromic acid, sulfuric acid, nitric acid, and phosphoric acid. Preferably, a salt with an organic acid includes a salt with acetic acid, succinic acid, fumaric acid, maleic acid, tartaric acid, citric acid, lactic acid, stearic acid, benzoic acid, methanesulfonic acid, and p-toluenesulfonic acid.

Preferable examples of a salt with an inorganic base are: an alkali metal salt such as a sodium salt and a potassium salt; an alkaline earth metal salt such as a calcium salt and a magnesium salt; an aluminum salt, and an ammonium salt. Preferably, a salt with an organic base includes a salt with diethylamine, diethanolamine, meglumine, and N,N'-dibenzylethylenediamine.

Preferable examples of a salt with an acidic amino acid are a salt with aspartic acid and glutamic acid, and preferably, a salt with a basic amino acid includes a salt with arginine, lysine, and ornithine.

The compounds of the present invention or salts thereof, or hydrates thereof can be administered orally or parenterally by a conventional method without limitation as to their form. They can be formulated into dosage forms such as tablets, powders, fine granules, capsules, syrups, troches, inhalants, suppositories, injections, ointments, eye ointments, eye drops, nasal drops, ear drops, cataplasms, and lotions. The dose of the pharmaceutical compositions of this invention can be selected appropriately depending on the degree of the symptoms, the patient's age, sex and weight, the dosage form, the type of salt, the specific type of disease, and such.

Compounds of the present invention are administered to a patient in a therapeutically effective dose. Herein, "therapeutically effective dose" refers to the amount of pharmaceutical agent that yields the desired pharmacological result and is effective in the recovery or relief from the symptoms of the patient to be treated. The dose differs markedly depending on the type of disease, the degree of symptoms, the patient's weight, age, sex, sensitivity to the agent. However, the normal adult dosage for one day is about 0.03 mg to 1000 mg, preferably 0.1 mg to 500 mg, more preferably 0.1 mg to 100 mg, when administered from once to several times a day, or from once to several times over several days. The dose for injections is normally, about 1 to 3000 µg/kg, and is preferably about 3 to 1000 µg/kg.

In addition, the present invention relates to a method of screening for antimalarial drugs using the malaria parasite GWT1 gene product. Such a screening method includes, but is not limited to: [1] A binding assay which screens for compounds that compete with a labeled compound to bind with the malaria parasite GWT1 gene product; [2] A GlcN-PI acyltransferase assay system to screen for compounds that inhibit the GlcN-PI acyltransferase activity of the malaria parasite GWT1 gene product; and [3] A GPI-anchored protein detection system in which the malaria parasite GWT1 gene product is expressed in cells, preferably fungal cells, and then the GPI-anchored proteins on the cell surface are detected. The present invention is not limited to these methods, and comprises any method of screening for antimalarial drugs using the malaria parasite GWT1 gene product. The methods [1] to [3] listed above are described below in detail.

[1] A Binding Assay to Screen for Compounds that Compete with a Labeled Compound to Bind with the Malaria Parasite GWT1 Gene Product The two methods according to the present invention are disclosed below, namely (1) a method for preparing the malaria parasite GWT1 gene product (hereinafter referred to as the malaria parasite GWT1 protein) and (2) a method for a binding experiment involving a labeled compound (hereinafter referred to as a binding assay).

(1) Method for Preparing the Malaria Parasite GWT1 Protein

The malaria parasite GWT1 protein is prepared from a cell membrane fraction, preferably from fungal cells, more preferably from cells of *S. cerevisiae* into which the DNA encoding the malaria parasite GWT1 protein of SEQ ID NO: 2 has been introduced. It is preferable to introduce such a DNA into GWT1 gene-deficient cells. In the binding assay, the prepared membrane fraction may be used without any further treatment, or can be further purified before use. The procedure using *S. cerevisiae* is described below in detail.

(a) Introduction of the Malaria Parasite GWT1 Gene

The malaria parasite GWT1 gene used in the present invention can be a naturally-occurring gene, or preferably, it can be synthesized based on the amino acid sequence of SEQ ID NO: 2 or 4. The malaria parasite GWT1 gene is very rich in adenine and thymine. Thus, it was predictable that the gene will be difficult to manipulate with ordinary gene recombination techniques, and that gene expression in yeast, cells, and such will be inefficient. Therefore, it is preferable to design a nucleotide sequence in which codons corresponding to each of the corresponding amino acids have been replaced with those that are thought to express efficiently in yeast, cells, and such, and conduct DNA synthesis based on this designed sequence to create an artificial malaria parasite GWT1 gene, which is then used in the experiments described below.

An expression plasmid for the malaria parasite GWT1 is prepared by inserting the malaria parasite GWT1 gene into an *S. cerevisiae* expression vector, for example, an expression vector prepared by inserting a suitable promoter and terminator, such as the pKT10-derived GAPDH promotor and GAPDH terminator, into YEp352's multi-cloning site (Tanaka et al., Mol. Cell. Biol., 10:4303-4313, 1990). *S. cerevisiae* (e.g., G2-10 strain) is cultured in an appropriate medium (e.g., YPD medium (Yeast extract-Polypeptone-Dextrose medium)) while shaking at an appropriate temperature (e.g., 30° C.), and the cells are harvested during the late logarithmic growth phase. After washing, the GWT1-expression plasmid is introduced into *S. cerevisiae* cells using, for example, the lithium-acetate method. This method is described in the User Manual of YEAST MAKER™ Yeast Transformation System (BD Biosciences Clontech). A malaria parasite GWT1-overexpressing strain and a strain carrying a negative control vector can be obtained by culturing the transformed cells on SD (ura-) medium at 30° C. for, two days.

Expression vectors and gene transfer methods for fungal species other than *S. cerevisiae* have been reported as follows: expression vectors such as pcL for *Schizosaccharomyces pombe* (*S. pombe*) and their transfer methods are described by Igarashi et al. (Nature 353:80-83, 1991); expression vectors such as pRM10 for *C. albicans* and their transfer methods are described by Pla J. et al. (Yeast, 12: 1677-1702, 1996); expression vectors such as pAN7-1 for *A. fumigatus* and their transfer methods are described by Punt P. J. et al. (GENE, 56: 117-124, 1987); and expression vectors such as pPM8 for *C. neoformans* and their transfer methods are described by Monden P. et al. (FEMS Microbiol. Lett., 187: 41-45, 2000).

(b) Method for Preparing Membrane Fractions

*S. cerevisiae* cells in which the malaria parasite GWT1 gene has been introduced are cultured in an appropriate medium (e.g., SD (ura-) liquid medium) while being shaken at an appropriate temperature (e.g., 30° C.). The fungal cells are harvested during the mid-logarithmic growth phase, washed, and then suspended in an appropriate amount (e.g., three times the volume of fungal cells) of homogenization buffer (e.g., 50 mM Tris-HCl, pH 7.5, 10 mM EDTA, Complete™ (Roche)). An appropriate amount of glass beads (e.g., four times the volume of fungal cells) is added to the suspension. The mixture is vortexed and then allowed to stand on ice. This operation is repeated several times to crush fungal cells.

One milliliter of the homogenization buffer is added to the resulting lysate. The mixture is centrifuged, for example at 2,500 rpm for five minutes, to precipitate the glass beads and uncrushed fungal cells. The supernatant is transferred to another tube. The tube is centrifuged, for example at 13,500 rpm for ten minutes, to precipitate a membrane fraction (total membrane fraction) comprising organelles. The precipitate is suspended in 1 ml of binding buffer (e.g., 0.1 M Phosphate buffer, pH 7.0, 0.05% Tween 20, Complete™(Roche)), and then centrifuged, for example, at 2,500 rpm for one minute to remove unsuspended material. The supernatant is then centrifuged, for example at 15,000 rpm for five minutes. The precipitate is resuspended in 150 to 650 µl of binding buffer to prepare a membrane fraction.

Membrane fractions can be prepared from fungal species other than *S. cerevisiae* using the method of Yoko-o et al. for *S. pombe* (Eur. J. Biochem. 257:630-637, 1998); the method of Sentandreu M et al. for *C. albicans* (J. Bacteriol., 180: 282-289, 1998); the method of Mouyna I et al. for *A. fumigatus* (J. Biol. Chem., 275: 14882-14889, 2000); and the method of Thompson J R et al. for *C. neoformans* (J. Bacteriol., 181: 444-453, 1999).

Alternatively, the malaria parasite GWT1 protein can be prepared by expressing an *E. coli*, insect and mammalian cell or the like in non-fungal cells.

When mammalian cells are used, the malaria parasite GWT1 gene is ligated with an over-expression vector containing, for example, the CMV promotor, and then introduced into the mammalian cells. Membrane fractions can then be prepared according to the method of Petaja-Repo et al. (J. Biol. Chem., 276:4416-23, 2001).

Insect cells expressing the malaria parasite GWT1 gene (e.g., Sf9 cells) can be prepared using, for example, a baculovirus expression kit such as the BAC-TO-BAC® Baculovirus Expression system (Invitrogen). Membrane fractions can then be prepared according to the method of Okamoto et al. (J. Biol. Chem., 276:742-751, 2001).

The malaria parasite GWT1 protein can be prepared from *E. coli* by, for example, ligating the malaria parasite GWT1 gene into an *E. coli* expression vector such as the pGEX vector (Amersham Biosciences Corp.), and introducing the construct into *E. coli* such as BL21.

(2) Binding Assay Methods
(a) Synthesis of Labeled Compound

The labeled compound is prepared from a compound that has been confirmed to bind to GWT1 proteins. Any compound which can bind to GWT1 proteins can be used. The labeled compound is preferably prepared from the compound described in WO 02/04626, more preferably from compounds according to (1) to (5) described above.

Any labeling method can be used. Preferably, the compound is labeled with a radioisotope, more preferably with $^3H$. The radiolabeled compound can be prepared by typical production methods, using a radioactive compound as a starting material. Alternatively, $^3H$ labeling can be achieved using an $^3H$ exchange reaction.

(b) Confirmation of Specific Binding

The labeled compound is added to the prepared membrane fraction and the mixture is allowed to stand on ice for an appropriate time, for example, one to two hours, while the binding reaction between the labeled compound and the membrane fraction takes place. The membrane fraction is precipitated by centrifuging the mixture, for example at 15,000 rpm for three minutes. The precipitate is resuspended in binding buffer, and the suspension is centrifuged. This is repeated appropriately (twice) to remove any unbound labeled compound. The precipitate is again suspended in binding buffer. The resulting suspension is transferred into a scintillation vial, and a scintillator is added. Radioactivity is measured using a liquid scintillation counter.

The specific binding of the labeled compound to the GWT1 protein can be confirmed by assessing whether binding of the labeled compound is inhibited by adding a large excess of unlabeled compound (ten times or more), and whether the compound binds negligibly to membrane fractions prepared from fungal cells which do not express the GWT1 protein.

(c) Binding Inhibition of a Labeled Compound by a Test Sample

A test sample and the labeled compound are added to the prepared membrane fraction, and the mixture is allowed to stand on ice for an appropriate period of time, for example, one to two hours, while the binding reaction to the membrane fraction takes place. Test compounds used in the present invention's screening method include: a simple naturally-occurring compound, an organic compound, an inorganic compound, a protein, or a peptide, as well as a compound library, an expression product of a genetic library, a cell extract, a cell culture supernatant, a product from fermentative bacteria, an extract of a marine organism, a plant extract, and the like.

The mixture is centrifuged, for example at 15,000 rpm for three minutes to precipitate the membrane fraction. The precipitate is resuspended in binding buffer and the suspension is centrifuged. This is repeated appropriately (twice) to remove any unbound labeled compound. The precipitate is suspended in the binding buffer. The suspension is transferred into a scintillation vial, and scintillator is added thereto. The radioactivity is measured using a liquid scintillation counter.

When the binding of the labeled compound to the membrane fraction is inhibited in the presence of a test sample, the test sample is judged to have the activity of binding to the malaria parasite GWT1 protein.

[2] The GlcN-PI Acyltransferase Assay System for Screening Compounds that Inhibit the GlcN-PI Acyltransferase Activity of the Malaria Parasite GWT1 Protein The transfer of an acyl group to GPI can be detected by the method reported by Costello L. C. and Orlean P., J. Biol. Chem. (1992) 267:8599-8603; or Franzot S. P and Doering T. L., Biochem. J. (1999) 340:25-32. A specific example of the method is described below. The following experimental conditions are preferably optimized for each malaria parasite GWT1 protein to be used.

The malaria parasite GWT1 protein is prepared according to the procedure described in Section 1. A membrane fraction comprising the malaria parasite GWT1 protein is added to a buffer which comprises an appropriate metal ion ($Mg^{2+}$, $Mn^{2+}$) ATP, Coenzyme A, and preferably an inhibitor that prevents the consumption of UDP-GlcNAc in other reactions, for example, nikkomycin Z as an inhibitor of chitin synthesis, or tunicamycin as an inhibitor of asparagine-linked glycosylation. A test sample is then added to the mixture and the resulting mixture is incubated at an appropriate temperature for an appropriate period of time (for example, at 24° C. for 15 min).

A GlcN-(acyl)PI precursor (for example UDP-GlcNAc, Acyl-Coenzyme A, and preferably UDP-[$^{14}C$]GlcNAc) which has been appropriately labeled, and preferably radiolabeled, is added to the mixture. The resulting mixture is incubated for an appropriate period of time (for example, at 24° C. for one hour). A mixture of chloroform and methanol (1:2) is added, the resulting mixture is stirred to halt the reaction, and the lipids are extracted. The extracted reaction product is dissolved in an appropriate solvent, preferably butanol. Then, GlcN-(acyl)PI produced in the reaction is separated by a method such as HPLC or thin layer chromatography (TLC), preferably TLC. When TLC is used, the developer can be selected appropriately from, for example, $CHCl_3/CH_3OH/H_2O$ (65:25:4), $CHCl_3/CH_3OH/1M\ NH_4OH$ (10:10:3), and $CHCl_3$/pyridine/HCOOH (35:30:7). A preferred developer is $CHCl_3/CH_3OH/H_2O$ (65:25:4). The separated GlcN-(acyl)PI is quantified using a method appropriate for the label used. When labeled with an radioisotope, the separated GlcN-(acyl)PI can be quantified based on its radioactivity.

When the amount of GlcN-(acyl)PI produced is reduced in the presence of a test sample, the test sample is judged to have the activity of inhibiting acyl group transfer by the malaria parasite GWT1 protein.

(3) A GPI-Anchored Protein Detection System which Comprises Expressing the Malaria Parasite GWT1 Protein in Cells and Detecting the GPI-Anchored Protein on the Cell Surface The ability of a test sample to inhibit the activity of the malaria parasite GWT1 protein can be determined using a GPI-anchored protein detection system that comprises expressing the GWT1 protein in cells, preferably fungal cells, and then detecting the GPI-anchored protein on the cell surface. The fungi of the present invention are those belonging to Zygomycota, Ascomycota, Basidiomycota, and Deuteromycete, and preferably pathogenic fungi, *Mucor, Saccharomyces, Candida, Cryptococcus, Trichosporon, Malassezia, Aspergillus, Trichophyton, Microsporum, Sporothrix, Blastmyces, Coccidioides, Paracoccidioides, Penicillinium*, and *Fusarium*, more preferably *C. albicans, C. glabrata, C. neoformans*, and *A. fumigatus*, and even more preferably, yeast. Such yeasts include *S. cerevisiae* and *S. pombe*. The method for introducing into the above-described fungal cells an expression vector containing inserted DNA encoding the malaria parasite GWT1 protein is known to those skilled in the art.

When the malaria parasite GWT1 protein is expressed in fungal cells, the amount of GPI-anchored protein transported to the fungal cell wall can be determined by the following methods: (1) by using a reporter enzyme; (2) by using an antibody that reacts with the surface glycoprotein of fungal cell walls; (3) by using the protein's ability to adhere to animal cells; or (4) by observing fungal cells under a light microscope or electron microscope.

The methods of (1) to (4) have been disclosed in WO 02/04626, which is described specifically in Examples of this invention. The methods (1) to (4), and preferably a combination of these methods (1) to (4), can determine whether a test sample inhibits the transport of the GPI-anchored protein onto the cell wall, or the expression of the GPI-anchored protein on the fungal cell surface.

Hereinafter, the methods of (1) to (4) will be described.
(1) A Method Using a Reporter Enzyme The process that transports GPI-anchored proteins to the cell wall can be quantified using a tracer experiment such as one where a GPI-anchored protein is labeled with a radioactive isotope, the fungal cell wall fraction is obtained, and immunoprecipitated using an antibody against the GPI-anchored protein. Alternatively, quantification can be more readily performed as follows: the C-terminal sequence, which is considered to function as a transport signal and is commonly observed among GPI-anchored proteins, can be expressed as a fusion protein with an easily measurable enzyme (reporter enzyme), the fungal cell wall fraction can be obtained, and a reporter system that measures the enzyme activity of each fraction can be used (Van Berkel M A A et al., FEBS Letters, 349: 135-138, 1994). Hereinafter, a method which uses a reporter enzyme will be described, but in the present invention such methods are not to be construed as being limited thereto.

First, the reporter gene is constructed and introduced into fungi. The reporter gene is constructed by linking a promoter sequence that functions in fungi with DNAs that respectively encode a signal sequence, a reporter enzyme, and a GPI-anchored protein C-terminal sequence in such a way that the reading frames match. Examples of the promoter sequence are GAL10 and ENO1. Examples of the signal sequence include α-factor, invertase, and lysozyme. Examples of reporter enzymes are β-lactamase, lysozyme, alkaline phosphatase, and β-galactosidase. Green Fluorescence Protein (GFP), which has no enzyme activity but can be easily detected, can also be used. GPI-anchored protein C-terminal sequences include the α-agglutinin C-terminal sequence, the CWP2 C-terminal sequence, and so on. Furthermore, it is preferable to insert an appropriate selection marker, such as LEU2 and URA3, into the vector comprising the constructed reporter gene.

The constructed reporter gene is inserted into fungi using an appropriate method, such as the lithium acetate method (Gietz D et al., Nucl. Acids Res. 20: 1425, 1992). The fungi are then cultured, as necessary, using a method that suits the selection marker (e.g. using Leu⁻ medium for LEU2 and Ura⁻ medium for URA3), and then fungi into which the DNA has been introduced are selected.

The effect of a test sample on the transport of GPI-anchored proteins to the cell wall is examined by the following method:

The reporter gene-introduced fungi are cultured under appropriate conditions, for example at 30° C. for 48 hours, in the presence of a test sample. After culturing, the culture supernatant is centrifuged, and the reporter enzyme activity of the culture supernatant fraction is measured. The resulting cell fraction is washed, the cell wall components are separated using an appropriate method, such as degrading the cell wall glucan with glucanase, and then the reporter enzyme activity of the cell wall fraction and cytoplasmic fraction is measured. The assay can be simply carried out by using centrifugation to determine the amount of reporter enzyme in the cell fraction, then without washing the cells, using proportional calculations to determine the amount of reporter enzyme derived from the culture supernatant fraction that remains in the cell fraction, and subtracting this from the amount of reporter enzyme of the cell fraction.

If the test sample exhibits the activity of increasing reporter enzyme activity within the culture supernatant fraction (activity per cell), or the activity of decreasing the reporter enzyme activity in the cell wall fraction (activity per cell), the test sample is judged to have influenced the transport process of GPI-anchored proteins to the cell wall.
(2) A Method Using an Antibody that Reacts with the Surface Glycoprotein of Fungal Cell Walls A test sample's ability to influence the expression of a GPI-anchored protein at the fungal surface layer can be determined by quantification using an antibody that reacts with that GPI-anchored protein in the fungal cell wall.

Antibodies can be obtained by predicting the antigenic determinant using the amino acid sequence of, for example, a GPI-anchored protein such as α-agglutinin, Cwp2p, or Als1p (Chen M H et al., J. Biol. Chem., 270:26168-26177, 1995; Van Der Vaat J M et al., J. Bacteriol., 177:3104-3110, 1995; Hoyer L L et al., Mol. Microbiol., 15:39-54, 1995), and then synthesizing the peptide of that region, binding it to an antigenic substance such as a carrier protein, and then immunizing a rabbit or such to obtain polyclonal antibodies, or a mouse or such to obtain a monoclonal antibody. A rabbit polyclonal antibody against the Als1p peptide is preferable.

In an alternative method, a monoclonal antibody against a GPI-anchored protein may be obtained by immunizing mice and such with fungi, preferably fungi which overexpress a GPI-anchored protein such as α-agglutinin, Cwp2p, and Als1p, (in some cases by immunizing further with a partially purified GPI-anchored protein), and then using ELISA, Western blot analysis, and so on to select resultant clones based on the antibody that they produce.

The following method can be used to determine the influence of a test sample on the process that transports a GPI-anchored protein to the cell wall, and on the amount of protein derived from that GPI-anchored protein in the cell wall.

Fungi are cultured in the presence of a test sample under appropriate conditions such as 30° C. for 48 hours. The cultured fungi are collected by centrifugation and the cells are disrupted, preferably using glass beads. The washed, disrupted cells are preferably subjected to centrifugal extraction with SDS, and then the precipitate is washed. After extraction, the disrupted cells are treated with an enzyme that degrades glucan, preferably glucanase, and the centrifuged supernatant thereof is the GPI-anchored protein sample.

The anti-Als1p peptide antibody is coated onto a 96-well plate by overnight incubation at 4° C. The plate is washed with a washing solution, preferably PBS comprising 0.05% Tween 20 (PBST), and blocking is carried out using a reagent that blocks the non-specific adsorption sites of the 96-well plate, preferably a protein such as BSA or gelatin, more preferably BlockAce (Dainippon Pharmaceutical Co., Ltd.). The plate is again washed with a washing solution, preferably PBST, and an appropriately diluted GPI-anchored protein sample is added. The reaction is then carried out for an appropriate time such as two hours at room temperature. After washing with a washing solution, preferably with PBST, an antibody against the enzyme-labeled *C. albicans*, preferably HRP-labeled anti-*Candida* antibody, is reacted for an appropriate time such as two hours at room temperature. The labeling method may be enzyme labeling or radioactive isotope labeling. After washing with a washing solution, preferably PBST, the amount of Als1p in the GPI-anchored protein sample is calculated by a method appropriate to the type of label, i.e. for an enzyme label, by adding a substrate solution and then, upon stopping the reaction, measuring absorbance at 490 nm.

(3) A Method Using the Ability to Adhere to Animal Cells

The test sample's influence on the expression of a GPI-anchored protein on the fungal surface can be determined by measuring the activity of that GPI-anchored protein in the fungal cell wall, and preferably by measuring the ability of fungi to adhere to animal cells and the like. In addition to the activity of Als1p, Hwp1p and such in adhesion to animal cells, GPI-anchored protein activity includes that of α-agglutinin in mating, of Flo1p in yeast aggregation, and so on. Hereinafter, a method using the ability of fungi to adhere to animal cells will be described in detail, but the present invention is not to be construed as being limited thereto.

A fungus with the ability to adhere to cells is used, and this fungus is preferably *C. albicans*. For mammalian cells, cells that adhere to the fungus, preferably intestinal epithelial cells, are used. The mammalian cells are cultured and fixed using an appropriate method, such as ethanol fixation. The test sample and the fungi are incubated for an appropriate time such as 48 hours at 30° C., then inoculated and cultured for a set time, for example, one hour at 30° C. The culture supernatant is then removed, and the cells are washed with a buffer and overlaid with agar media such as Sabouraud Dextrose Agar Medium (Becton Dickinson Company, Ltd.). After culturing at 30° C. overnight, the number of colonies is counted, and the adhesion rate is calculated.

If, when compared to fungi not treated with the compound, a test sample is observed to have the activity of decreasing the number of colonies formed by cell adhesion, that test sample is judged to have influenced the process that transports GPI-anchored proteins to the cell wall.

(4) A Method for Observing Fungi Using an Electron Microscope or an Optical Microscope The influence of a test sample on the expression of the GPI-anchored protein in the fungal surface can be determined by observing the structure of the fungal cell wall using an electron microscope.

In the presence of a test sample, a fungus such as *C. albicans* is cultured for a certain period of time, for example, 48 hours at 30° C., and its ultrafine morphological structure is observed using a transmission electron microscope. Herein, observation using a transmission electron microscope can be carried out, for example by the method according to the Electron Microscope Chart Manual (Medical Publishing Center). The flocculent fibrous structure of the outermost layer of a fungal cell has a high electron density and is observable by transmission electron microscope. This structure is not influenced by other existing antifungal agents and is considered to be a surface glycoprotein layer, including GPI-anchored proteins as its constituents. When this structure disappears, leaving only a slight layer with a high electron density, the test sample is judged to have influenced the process that transports GPI-anchored proteins to the cell wall, compared to untreated cells.

When observation under both a transmission electron microscope and an optical microscope reveals greatly swollen fungal cells and inhibited budding (division), the test sample is judged to have an influence on the cell wall.

The present invention also provides a method for treating malaria, which comprises the step of administering a compound that inhibits the activity of a GWT1 protein a malaria parasite. Such a compound includes the compounds described in WO 02/04626 (for example, the compounds described herein in (1)-(5)).

The nucleotide sequence for the natural PfGWT1 protein is characterized by an exceedingly high AT content (80.41%), and thus codon usage is biased. In addition, the gene contains sequence stretches comprising six or more consecutive A residues at 23 separate positions, and these sequence stretches may serve as pseudo-poly (A) sites, thus producing truncated proteins. Because of the features described above, the gene was only expressed poorly in yeast, and very difficult to amplify using PCR or to replicate in *E. coli*. It was also difficult to determine the nucleotide sequence. However, the present inventors succeeded in expressing the PfGWT1 protein with a high efficiency by using a degenerate mutant of the DNA (SEQ ID NO: 5), with a lower AT content than the DNA encoding the PfGWT1 protein. The inventors also revealed that the introduction of the degenerate mutant DNA can rescue the phenotype of GWT1-deficient yeast. This finding suggests that the GPI synthase of a malaria parasite is interchangeable with that of a fungus such as yeast.

The AT content of the gene encoding the malaria parasite GPI synthase is, for example, 79.35% for GPI8 and 77.89% for the GPI13 of *P. falciparum*. These AT contents are as high as that of PfGWT1. It is predicted that most *P. falciparum* genes are hardly expressed in other species, because the average AT content over the translated regions of the *P. falciparum* genome is 76.3%. The present inventors succeeded in expressing a degenerate mutant of the DNA with a lower AT content than that of the DNA encoding the PfGWT1 protein, in yeast. Hence, the malaria parasite GPI synthase can be expressed in a host other than malaria parasites by using such a degenerate DNA mutant. Furthermore, GPI-deficient yeast and GWT1-deficient yeast are known to exhibit similar phenotypes, including the characteristic of lethality and such. Thus, the phenotype of the GPI synthase gene-deficient fungus can be rescued by using the degenerate mutant DNA described above.

The phenotype of the GPI synthase gene-deficient fungus into which the degenerate mutant DNA described above has been introduced depends on the activity of the malaria parasite GPI synthase. Accordingly, compounds that inhibit the activity of the malaria parasite GPI synthase can be selected by screening using the phenotype of the GPI synthase gene-deficient fungus as an index. Thus, antimalarial drugs targeting the GPI biosynthesis pathway can be selected without actually using the malaria parasites themselves.

The present invention provides a degenerate mutant DNA encoding a protein that has the activity of rescuing the phenotype of a GPI synthase gene-deficient fungus, and which has an AT content lower than that of the original DNA encoding the protein involved in the biosynthesis of GPI. Such a DNA can be used in the screening method of the present invention.

As used herein, the term "AT content" refers to the content of adenine and thymine in the entire nucleotide sequence of the coding region of the GPI synthase gene. The AT content in the degenerate mutant DNA of the present invention preferably ranges from 50% to 70%, more preferably from 53% to 65%, and still more preferably from 55% to 62%.

The phenotype of the GPI synthase gene-deficient fungus includes temperature sensitivity (preferably, sensitivity to high temperatures) and lethality.

The proteins of the present invention involved in the biosynthesis of GPI in malaria parasites include GWT1, GPI1, GPI8, GPI3/PIG-A, GPI10/PIG-B, YJR013W/PIG-M, GPI13/PIG-O, GAA1/GAA-1, DPM1, GPI2, GPI15, YDR437W, GPI12, MCD4, GPI11, GPI7, GPI17, GPI16, CDC91, DPM2, DPM3, and SL15. Of the proteins indicated above, GPI1 and GPI8 have been found to be present in malaria parasites, and GPI3/PIG-A, GPI10/PIG-B, YJR013W/PIG-M, GPI13/PIG-O, GAA1/GAA-1, and DPM1 have been suggested to be present in malaria parasites (Delorenzi et al., Infect. Immun. 70: 4510-4522, 2002). The nucleotide sequences of GWT1, GPI1, GPI8, GPI3/PIG-A, GPI10/PIG-B, YJR013W/PIG-M, GPI13/PIG-O, GAA1/GAA-1, and DPM1 of P. falciparum are shown in SEQ ID NO: 1 and the even sequence identification numbers in SEQ ID NOs: 6-21, respectively. Each corresponding amino acid sequence is shown in SEQ ID NO: 2 and the odd sequence identification numbers in SEQ ID NOs: 6-21. In addition, the nucleotide sequence of P. vivax GWT1 is shown in SEQ ID NO: 3, and the corresponding amino acid sequence is shown in SEQ ID NO: 4. Using a method known to those skilled in the art, for example, a method using hybridization or PCR, GWT1, GPI1, GPI8, GPI3/PIG-A, GPI10/PIG-B, YJR013W/PIG-M, GPI13/PIG-O, GAA1/GAA-1, or DPM1 of other malaria parasites can be cloned using DNA comprising any one of the nucleotide sequences shown in SEQ ID NO: 1 and 3, and the even-numbered SEQ ID NOs: 6-21.

Furthermore, GPI synthase genes other than GWT1, GPI1, GPI8, GPI3/PIG-A, GPI10/PIG-B, YJR013W/PIG-M, GPI13/PIG-O, GAA1/GAA-1, and DPM1 of malaria parasites can be cloned by using yeast or human GPI synthase genes. The nucleotide sequences of GPI2, GPI15, YDR437W, GPI12, MCD4, GPI11, GPI7, GPI17, GPI16, and CDC91 of yeast (S. cerevisiae) are shown in the even sequence identification numbers in SEQ ID NOs: 22-41 respectively; and each corresponding amino acid sequence is shown in the odd sequence identification numbers in SEQ ID NOs: 22-41. In addition, the nucleotide sequences of human DPM2, DPM3, and SL15 are shown in the even sequence identification numbers in SEQ ID NOs: 42-47 respectively; and each corresponding amino acid sequence is shown in the odd sequence identification numbers in SEQ ID NOs: 42-47.

The production of a degenerate mutant DNA encoding a protein involved in the biosynthesis of the GPI of malaria parasites, and with a lower AT content than that of the original DNA, consists of two steps: design, and synthesis. In the design step, the amino acid sequence of a protein of interest is first reverse-translated and then possible codons for each amino acid residue are listed. Reverse translation can be achieved by using commercially available gene analysis software (for example, DNASIS-Pro; Hitachi Software Engineering Co., Ltd). Of the codons listed, those meeting the purpose (for example, codons whose AT content is lower and codons frequently used in the host to be used for gene expression) are selected for each amino acid. The degenerate mutant DNA can be designed by rearranging the amino acid sequence of the protein of interest using these selected codons.

The DNA thus designed can be synthesized by a method known to those skilled in the art. The degenerate mutant DNA of the present invention can be synthesized based on the designed nucleotide sequence by, for example, using a commercially available DNA synthesizer.

The present invention also provides vectors in which the above-described degenerate mutant DNA has been inserted, and transformants (preferably GPI synthase gene-deficient fungi) that retain the DNA or the vector in an expressible state. The vector and the host can be those described above.

As used herein, the expression "deficient in the GPI synthase gene" means that the functional product of the gene is not expressed, or that the expression level is decreased. The GPI synthase gene-deficient fungus of the present invention can be prepared by disrupting the GPI gene. The disruption can be achieved by inserting DNA unrelated to the gene, for example a selection marker, based on homologous recombination technology, and the like. More specifically, such a mutant fungus can be prepared by introducing into yeast a selection marker cassette which comprises the his5 gene or the kanamycin resistance gene of S. pombe (Longtine et al., Yeast, 14: 953-961, 1998) amplified with primers, each of which comprises a nucleotide sequence homologous to a portion of the gene (ranging from 50 to 70 nucleotides).

The GPI synthase gene-deficient fungus of the present invention includes, for example, the GWT1 temperature-sensitive mutant strain gwt1-20, GPI7 disruptant strain, GPI8 mutant strain gpi8-1, and GPI10 temperature-sensitive mutant strain per13-1.

A GPI synthase gene-deficient fungus which has been transformed with the degenerate mutant DNA of the present invention can be prepared by introducing into a fungus a vector into which the degenerate mutant DNA has been inserted. pRS316, YEp351, or such can be used as the vector for S. cerevisiae, and pcL, pALSK, or such can be used as the vector for S. pombe.

The present invention also provides a method of screening for antimalarial drugs, which comprises using GPI synthase gene-deficient fungi described above.

In such a method, the first step comprises contacting a test sample with a GPI synthase gene-deficient fungus that has been transformed with degenerate mutant DNA with a lower AT content than the DNA encoding a protein involved in the biosynthesis of GPI of malaria parasites. The "contact" can be achieved by adding a test sample to the culture of the above-mentioned fungus. When the test sample is a protein, a vector comprising DNA encoding the protein can be introduced into the above-mentioned fungus.

In the method of the present invention, the next step comprises measuring the degree of growth of the above-mentioned fungus. More specifically, the fungus is inoculated under typical culture conditions, specifically, the fungus is inoculated onto a liquid culture medium such as Yeast extract-polypeptone-dextrose medium (YPD medium) or onto an agar plate, and then incubated at 25 to 37° C. for 4 to 72 hours. Thus GPI synthase gene-deficient fungus transformed with the degenerate mutant DNA of the present invention can be assessed for growth. The degree of growth can also be determined using the turbidity of the culture liquid, the number of colonies, or the size or color of the spots formed on the agar plate as an index. In the method of the present invention, the next step comprises selecting compounds that inhibit the growth of the above-mentioned fungus.

In an alternative method, the first step comprises contacting a test sample with a GPI synthase gene-deficient fungus in which the above-described degenerate mutant DNA has been introduced. The next step comprises determining the amount of GPI-anchored protein transported onto the yeast cell wall. The detection method includes: (1) methods using a reporter enzyme; (2) methods using an antibody that reacts with a surface glycoprotein on the fungal cell wall; (3) methods using the ability to adhere to animal cells; and (4) methods using a light microscope or an electron microscope to observe the fungi. In the method of the present invention, the next step comprises selecting a sample that decreases the amount of GPI-anchored protein transported to the cell wall.

The present invention provides a method of screening for antimalarial drugs using a protein involved in the biosynthesis of GPI, which is prepared using a degenerate mutant DNA of the present invention. Such methods include, for example, a binding assay system where screening is carried out to select compounds that bind to a protein involved in GPI biosynthesis in competition with a labeled compound bound to the protein. Specifically, a degenerate mutant DNA of the present invention is introduced into the GPI synthase gene-deficient fungus, the protein encoded by the DNA is expressed in the fungus, and the expressed protein is prepared. The prepared protein is then contacted with a test sample and with a labeled compound that can bind to the protein. In the next step, the labeled compound bound to the protein is detected, and test samples that decrease the amount of labeled compound bound to the protein are selected.

The present invention also provides an assay system for GlcN-PI acyltransferase. Such a system comprises using a GWT1 protein which is prepared using a DNA encoding a protein that has the activity of complementing the phenotype of GWT1-deficient yeast, which the DNA is a degenerate mutant of a DNA encoding a malaria parasite GWT1 protein that has a lower AT content than the original DNA. Specifically, the degenerate mutant DNA is introduced into GWT1-deficient fungus, the protein encoded by the degenerate mutant DNA is expressed in the fungus, and the expressed protein is prepared. This protein is then contacted with a test sample, GlcN-(acyl)PI is detected, and a test sample that decreases the amount of GlcN-(acyl))PI is selected.

Any patents, patent applications, and publications cited herein are incorporated by reference in their entireties.

If one copy of the GWT1 gene was disrupted, only half of the spores grew. Thus, the ratio of [colony-forming spots]: [spots exhibiting no growth] is 2:2 in such cases. In the columns marked with an arrow, the lethal phenotype of the gwt1 disruptant was complemented by the introduced opfGWT1, and hence all four spots grew, each forming a colony.

Figure 2:
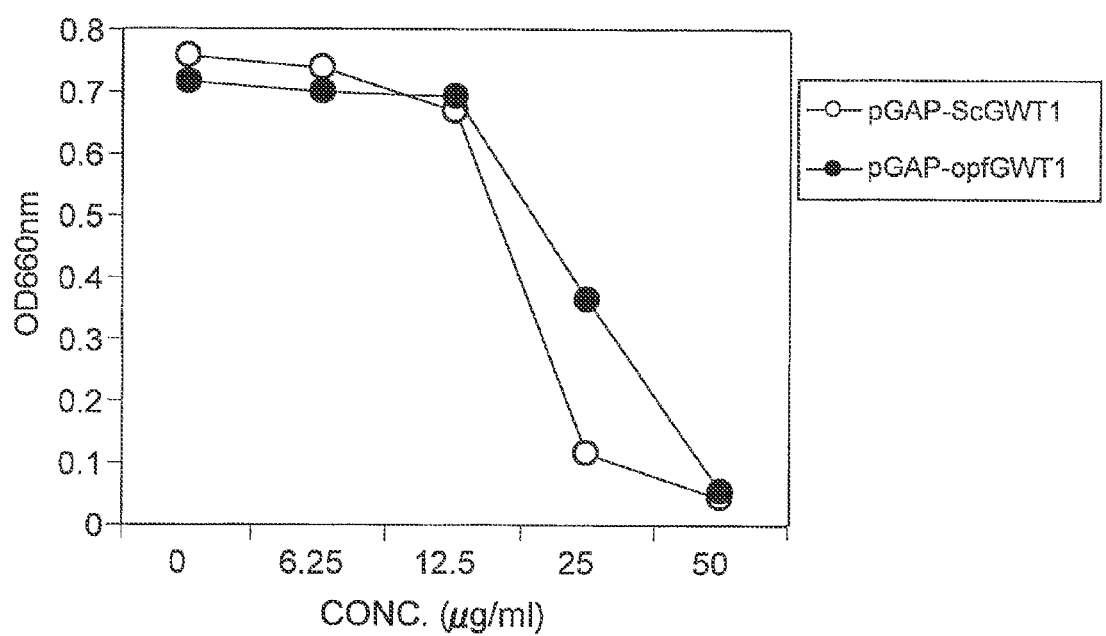

FIG. 2 depicts a diagram showing the inhibitory activity of a compound with respect to the growth of yeast expressing the opfGWT1 gene. Either the yeast GWT1 gene or opfGWT1 gene was expressed in GWT1 gene-disrupted yeast.

A compound having the activity of inhibiting the GWT1-dependent growth of yeast also showed inhibitory activity with respect to the opfGWT1-dependent growth of yeast in which opfGWT1 was expressed.

Figure 3:
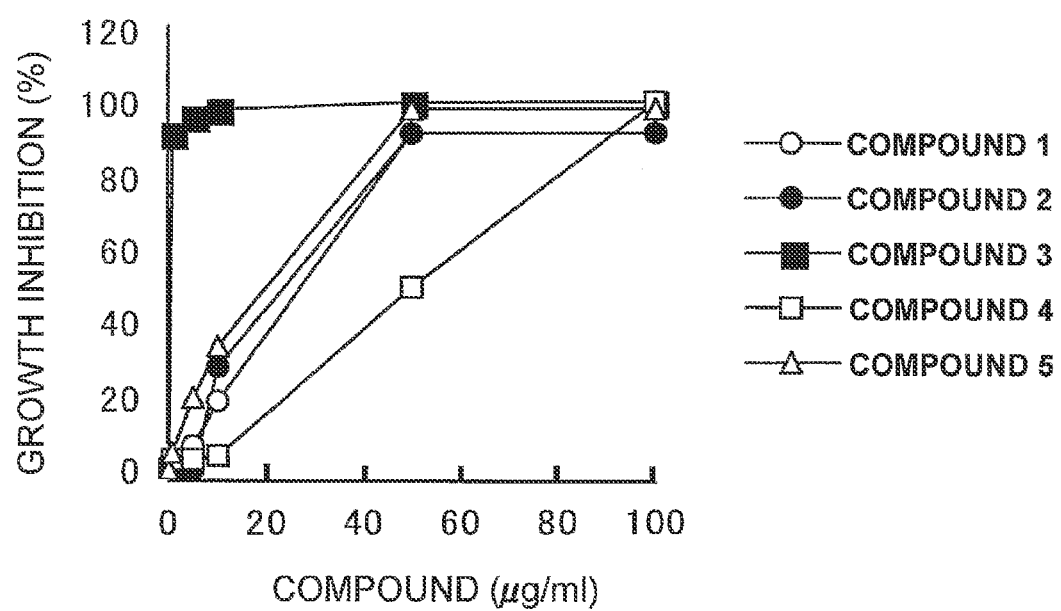

FIG. 3 depicts a diagram showing antimalarial activity. Human red blood cells were infected with *P. falciparum*. A GWT1-inhibiting compound was added to these red blood cells, and inhibition of malaria parasite infection was determined.

All five compounds exhibiting antifungal activity also inhibited the malaria parasite infection of red blood cells.

BEST MODE FOR CARRYING OUT THE INVENTION

Herein below, the present invention will be specifically described using Examples, but it is not to be construed as being limited thereto.

Example 1

*P. falciparum* GWT1 (PfGWT1)

(1) The nucleotide sequence of *P. falciparum* GWT1 (PfGWT1) (SEQ ID NO: 1) has been disclosed in the database of the *P. falciparum* genome (see PlasmoDB database on the World Wide Web). The PfGWT1 gene was cloned by PCR using genomic DNA purified from *P. falciparum* (the 3D7 strain) as a template. The 5' half and 3' half of the PfGWT1 gene were prepared separately, and the two halves were assembled at an XbaI (TCTAGA) restriction enzyme site. Thus, the full-length PfGWT1 gene was prepared. In addition, restriction enzymes sites outside the coding region were included, thus allowing insertion into an expression vector.

(2) The 5' half of the PfGWT1 gene was amplified by PCR using *P. falciparum* genomic DNA as a template and the primers pf152F (SEQ ID NO: 48) and pf136R (SEQ ID NO: 49). The 3' half was amplified by the same procedure described above, using the primers pf137F (SEQ ID NO: 50) and pf151R (SEQ ID NO: 51). The DNA fragments amplified were subcloned into the pT7-Blue vector (Novagen), and the nucleotide sequences of the inserts were sequenced to confirm homology to SEQ ID NO: 1. Clones containing the 5' half of the PfGWT1 gene were named PF15-5 clones. Clones containing the 3' half were named PF20-9 clones.

(3) Using PCR, cleavage sites for restriction enzymes were added outside the coding region to enable the PfGWT1 gene to be inserted into an expression vector. An EcoRI cleavage site was added to the 5' half by PCR using PF15-5 as a template and the primers pf154FE (SEQ ID NO: 52) and pf157R (SEQ ID NO: 53). The amplified DNA fragment was subcloned into the pT7-Blue vector (Novagen) to prepare the clone pT7-plasmN2. Likewise, the 3' half was amplified by PCR using PF20-9 as a template and the primers pf168BK (SEQ ID NO: 54) and pf155RK (SEQ ID NO: 55). The amplified DNA fragments were subcloned to prepare pT7-plasmBK5 clones.

(4) The full-length PfGWT1 gene was prepared by the procedure described below. The yeast expression vector YEp352GAPII was digested with the restriction enzymes EcoRI and KpnI. The EcoRI-XbaI fragment (about 1500 bp) derived from pT7-plasmN2, and the XbaI-KpnI fragment (about 1100 bp) derived from pT7-plasmBK5, were inserted into the vector at a cleaved site. The expression vector YEp352GAPII-PfGWT1 containing the full-length PfGWT1 was then constructed.

```
[pf152F]
                                        (SEQ ID NO: 48)
ATGACAATGTGGGGAAGTCAACGGg

[pf136R]
                                        (SEQ ID NO: 49)
TGTGTGGTTACCGTTCTTTGAATACATAGA

[pf137F]
                                        (SEQ ID NO: 50)
ATAGAAAATGATTTATGGTACAGCTCAAA

[pf151R]
                                        (SEQ ID NO: 51)
AGACCAAATTAATTATGCCTTTACATGTAC

[pf154FE]
                                        (SEQ ID NO: 52)
agaattcaccATGAGCAACATGAATATACTTGCGTATCTT

[pf157R]
                                        (SEQ ID NO: 53)
GAAATTCCAATGTATTCCATATTCACTTAT

[pf168BK]
                                        (SEQ ID NO: 54)
AAGATCTAATACATTAAAACATTTTAGATTAATGAATATGTG

[pf155RK]
                                        (SEQ ID NO: 55)
agqtaccGTACACTCCACTCTATGATGATCATTC
```

Example 2

A Fully Synthetic PfGWT1 Gene

The adenine and thymine (AT) proportion is exceedingly high (80% or higher) in *P. falciparum* DNA, and thus routine biological techniques (PCR, *E. coli*-based gene engineering, expression systems for recombinant proteins, and so on) are often unavailable (Sato and Horii; Protein, Nucleic acid, and Enzyme Vol. 48, 149-155, 2003). Likewise, the AT content of PfGWT1 DNA was 80.41% including many consecutive A or T stretches. Thus, the gene was predicted to be difficult to replicate and express as a protein in yeast. Indeed, when native PfGWT1 ligated with a yeast overexpression vector was introduced into GWT1 disrupted yeast, the PfGWT1 did not rescue the lethal phenotype of the GWT1 disruptant at all. To reduce AT content, codons were replaced with synonymous codons without changing the original amino acid sequence.

The codon substitution was carried out based on the nucleotide sequence of *P. falciparum* GWT1 (SEQ ID NO: 1) disclosed in the *P. falciparum* genome database (PlasmoDB database on the World Wide Web). The resulting nucleotide sequence was named "optimized PfGWT1 (opfGWT1)" (SEQ ID NO: 5).

The sequence described above was designed to include additional sequences outside the coding region; namely an EcoRI cleavage site sequence (GAATTC, at the 5' end), Kozak's sequence (ACC, at the 5' end), and a KpnI cleavage site sequence (GGTACC, at the 3' end). The synthesis of the resulting sequence was consigned to Blue Heron Inc. in the U.S.A. These additional restriction enzyme sites were used to ligate the fully synthetic opfGWT1 into the YEp352GAPII vector to construct an overexpression plasmid for opfGWT1. The construct was introduced into diploid cells (WDG2) in which only a single copy of the GWT1 gene had been disrupted. The resulting transformants were cultured on plates containing a sporulation medium to form spores for tetrad analysis.

Figure 1:
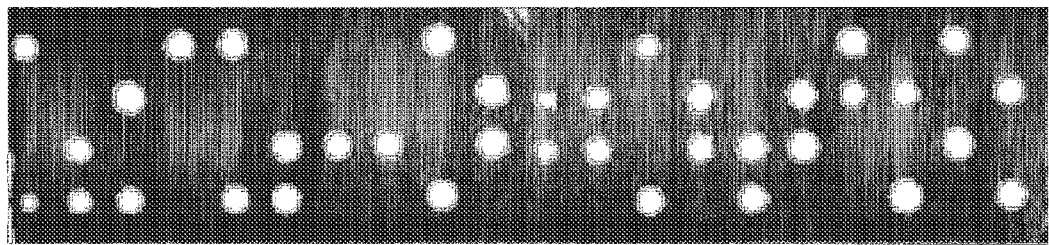
FIG. 1 depicts photographs showing the results of tetrad analysis. The gwt1-disrupted strain became viable after the introduction of the opfGWT1-overexpressing plasmid. The four spores derived from a single diploid cell were spotted vertically.
Figure 1:
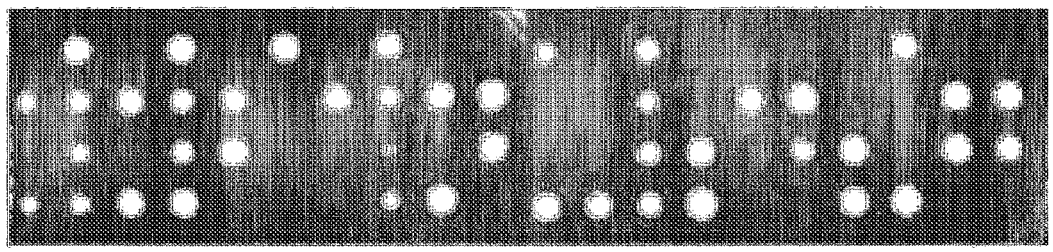
Figure 1:

The AT content of the newly designed codon-modified opfGWT1 was reduced to 61.55%. The results of tetrad analysis are shown in FIG. 1. The gwt1-disrupted strain became viable after introduction of the opfGWT1 overexpression plasmid. The findings described above indicate that the PfGWT1 gene can be expressed in yeast cells when its AT content is reduced by codon modification.

Example 3

An Assay for Antimalarial Activity Using opfGWT1-Expressing Yeast

A screening system for compounds having antimalarial activity was constructed using opfGWT1-expressing yeast.

An expression cassette was constructed by inserting the *S. cerevisiae* GWT1 terminator, and the *S. cerevisiae* GAPDH promoter and multi-cloning site into the SacI-KpnI site of the single-copy vector pRS316. *S. cerevisiae* GWT1 and opfGWT1 were inserted into the multi-cloning site to prepare pGAP-ScGWT1 and pGAP-opfGWT1 plasmids, respectively. These plasmids were introduced into the GWT1 disruptant. Serial two-fold dilutions of compound (1) were prepared using YPAD to make the highest final concentration 50 μg/ml. A 50 μl aliquot of the diluted compound was added to each well of a 96-well plate. Overnight cultures of yeast cells comprising each plasmid were diluted 1000-fold and then a 50 μl aliquot of the dilution was added to each well. The plates were incubated at 30° C. for two days, and then culture turbidity was determined at 660 nm (FIG. 2 and Table 1).

TABLE 1

|              | 0      | 6.25   | 12.5   | 25     | 50     |
|--------------|--------|--------|--------|--------|--------|
| pGAP-ScGWT1  | 0.7560 | 0.7370 | 0.6670 | 0.1140 | 0.0420 |
| pGAP-opfGWT1 | 0.7150 | 0.6990 | 0.6910 | 0.3630 | 0.0530 |

Although the GWT1 disruptant was nonviable, the strain became viable after introduction of each plasmid (as shown at 0 μg/ml of compound concentration). The growth of ScGWT1-expressing yeast was inhibited by compound (1), a GWT1-specific inhibitor. The use of the compound at 25 μg/ml resulted in about 85% inhibition of growth. When the compound was used at 50 μg/ml, the yeast was completely nonviable. The growth of opfGWT1-expressing yeast was also inhibited by compound (1). The use of the compound at 25 μg/ml resulted in about 50% inhibition of growth. When the compound was used at 50 μg/ml, the yeast was completely nonviable. Since growth of opfGWT1-expressing yeast depends on the activity of the introduced opfGWT1, growth inhibition can be attributed to the inhibition of the opfGWT1 function by compound (1). These findings suggest that compounds with *P. falciparum* GWT1-specific inhibitory activity GWT1 can be identified by screening compounds using this assay system.

Example 4

Antimalarial Activity

Representative compounds (1) to (5), that inhibit yeast GWT1, were assayed for antimalarial activity using a red blood cell culture system.

compound (1): 1-(4-butyl benzyl) isoquinoline compound (2): 4-[4-(1-isoquinolyl methyl) phenyl]-3-butyne-1-ol compound (3): 5-butyl-2-(1-isoquinolyl methyl) phenol compound (4): 2-(4-bromo-2-fluorobenzyl)-3-methoxypyridine compound (5): N-[2-(4-butyl benzyl)-3-pyridyl]-N-methylamine Specifically, a test compound was dissolved in 100% DMSO, diluted with a medium, and an 80 µl aliquot of the dilution was added to each well of a 96-well culture plate. *P. falciparum* FCR3 strain was pre-cultured in RPMI1640 medium containing 10% human serum at 37° C., and then 20 µl of the cultured cells (containing 10% red blood cells) was added to each well. At this time, 0.47% of red blood cells were infected. After culturing under 5% $O_2$, 5% $CO_2$, and 90% $N_2$ at 37° C. for 48 hours, the malaria parasites were stained using Giemsa staining. The number of protozoan-infected red blood cells was determined in order to estimate infection rate (FIG. 3). As a result, compound (3) was revealed to have strong antimalarial activity. The other four compounds also showed antimalarial activity. Compound (4) exhibited the lowest activity. Therefore, compounds inhibiting yeast GWT1 include compounds which have the activity of inhibiting *P. falciparum* GWT1, suggesting that antimalarial drugs can be synthesized based on such compounds.

INDUSTRIAL APPLICABILITY

The present invention succeeded in producing fungi that express malaria parasite GWT1. Using such fungi, antimalarial drugs targeting the pathway of GPI biosynthesis can be screened without using malaria parasites.

To date, no attempt has been made to express a malaria parasite gene in fungal cells and screen substances which inhibit the function of that gene. The methods of the present invention remove the need to actually using malaria parasites themselves, and thus this method proves the possibility of entirely new screening methods for drug discovery using comparative genomics in the post-genome era.

The invention claimed is:

1. An antimalarial drug which comprises as an active ingredient a compound that inhibits the activity of a protein encoded by an isolated DNA according to any one of (a) to (e), which encodes a protein of a malaria parasite having GlcN-PI acyltransferase activity:

(a) a DNA encoding a protein consisting of the amino acid sequence of SEQ ID NO: 2 or 4, (b) a DNA consisting of the nucleotide sequence of SEQ ID NO: 1 or 3, (c) a DNA hybridizing to DNA consisting of the nucleotide sequence of SEQ ID NO: 1 or 3 under stringent conditions, wherein the stringent conditions are hybridization in 4×SSC at 65° C. followed by washing in 0.1×SSC at 65° C. for one hour, (d) a DNA encoding a protein which consists of the amino acid sequence of SEQ ID NO: 2 or 4, in which 5 amino acids or fewer in SEQ ID NO: 2 or 4 have been added, deleted, substituted, and/or inserted, and (e) a DNA encoding a protein which has more than 95% identity to the amino acid sequence of SEQ ID NO: 2 or 4.

2. The antimalarial drug according to claim 1, wherein the compound is at least one selected from the group consisting of the following compounds (I) to (5):

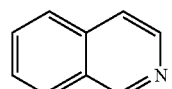

(1)

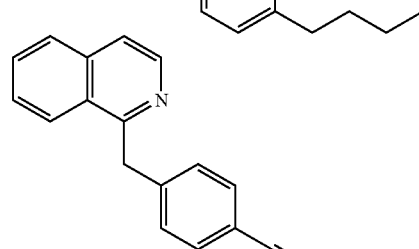

(2)

(3)

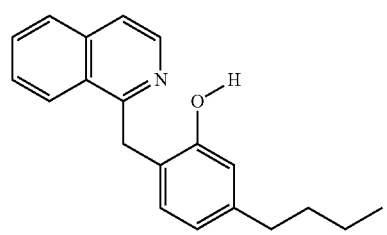

-continued
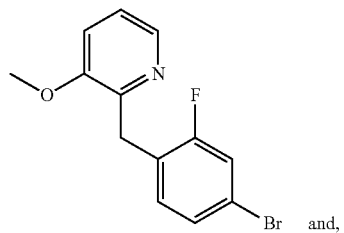 (4)
and,
-continued
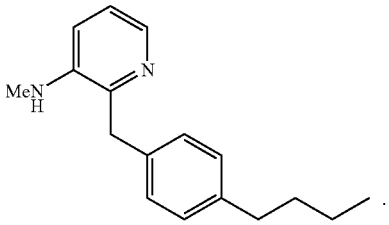 (5)
* * * * *